(12) United States Patent
Pinard et al.

(10) Patent No.: US 9,975,900 B2
(45) Date of Patent: May 22, 2018

(54) SUBSTITUTED IMIDAZO[1,2-α]PYRAZINES FOR TREATING SPINAL MUSCULAR ATROPHY

(71) Applicant: Hoffmann-La Roche Inc., Little Falls, NJ (US)

(72) Inventors: Emmanuel Pinard, Linsdorf (FR); Hasane Ratni, Habsheim (FR); Luke Green, Basel (CH); Patrick Williamson, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days. days.

(21) Appl. No.: 15/379,057

(22) Filed: Dec. 14, 2016

(65) Prior Publication Data
US 2017/0197969 A1   Jul. 13, 2017

Related U.S. Application Data

(63) Continuation of application No. PCT/EP2015/063894, filed on Jun. 22, 2015.

(30) Foreign Application Priority Data

Jun. 25, 2014 (EP) .................... 14173935

(51) Int. Cl.
*A61K 31/4985* (2006.01)
*C07D 487/04* (2006.01)
*C07D 519/00* (2006.01)

(52) U.S. Cl.
CPC .......... *C07D 487/04* (2013.01); *C07D 519/00* (2013.01)

(58) Field of Classification Search
CPC .................. A61K 31/4985; C07D 487/04

USPC .......................................... 514/249; 544/350
See application file for complete search history.

(56) References Cited

FOREIGN PATENT DOCUMENTS

WO   2014/012050 A2   1/2014
WO   2014/209841 A2   12/2014

OTHER PUBLICATIONS

ISR for PCT/EP2015/063894.
Markus Riessland et al., "The benzamide M344, a novel histone deacetylase inhibitior, significantly increases SMN2 RNA/protein levels in spinal muscular atrophy cells" Hum Genet 120:101-110 (May 25, 2006).

*Primary Examiner* — Douglas M Willis
(74) *Attorney, Agent, or Firm* — Mark D. Kafka; Genentech, Inc.

(57) ABSTRACT

The present invention provides compounds of formula (I)

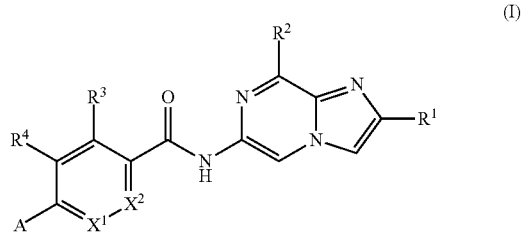

(I)

wherein A, $X^1$, $X^2$, $R^1$, $R^2$, $R^3$, $R^4$ and $R^5$ are as described herein, as well as pharmaceutically acceptable salts thereof. Further the present invention is concerned with the manufacture of the compounds of formula (I), pharmaceutical compositions comprising them and their use as medicaments.

20 Claims, No Drawings

SUBSTITUTED IMIDAZO[1,2-α]PYRAZINES FOR TREATING SPINAL MUSCULAR ATROPHY

CROSS-REFERENCE TO RELATED APPLICATIONS

This application is a continuation of, and claims priority to, International Patent Application No. PCT/EP2015/063894, filed on Jun. 22, 2015. This application also claims priority to European Patent Application No. 14173935.9, filed on Jun. 25, 2014. The entire contents of each of the above patent applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Mar. 23, 2017, is named P32086_SEQ_listing_as_filed.txt and is 1,477 bytes in size.

INTRODUCTION

The present invention provides compounds which are SMN2 gene splicing modulators, their manufacture, pharmaceutical compositions comprising them and their use as medicaments for the treatment of SMN-deficiency-related conditions, particularly for the treatment of spinal muscular atrophy (SMA).

In particular, the present invention relates to compounds of formula (I)

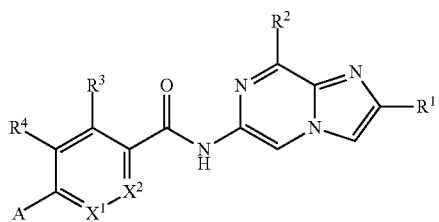

(I)

wherein $X^1$, $X^2$, A, $R^1$, $R^2$, $R^3$ and $R^4$ are as described herein, or pharmaceutically acceptable salts thereof.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival of Motor Neuron (SMN) gene and manifests over a wide range of severity affecting infants through adults (Crawford and Pardo, *Neurobiol. Dis.*, 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. Infants with a severe form of SMA frequently succumb to respiratory disease due to weakness in the muscles that support breathing. Individuals with milder forms of SMA live much longer, although they may need extensive medical support, especially those at the more severe end of the spectrum. The clinical spectrum of SMA disorders has been divided into the following five groups.

(a) Type 0 SMA (In utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.

(b) Type 1 SMA (Infantile SMA or Werdnig-Hoffmann disease) presents symptoms between 0 and 6 months. form of SMA is also very severe. Patients never achieve the ability to sit, and death usually occurs within the first 2 years without ventilatory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during their disease course but often become wheelchair-bound during youth or adulthood.

(e) Type 4 SMA (Adult onset SMA). Weakness usually begins in late adolescence in the tongue, hands, or feet, then progresses to other areas of the body. The course of adult SMA is much slower and has little or no impact on life expectancy.

The SMN gene has been mapped by linkage analysis to a complex region in chromosome 5q (Lefebvre S. et al., *Cell* (1995) 80:155). In humans, this region contains an approximately 500 thousand base pairs (kb) inverted duplication resulting in two nearly identical copies of the SMN gene. SMA is caused by an inactivating mutation or deletion of the telomeric copy of the gene (SMN1) on both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. SMN2 pre-mRNA undergoes alternative splicing of exon 7 caused by a translationally silent C to T mutation in exon 7. As a result, the majority of transcripts produced from SMN2 lack exon 7 (Δ7 SMN2), and encode a truncated SMN protein that has an impaired function and is rapidly degraded.

The SMN protein plays a role in RNA processing and metabolism, having a well characterized function of mediating the assembly of a specific class of RNA-protein complexes termed snRNPs. SMN may have other functions in motor neurons, however its role in preventing the selective degeneration of motor neurons is not well established.

In most cases, SMA is diagnosed based on clinical symptoms and by the complete absence of exon 7 of SMN1 gene. However, in approximately 5% of cases SMA is caused by mutation in genes other than the inactivation of SMN 1, some known and others not yet defined. In some cases, when the SMN 1 gene test is not feasible or does not show any abnormality, other tests such as an electromyography (EMG) or muscle biopsy may be indicated.

Medical care for SMA patients at present is limited to supportive therapy including respiratory, nutritional and rehabilitation care; there is no drug known to address the underlying cause of the disease. Current treatment for SMA consists of prevention and management of the secondary effects of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

Several mouse models of SMA have been developed. In particular, the SMN delta exon 7 (Δ7 SMN) model (Le et al., *Hum. Mol. Genet.*, 2005, 14:845) carries both the SMN2 gene and several copies of the Δ7 SMN2 cDNA and recapitulates many of the phenotypic features of Type 1 SMA. The Δ7 SMN model can be used for both SMN2 expression studies as well as the evaluation of motor function and survival. The C/C-allele mouse model (*Jackson Laboratory* strain #008714, The Jackson Laboratory, Bar Harbor, Me.) provides a less severe SMA disease model but does not have an overt muscle weakness. This mouse model has the murine Smn1 gene inactivated and carries both the complete SMN2 gene and a hybrid mSmn1-SMN2 gene that undergoes alternative splicing. C/C-allele mice have reduced levels of both SMN2 full length (FL SMN2) mRNA and SMN protein. The C/C-allele mouse model is used for SMN2 expression studies.

As a result of improved understanding of the genetic basis and pathophysiology of SMA, several strategies for treatment have been explored, but none have yet demonstrated success in the clinic.

Gene replacement of SMN1, using viral delivery vectors, and cell replacement, using differentiated SMN1$^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids: (i) antisense oligonucleotides that target sequence elements in SMN2 pre-mRNA and shift the outcome of the splicing reaction toward the generation of full length SMN2 mRNA (Passini et al., *Sci. Transl. Med.*, 2011, 3: 72ra18; and, Hua et al., *Nature*, 2011, 478:123) and (ii) trans-splicing RNA molecules that provide a fully functional RNA sequence that replace the mutant fragment during splicing and generate a full length SMN1 mRNA (Coady and Lorson, *J Neurosci.*, 2010, 30:126).

Other approaches under exploration include searching for drugs that increase SMN levels, enhance residual SMN function, or compensate for its reduced levels. Aminoglycosides have been shown to enhance the expression of a stabilized extended Δ7 SMN protein produced from Δ7 SMN2 mRNA by promoting the translational read-through of the aberrant stop codon, but have poor central nervous system penetration and are toxic after repeat dosing. Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators such as histone deacetylase (HDAC) inhibitors (e.g., butyrates, valproic acid, and hydroxyurea), and mRNA stabilizers (mRNA decapping inhibitor RG3039 from Pfizer), the goal being to increase the amount of total RNA transcribed from the SMN2 gene. However, the use of the HDAC inhibitors or mRNA stabilizers does not address the underlying cause of SMA and may result in a global increase in transcription and gene expression with potential safety problems in humans.

In an alternative approach, neuroprotective agents such as Olesoxime have been chosen for investigation. Such strategies are not aimed at SMN for the treatment of SMA, but instead are being explored to protect the SMN-deficient motor neurons from neurodegeneration.

A system designed for identifying compounds that increase the inclusion of exon 7 of SMN into RNA transcribed from the SMN2 gene and certain benzooxazole and benzoisoxazole compounds identified thereby have been described in International Patent Application WO2009/151546A1. A system designed for identifying compounds that cause ribosomal frameshifting to produce a stabilized SMN protein from Δ7 SMN2 mRNA and certain isoindolinone compounds identified thereby have been described in International Patent Applications WO2010/019236A1 and WO2013/119916A2.

Despite the progress made in understanding the genetic basis and pathophysiology of SMA, there remains a need to identify compounds that alter the course of spinal muscular atrophy, one of the most devastating childhood neurological diseases.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination $C_{1-7}$-alkoxy-heterocycloalkyl refers to a heterocycloalkyl which is substituted by $C_{1-7}$-alkoxy.

The term "moiety" refers to an atom or group of chemically bonded atoms that is attached to another atom or molecule by one or more chemical bonds thereby forming part of a molecule. For example, the variables A, $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The terms "optional" or "optionally" denote that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The terms "compound(s) of this invention" and "compound(s) of the present invention" refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulae.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid. Particular pharmaceutically acceptable salts of the present invention are salts formed with hydrochloric acid yielding a hydrochloride, dihydrochloride, or trihydrochloride salt, more particularly, a hydrochloride salt.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of the present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The terms "halo", "halogen", and "halide" are used interchangeably herein and denote fluoro, chloro, bromo, or iodo. Particular examples of halogen are fluoro and chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples for alkyl are methyl, ethyl and isopropyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl and the like. The term "perhaloalkyl" denotes an alkyl group where all hydrogen atoms of the alkyl group have been replaced by the same or different halogen atoms. Particular examples of haloalkyl are trifluoromethyl and difluoromethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy are methoxy and ethoxy.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S. In analogy, the term "tricyclic ring system" denotes three rings which are fused to each other as described for bicyclic ring systems.

The term "cycloalkyl" denotes a saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. One particular example of cycloalkyl is cyclopropyl.

The term "heterocycloalkyl" denotes a saturated or partly unsaturated mono-, bi- or tricyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples of a partly unsaturated heterocycloalkyl are dihydrofuryl, imidazolinyl, dihydro-oxazolyl, tetrahydro-pyridinyl, or dihydropyranyl. Particular examples of heterocycloalkyl are 1,4-diazepanyl, hexahydropyrrolo[1,2-a]pyrazinyl, piperidinyl, piperazinyl and pyrrolidinyl. More particular examples of heterocycloalkyl are piperazinyl and pyrrolidinyl.

The term "N-heterocycloalkyl" denotes a heterocycloalkyl radical containing at least one nitrogen ring atom and where the point of attachment of the heterocycloalkyl radical to the rest of the molecule is through a nitrogen ring atom. Particular examples of N-heterocycloalkyl are 1,4-diazepanyl, hexahydropyrrolo[1,2-a]pyrazinyl, piperidinyl, piperazinyl and pyrrolidinyl. More particular examples of N-heterocycloalkyl are piperazinyl and pyrrolidinyl.

The term "basicity" in reference to a compound is expressed herein by the negative decadic logarithm of the acidity constant of the conjugate acid (pKa=−log Ka). The larger the pKa of the conjugate acid, the stronger the base (pKa+pKb=14). In this application, an atom or functional group is denoted "basic" if it is suitable to accept a proton and if the calculated pKa of its conjugate acid is at least 7, more particularly if the calculated pKa of its conjugate acid is at least 7.8, most particularly if the calculated pKa of its conjugate acid is at least 8. pKa values were calculated in-silico as described in F. Milletti et al., *J. Chem. Inf. Model* (2007) 47:2172-2181.

The term "alkylene" denotes a linear saturated divalent hydrocarbon group of 1 to 7 carbon atoms or a divalent branched saturated hydrocarbon group of 3 to 7 carbon atoms. Examples of alkylene groups include methylene, ethylene, propylene, 2-methylpropylene, butylene, 2-ethylbutylene, pentylene, hexylene. Particular examples for alkylene are ethylene, propylene, and butylene.

The term "amino" denotes a group of the formula —NR'R" wherein R' and R" are independently hydrogen, alkyl, alkoxy, cycloalkyl, heterocycloalkyl, aryl, heteroaryl or as described herein. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is a group other than hydrogen. The term "tertiary amino" denotes a group wherein both R' and R" are other than hydrogen. Particular secondary and tertiary amines are methylamine, ethylamine, propylamine, isopropylamine, phenylamine, benzylamine dimethylamine, diethylamine, dipropylamine and diisopropylamine.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting group.

The terms "deprotection" or "deprotecting" denote the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

The term "SMN-deficiency-related conditions" comprises spinal muscular atrophy (SMA) neutogenic congenital arthrogryposis multiplex congenita (AMC), amyotrophic lateral sclerosis (ALS). The term "spinal muscular atrophy" (or SMA) relates to a disease caused by an inactivating mutation or deletion in the SMN1 gene on both chromosomes, resulting in a loss of SMN1 gene function.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA.

More particular, the term "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In further detail, the term "treating SMA" refers to the functional ability or retention of the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

The term "preventing" or "prevention" of a disease state denotes causing the clinical symptoms of the disease state not to develop in a subject that can be exposed to or predisposed to the disease state, but does not yet experience or display symptoms of the disease state.

The term "$EC_{1.5\times}$ concentration for production of full length SMN2 minigene mRNA" (or "$EC_{1.5\times}$ minigene") is defined as that concentration of test compound that is effective in increasing the amount of full length SMN2 minigene mRNA to a level 1.5-fold greater relative to that in vehicle-treated cells.

The term "$EC_{1.5\times}$ concentration for SMN protein expression" (or "$EC_{1.5\times}$ SMN protein") is defined as that concentration of test compound that is effective in producing 1.5 times the amount of SMN protein in an SMA patient fibroblast cell compared to the amount produced from the vehicle control.

In detail, the present invention relates to compounds of formula (I)

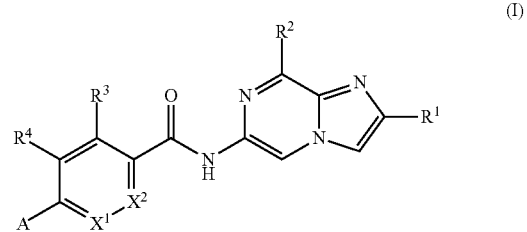

wherein
$X^1$ is $CR^5$ or N;
$X^2$ is $CR^5$ or N; with the proviso that not both $X^1$ and $X^2$ are N;
$R^1$ is hydrogen or $C_{1-7}$-alkyl;
$R^2$ is hydrogen, cyano, $C_{1-7}$-haloalkyl or $C_{3-8}$-cycloalkyl;
$R^3$ is hydrogen, halo, $C_{1-7}$-alkyl, or $C_{1-7}$-alkoxy;
$R^4$ is hydrogen, halo, $C_{1-7}$-alkyl, or $C_{1-7}$-alkoxy;
$R^5$ is independently selected from hydrogen, halo, $C_{1-7}$-alkyl, or $C_{1-7}$-alkoxy;
A is N-heterocycloalkyl or $NR^7R^8$, wherein N-heterocycloalkyl comprises 1 or 2 nitrogen ring atoms and is optionally substituted with 1, 2, 3 or 4 substituents selected from $R^6$;

R⁶ is independently selected from hydrogen, C₁₋₇-alkyl, amino, amino-C₁₋₇-alkyl, C₃₋₈-cycloalkyl, heterocycloalkyl and C₁₋₇-alkoxy-heterocycloalkyl or two R⁶ together form C₁₋₇-alkylene;

R⁷ is heterocycloalkyl comprising 1 nitrogen ring atom, wherein heterocycloalkyl is optionally substituted with 1, 2, 3 or 4 substituents selected from R⁶;

R⁸ is hydrogen, C₁₋₇-alkyl or C₃₋₈-cycloalkyl;

with the proviso that if A is N-heterocycloalkyl comprising only 1 nitrogen ring atom, then at least one R⁶ substituent is amino or amino-C₁₋₇-alkyl;

or pharmaceutically acceptable salts thereof.

Particular embodiments of the present invention are compounds of formula (I) or pharmaceutically acceptable salts thereof.

Further, it is to be understood that every embodiment relating to a specific X¹, X², A, R¹, R², R³ or R⁴ as disclosed herein may be combined with any other embodiment relating to another X¹, X², A, R¹, R², R³ or R⁴ as disclosed herein.

A particular embodiment of the present invention relates to compounds of formula (I) wherein X¹ is CH or N;
X² is CR⁵;
R¹ is C₁₋₇-alkyl;
R² is hydrogen, C₁₋₇-alkyl, C₁₋₇-haloalkyl or C₃₋₈-cycloalkyl;
R³ is hydrogen, halo, C₁₋₇-alkyl, or C₁₋₇-alkoxy;
R⁴ is hydrogen, halo, C₁₋₇-alkyl, or C₁₋₇-alkoxy;
R⁵ is hydrogen, halo, C₁₋₇-alkyl, or C₁₋₇-alkoxy;
A is N-heterocycloalkyl, wherein N-heterocycloalkyl comprises 1 or 2 nitrogen ring atoms and is optionally substituted with 1, 2, 3 or 4 substituents selected from R⁶;
R⁶ is independently selected from hydrogen, C₁₋₇-alkyl, amino, amino-C₁₋₇-alkyl, C₃₋₈-cycloalkyl, heterocycloalkyl and C₁₋₇-alkoxy-heterocycloalkyl or two R⁶ together form C₁₋₇-alkylene;
with the proviso that if A is N-heterocycloalkyl comprising only 1 nitrogen ring atom, then at least one R⁶ substituent is amino or amino-C₁₋₇-alkyl;
or pharmaceutically acceptable salts thereof.

A particular embodiment of the present invention relates to compounds of formula (I), wherein X¹ is N; with the proviso that not both X¹ and X² are N.

A particular embodiment of the present invention relates to compounds of formula (I), wherein X¹ is CR⁵.

A particular embodiment of the present invention relates to compounds of formula (I), wherein X¹ is CH.

A particular embodiment of the present invention relates to compounds of formula (I), wherein X² is N; with the proviso that not both X¹ and X² are N.

A particular embodiment of the present invention relates to compounds of formula (I), wherein X² is CR⁵.

A particular embodiment of the present invention relates to compounds of formula (I), wherein X² is CH.

A particular embodiment of the present invention relates to compounds of formula (I), wherein R¹ is C₁₋₇-alkyl, particularly methyl.

A particular embodiment of the present invention relates to compounds of formula (I), wherein R² is hydrogen, C₁₋₇-alkyl, C₁₋₇-haloalkyl or C₃₋₈-cycloalkyl; particularly hydrogen or C₁₋₇-haloalkyl; most particularly C₁₋₇-haloalkyl.

An even more particular embodiment of the present invention relates to compounds of formula (I), wherein R² is hydrogen, methyl, ethyl, difluoromethyl, trifluoromethyl or cyclopropyl; particularly hydrogen, difluoromethyl or trifluoromethyl; most particularly trifluoromethyl.

A particular embodiment of the present invention relates to compounds of formula (I), wherein R³ is hydrogen, halo or C₁₋₇-alkoxy, particularly halo.

An even more particular embodiment of the present invention relates to compounds of formula (I), wherein R³ is hydrogen, fluoro, methoxy or ethoxy, particularly fluoro.

A particular embodiment of the present invention relates to compounds of formula (I), wherein R⁴ is hydrogen or halo, particularly hydrogen.

An even more particular embodiment of the present invention relates to compounds of formula (I), wherein R⁴ is hydrogen or fluoro, particularly hydrogen.

A particular embodiment of the present invention relates to compounds of formula (I), wherein R⁵ is hydrogen, halo or C₁₋₇-alkoxy, particularly hydrogen.

An even more particular embodiment of the present invention relates to compounds of formula (I), wherein R⁵ is hydrogen, fluoro, chloro or methoxy, particularly hydrogen.

A particular embodiment of the present invention relates to compounds of formula (I), wherein R⁶ is independently selected from C₁₋₇-alkyl, heterocycloalkyl and C₁₋₇-alkoxy-heterocycloalkyl or two R⁶ together form C₁₋₇-alkylene.

A particular embodiment of the present invention relates to compounds of formula (I), wherein R⁶ is independently selected from methyl, ethyl, isopropyl, methoxy-azetidinyl and pyrrolidinyl or two R⁶ together form ethylene or propylene.

A particular embodiment of the present invention relates to compounds of formula (I), wherein R⁷ is piperazinyl optionally substituted with 1, 2, 3 or 4 substituents selected from R⁶.

A particular embodiment of the present invention relates to compounds of formula (I), wherein R⁸ is hydrogen or C₁₋₇-alkyl, particularly hydrogen or methyl.

A particular embodiment of the present invention relates to compounds of formula (I')

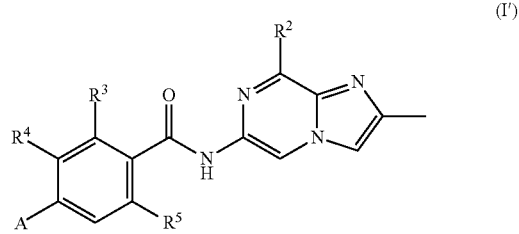

wherein A, R², R³, R⁴ and R⁵ are as described herein; or pharmaceutically acceptable salts thereof.

A particular embodiment of the present invention relates to compounds of formula (I), wherein A is a saturated mono- or bicyclic N-heterocycloalkyl comprising 1 or 2 nitrogen atoms and is optionally substituted with 1, 2, 3 or 4 substituents selected from R⁶.

A particular embodiment of the present invention relates to compounds of formula (I), wherein the N-heterocycloalkyl in A or the heterocycloalkyl in R⁷ as defined herein are substituted with 1 or 2 substituents selected from R⁶.

A particular embodiment of the present invention relates to compounds of formula (I), wherein the N-heterocycloalkyl in A as defined herein is further characterized in that one ring nitrogen atoms is basic.

A particular embodiment of the present invention relates to compounds of formula (I),
wherein A is

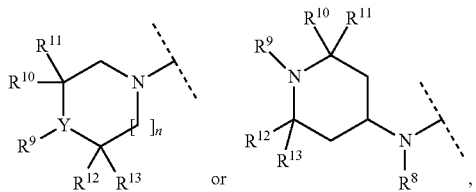

wherein
Y is N or CH;
R$^8$ is hydrogen, C$_{1-7}$-alkyl or C$_{3-8}$-cycloalkyl;
R$^9$ is hydrogen, C$_{1-7}$-alkyl, or —(CH$_2$)$_m$—NR$^{14}$R$^{15}$;
R$^{10}$ is hydrogen or C$_{1-7}$-alkyl;
R$^{11}$ is hydrogen or C$_{1-7}$-alkyl;
R$^{12}$ is hydrogen or C$_{1-7}$-alkyl;
R$^{13}$ is hydrogen or C$_{1-7}$-alkyl;
R$^{14}$ and R$^{15}$ are independently selected from hydrogen, C$_{1-7}$-alkyl and C$_{3-8}$-cycloalkyl;
n is 0, 1 or 2;
m is 0, 1, 2 or 3;
or R$^9$ and R$^{10}$ together form C$_{1-7}$-alkylene;
or R$^9$ and R$^{12}$ together form C$_{1-7}$-alkylene;
or R$^{10}$ and R$^{11}$ together form C$_{2-7}$-alkylene;
or R$^{10}$ and R$^{12}$ together form C$_{1-7}$-alkylene;
or R$^{10}$ and R$^{14}$ together form C$_{1-7}$-alkylene;
or R$^{12}$ and R$^{13}$ together form C$_{2-7}$-alkylene;
or R$^{12}$ and R$^{14}$ together form C$_{1-7}$-alkylene;
or R$^{14}$ and R$^{15}$ together form C$_{2-7}$-alkylene which is optionally substituted with alkoxy;
with the proviso that if Y is CH then R$^9$ is —(CH$_2$)$_m$—NR$^{14}$R$^{15}$; and
with the proviso that if Y is N and R$^9$ is —(CH$_2$)$_m$—NR$^{14}$R$^{15}$ then m is 2 or 3.

A particular embodiment of the present invention relates to compounds of formula (I), wherein A is

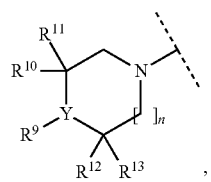

wherein Y, n, R$^9$, R$^{10}$, R$^{11}$, R$^{12}$ and R$^{13}$ are as defined above.

It has been found that brain penetration is improved when at least one of R$^9$, R$^{10}$, R$^{11}$, R$^{12}$ and R$^{13}$ is not hydrogen. In a particular embodiment of the invention at least one of R$^9$, R$^{10}$, R$^{11}$, R$^{12}$ and R$^{13}$ is other than hydrogen.

A particular embodiment of the present invention relates to compounds of formula (I), wherein Y is N.

A particular embodiment of the present invention relates to compounds of formula (I), wherein Y is CH and R$^9$ is —(CH$_2$)$_m$—NR$^{14}$R$^{15}$.

A particular embodiment of the present invention relates to compounds of formula (I), wherein Y is CH, R$^9$ is —(CH$_2$)$_m$—NR$^{14}$R$^{15}$ and m is 0.

A particular embodiment of the present invention relates to compounds of formula (I), wherein n is 1.

A particular embodiment of the present invention relates to compounds of formula (I), wherein R$^9$ is hydrogen, pyrrolidinyl, or methoxy-azetidinyl, more particularly hydrogen.

A particular embodiment of the present invention relates to compounds of formula (I), wherein R$^{10}$ is hydrogen, methyl, ethyl or isopropyl, more particularly methyl.

A particular embodiment of the present invention relates to compounds of formula (I), wherein R$^{11}$ is hydrogen or methyl, more particularly hydrogen.

A particular embodiment of the present invention relates to compounds of formula (I), wherein R$^{12}$ is hydrogen or methyl, more particularly hydrogen.

A particular embodiment of the present invention relates to compounds of formula (I), wherein R$^{13}$ is hydrogen.

A particular embodiment of the present invention relates to compounds of formula (I), wherein R$^9$ and R$^{10}$ together form propylene.

A particular embodiment of the present invention relates to compounds of formula (I), wherein R$^{10}$ and R$^{11}$ together form ethylene.

A particular embodiment of the present invention relates to compounds of formula (I), wherein R$^{14}$ and R$^{15}$ together form propylene or butylene.

A particular embodiment of the present invention relates to compounds of formula (I), wherein R$^{14}$ and R$^{15}$ together form propylene.

A particular embodiment of the present invention relates to compounds of formula (I), wherein R$^{14}$ and R$^{15}$ together form butylene.

A particular embodiment of the present invention relates to compounds of formula (I), wherein A is selected from the group of:

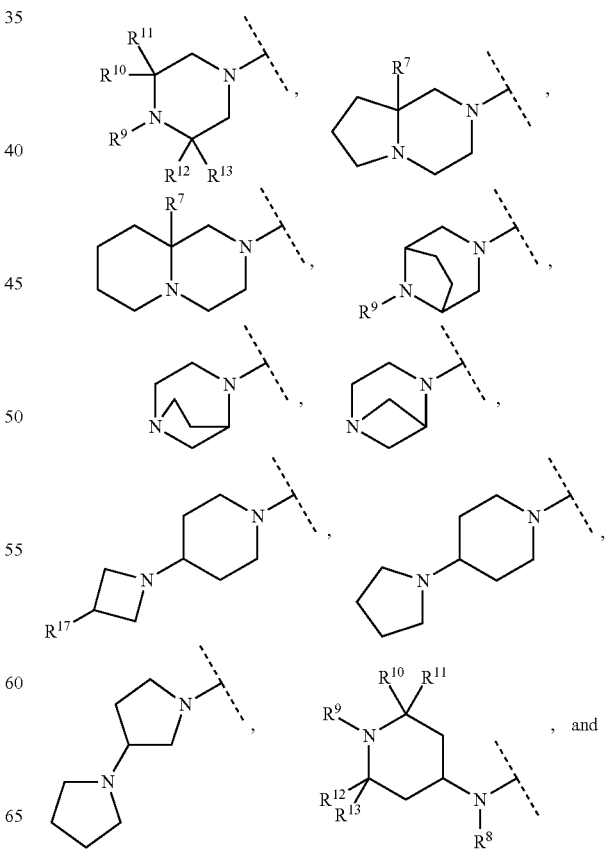

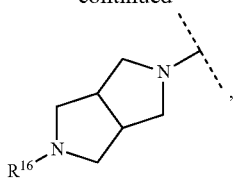

wherein $R^8$, $R^9$, $R^{10}$, $R^{11}$, $R^{12}$, and $R^{13}$ are as defined herein, $R^{16}$ is hydrogen or $C_{1-7}$-alkyl and $R^{17}$ is $C_{1-7}$-alkoxy.

A particular embodiment of the present invention relates to compounds of formula (I), wherein A is selected from the group of:

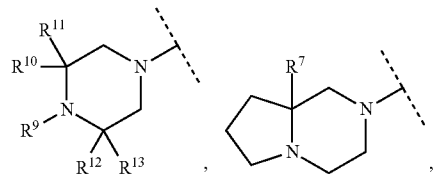

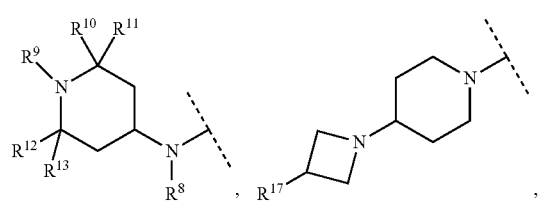

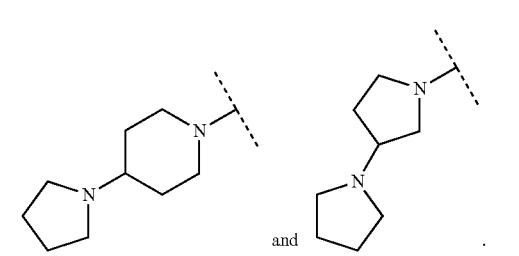

wherein $R^8$, $R^9$, $R^{10}$, $R^{11}$, $R^{12}$, and $R^{13}$ are as defined herein and $R^{17}$ is $C_{1-7}$-alkoxy.

A particular embodiment of the present invention relates to compounds of formula (I), wherein A is selected from the group of piperazinyl, diazepanyl, pyrrolidinyl and hexahydropyrrolo[1,2-a]pyrazinyl, each optionally substituted with 1, 2, 3 or 4 substituents selected from $R^6$ as defined herein.

A particular embodiment of the present invention relates to compounds of formula (I), wherein A is selected from the group of piperazin-1-yl, 1,4-diazepan-1-yl, pyrrolidin-1-yl and hexahydropyrrolo[1,2-a]pyrazin-2(1H)-yl, each optionally substituted with 1 or 2 substituents selected from $R^6$ as defined herein.

A particular embodiment of the present invention relates to compounds of formula (I), wherein A is $NR^7R^8$, wherein $R^7$ and $R^8$ are as described herein.

A particular embodiment of the present invention relates to compounds of formula (I), wherein A is

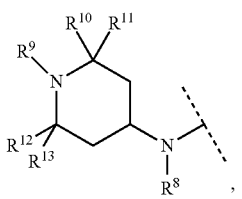

wherein $R^8$, $R^9$, $R^{10}$, $R^{11}$, $R^{12}$ and $R^{13}$ are as described herein.

A particular embodiment of the present invention relates to compounds of formula (I), wherein A is

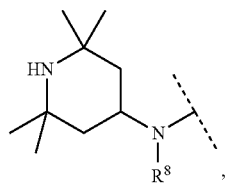

wherein $R^8$ is hydrogen or methyl.

A particular embodiment of the present invention relates to compounds of formula (I), wherein A is selected from the group of:

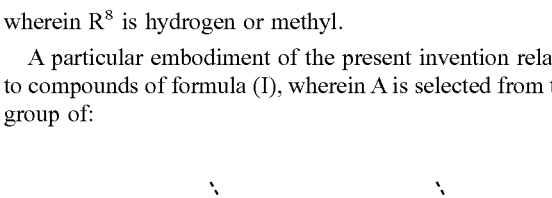

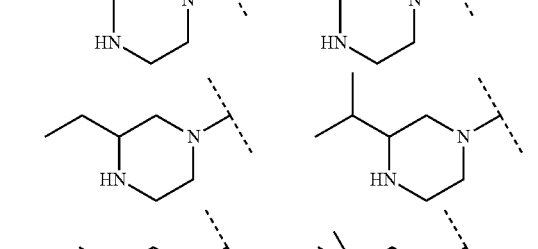

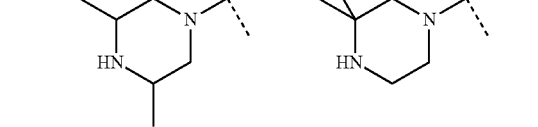

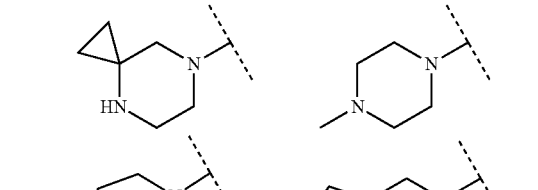

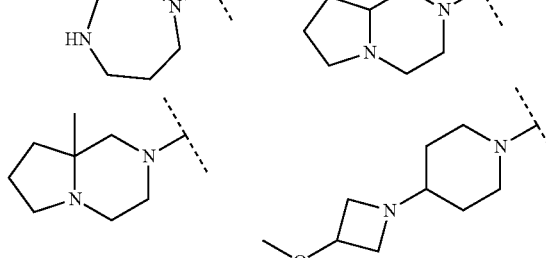

A particular embodiment of the present invention relates to compounds of formula (I), wherein A is selected from the group of:

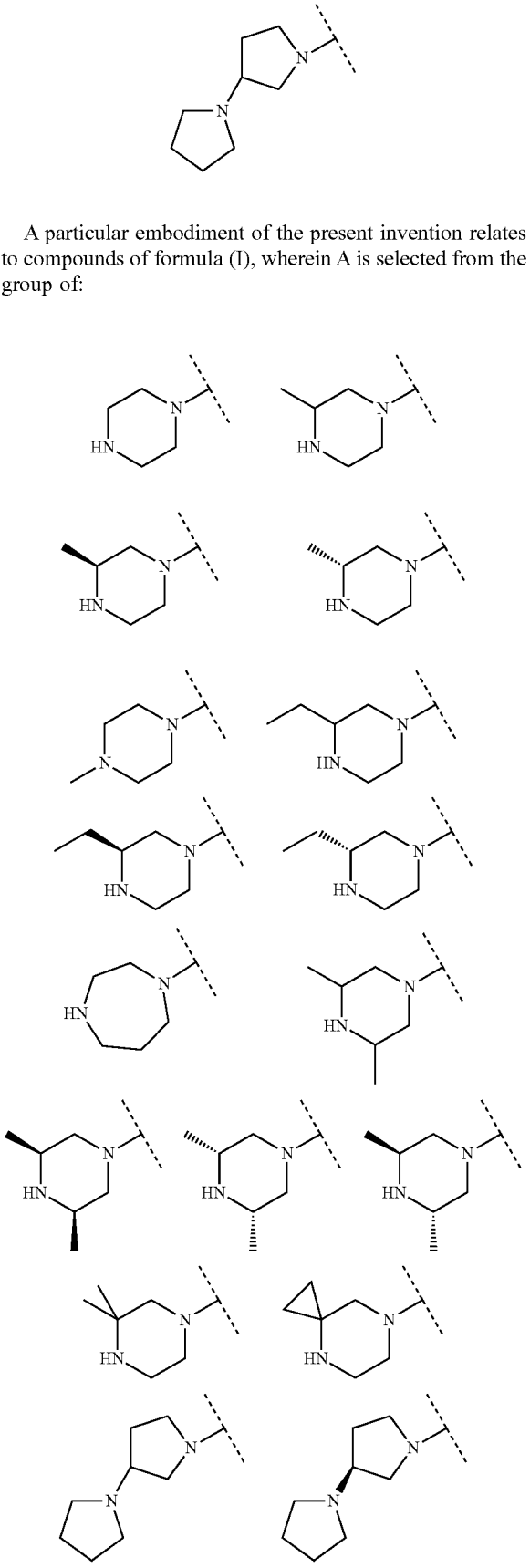

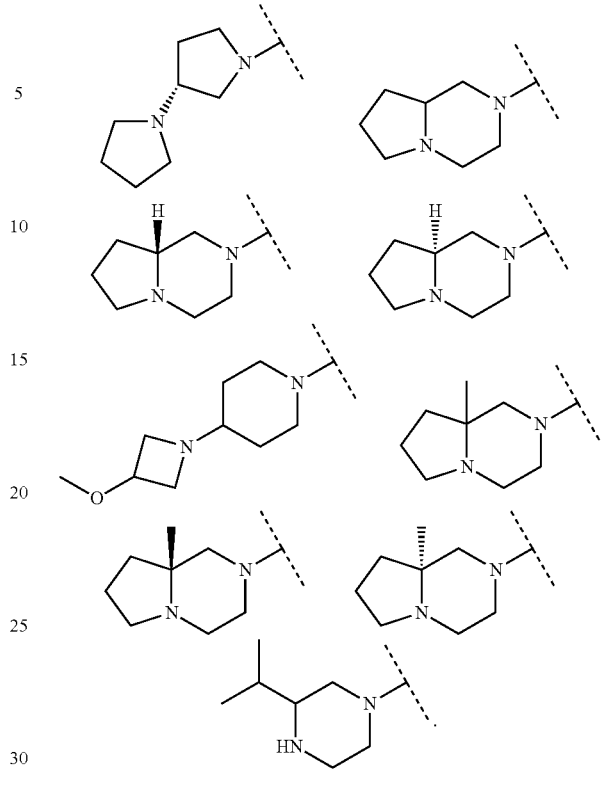

Particular compounds of formula (I) of the present invention are those selected from the group consisting of:
2-fluoro-N-(2-methylimidazo[1,2-a]pyrazin-6-yl)-4-piperazin-1-ylbenzamide;
N-(2-methylimidazo[1,2-a]pyrazin-6-yl)-4-piperazin-1-ylbenzamide;
4-[(8aS)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
2-ethoxy-N-(2-methylimidazo[1,2-a]pyrazin-6-yl)-4-[(3S)-3-methylpiperazin-1-yl]benzamide;
2-ethoxy-N-(2-methylimidazo[1,2-a]pyrazin-6-yl)-4-[(3R)-3-methylpiperazin-1-yl]benzamide;
4-[(8aR)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
4-[(8aR)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
4-[(8aS)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
4-(1,4-diazepan-1-yl)-2-ethoxy-N-(2-methylimidazo[1,2-a]pyrazin-6-yl)benzamide;
4-[(3S,5R)-3,5-dimethylpiperazin-1-yl]-2-ethoxy-N-(2-methylimidazo[1,2-a]pyrazin-6-yl)benzamide;
N-(2,8-dimethylimidazo[1,2-a]pyrazin-6-yl)-2-fluoro-4-[(3R)-3-methylpiperazin-1-yl]benzamide;
4-[(8aS)-3,4,6,7,8,8a-hexahydro-1H-pyrrolo[1,2-a]pyrazin-2-yl]-N-(2,8-dimethylimidazo[1,2-a]pyrazin-6-yl)-2-ethoxybenzamide;
4-[(8aS)-3,4,6,7,8,8a-hexahydro-1H-pyrrolo[1,2-a]pyrazin-2-yl]-N-(2,8-dimethylimidazo[1,2-a]pyrazin-6-yl)-2-fluorobenzamide;

N-(2,8-dimethylimidazo[1,2-a]pyrazin-6-yl)-2,6-difluoro-4-[(3R)-3-methylpiperazin-1-yl]benzamide;
N-(2, 8-dimethylimidazo[1,2-a]pyrazin-6-yl)-2-ethoxy-4-[(3R)-3-methylpiperazin-1-yl]benzamide;
4-[(8aS)-3,4,6,7,8,8a-hexahydro-1H-pyrrolo[1,2-a]pyrazin-2-yl]-N-(8-ethyl-2-methylimidazo[1,2-a]pyrazin-6-yl)-2-fluorobenzamide;
4-[(8aS)-3,4,6,7,8,8a-hexahydro-1H-pyrrolo[1,2-a]pyrazin-2-yl]-N-(8-cyclopropyl-2-methylimidazo[1,2-a]pyrazin-6-yl)-2-fluorobenzamide;
4-[(8aS)-3,4,6,7,8,8a-hexahydro-1H-pyrrolo[1,2-a]pyrazin-2-yl]-N-(2,8-dimethylimidazo[1,2-a]pyrazin-6-yl)-2,6-difluorobenzamide;
N-(2,8-dimethylimidazo[1,2-a]pyrazin-6-yl)-4-[(3R,5S)-3,5-dimethylpiperazin-1-yl]-2-fluorobenzamide;
N-(2,8-dimethylimidazo[1,2-a]pyrazin-6-yl)-2-fluoro-4-[(3S)-3-pyrrolidin-1-ylpyrrolidin-1-yl]benzamide;
N-(8-ethyl-2-methylimidazo[1,2-a]pyrazin-6-yl)-2-fluoro-4-[(3R)-3-methylpiperazin-1-yl]benzamide;
4-[(8aR)-3,4,6,7,8,8a-hexahydro-1H-pyrrolo[1,2-a]pyrazin-2-yl]-N-(8-cyclopropyl-2-methylimidazo[1,2-a]pyrazin-6-yl)-2-fluorobenzamide;
N-(8-cyclopropyl-2-methylimidazo[1,2-a]pyrazin-6-yl)-2-fluoro-4-[(3R)-3-methylpiperazin-1-yl]benzamide;
2-fluoro-N-(2-methylimidazo[1,2-a]pyrazin-6-yl)-4-[(3S)-3-pyrrolidin-1-ylpyrrolidin-1-yl]benzamide;
2-fluoro-N-(2-methylimidazo[1,2-a]pyrazin-6-yl)-4-[(3R)-3-methylpiperazin-1-yl]benzamide;
4-(4,7-diazaspiro[2.5]octan-7-yl)-2-fluoro-N-(2-methylimidazo[1,2-a]pyrazin-6-yl)benzamide;
4-[(3S,5R)-3,5-dimethylpiperazin-1-yl]-2-fluoro-N-(2-methylimidazo[1,2-a]pyrazin-6-yl)benzamide;
2-chloro-6-fluoro-N-(2-methylimidazo[1,2-a]pyrazin-6-yl)-4-piperazin-1-ylbenzamide;
2,5-difluoro-N-(2-methylimidazo[1,2-a]pyrazin-6-yl)-4-(3-methylpiperazin-1-yl)benzamide;
2,3-difluoro-N-(2-methylimidazo[1,2-a]pyrazin-6-yl)-4-(3-methylpiperazin-1-yl)benzamide;
4-[(3R,5S)-3,5-dimethylpiperazin-1-yl]-2-methoxy-N-(2-methylimidazo[1,2-a]pyrazin-6-yl)benzamide;
4-[(3R)-3-ethylpiperazin-1-yl]-2-fluoro-N-(2-methylimidazo[1,2-a]pyrazin-6-yl)benzamide;
2-fluoro-N-(2-methylimidazo[1,2-a]pyrazin-6-yl)-4-[(3R)-3-pyrrolidin-1-ylpyrrolidin-1-yl]benzamide;
4-(4,7-diazaspiro[2.5]octan-7-yl)-2-methoxy-N-(2-methylimidazo[1,2-a]pyrazin-6-yl)benzamide;
4-(3,3-dimethylpiperazin-1-yl)-2-fluoro-N-(2-methylimidazo[1,2-a]pyrazin-6-yl)benzamide;
N-(8-cyclopropyl-2-methylimidazo[1,2-a]pyrazin-6-yl)-4-[(3R)-3-ethylpiperazin-1-yl]-2-fluorobenzamide;
N-(8-cyclopropyl-2-methylimidazo[1,2-a]pyrazin-6-yl)-4-(3,3-dimethylpiperazin-1-yl)-2-fluorobenzamide;
2-methoxy-N-(2-methylimidazo[1,2-a]pyrazin-6-yl)-4-[(3R)-3-methylpiperazin-1-yl]benzamide;
2-methoxy-N-(2-methylimidazo[1,2-a]pyrazin-6-yl)-4-[(3R)-3-pyrrolidin-1-ylpyrrolidin-1-yl]benzamide;
4-[(3R)-3-ethylpiperazin-1-yl]-2-methoxy-N-(2-methylimidazo[1,2-a]pyrazin-6-yl)benzamide;
4-(3,3-dimethylpiperazin-1-yl)-2-methoxy-N-(2-methylimidazo[1,2-a]pyrazin-6-yl)benzamide;
4-[(3S)-3-ethylpiperazin-1-yl]-2-fluoro-N-(2-methylimidazo[1,2-a]pyrazin-6-yl)benzamide;
2-fluoro-4-[(3R)-3-methylpiperazin-1-yl]-N-[2-methyl-8-(trifluoromethyl)imidazo[1,2-a]pyrazin-6-yl]benzamide;
N-[8-(difluoromethyl)-2-methylimidazo[1,2-a]pyrazin-6-yl]-2-fluoro-4-[(3R)-3-methylpiperazin-1-yl]benzamide;
2-fluoro-N-(2-methylimidazo[1,2-a]pyrazin-6-yl)-4-(3-propan-2-ylpiperazin-1-yl)benzamide;
6-[(3R)-3-ethylpiperazin-1-yl]-2-methoxy-N-(2-methylimidazo[1,2-a]pyrazin-6-yl)pyridine-3-carboxamide;
2-methoxy-N-(2-methylimidazo[1,2-a]pyrazin-6-yl)-6-piperazin-1-ylpyridine-3-carboxamide;
N-(2,8-dimethylimidazo[1,2-a]pyrazin-6-yl)-2-fluoro-4-(4-pyrrolidin-1-ylpiperidin-1-yl)benzamide;
N-(2,8-dimethylimidazo[1,2-a]pyrazin-6-yl)-2-ethoxy-4-[4-(3-methoxyazetidin-1-yl)piperidin-1-yl]benzamide;
and pharmaceutically acceptable salts thereof.

Particular compounds of formula (I) of the present invention are those selected from the group consisting of:
4-(4,7-diazaspiro[2.5]octan-7-yl)-2-fluoro-N-(2-methylimidazo[1,2-a]pyrazin-6-yl)benzamide;
4-[(3S,5R)-3,5-dimethylpiperazin-1-yl]-2-fluoro-N-(2-methylimidazo[1,2-a]pyrazin-6-yl)benzamide;
4-[(3R)-3-ethylpiperazin-1-yl]-2-fluoro-N-(2-methylimidazo[1,2-a]pyrazin-6-yl)benzamide;
2-fluoro-N-(2-methylimidazo[1,2-a]pyrazin-6-yl)-4-[(3R)-3-pyrrolidin-1-ylpyrrolidin-1-yl]benzamide;
4-[(3S)-3-ethylpiperazin-1-yl]-2-fluoro-N-(2-methylimidazo[1,2-a]pyrazin-6-yl)benzamide;
2-fluoro-4-[(3R)-3-methylpiperazin-1-yl]-N-[2-methyl-8-(trifluoromethyl)imidazo[1,2-a]pyrazin-6-yl]benzamide;
2-fluoro-N-(2-methylimidazo[1,2-a]pyrazin-6-yl)-4-piperazin-1-ylbenzamide;
4-[(8aS)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
2-ethoxy-N-(2-methylimidazo[1,2-a]pyrazin-6-yl)-4-[(3S)-3-methylpiperazin-1-yl]benzamide;
2-ethoxy-N-(2-methylimidazo[1,2-a]pyrazin-6-yl)-4-[(3R)-3-methylpiperazin-1-yl]benzamide;
4-[(8aR)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
4-[(8aR)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
4-[(8aS)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
4-(1,4-diazepan-1-yl)-2-ethoxy-N-(2-methylimidazo[1,2-a]pyrazin-6-yl)benzamide;
4-[(3S,5R)-3,5-dimethylpiperazin-1-yl]-2-ethoxy-N-(2-methylimidazo[1,2-a]pyrazin-6-yl)benzamide;
2-fluoro-N-(2-methylimidazo[1,2-a]pyrazin-6-yl)-4-[(3S)-3-pyrrolidin-1-ylpyrrolidin-1-yl]benzamide;
2-fluoro-N-(2-methylimidazo[1,2-a]pyrazin-6-yl)-4-[(3R)-3-methylpiperazin-1-yl]benzamide;
2-chloro-6-fluoro-N-(2-methylimidazo[1,2-a]pyrazin-6-yl)-4-piperazin-1-ylbenzamide;
2,5-difluoro-N-(2-methylimidazo[1,2-a]pyrazin-6-yl)-4-(3-methylpiperazin-1-yl)benzamide;
2,3-difluoro-N-(2-methylimidazo[1,2-a]pyrazin-6-yl)-4-(3-methylpiperazin-1-yl)benzamide;
4-[(3R,5S)-3,5-dimethylpiperazin-1-yl]-2-methoxy-N-(2-methylimidazo[1,2-a]pyrazin-6-yl)benzamide;
4-(4,7-diazaspiro[2.5]octan-7-yl)-2-methoxy-N-(2-methylimidazo[1,2-a]pyrazin-6-yl)benzamide;
4-(3,3-dimethylpiperazin-1-yl)-2-fluoro-N-(2-methylimidazo[1,2-a]pyrazin-6-yl)benzamide;
2-methoxy-N-(2-methylimidazo[1,2-a]pyrazin-6-yl)-4-[(3R)-3-methylpiperazin-1-yl]benzamide;
2-methoxy-N-(2-methylimidazo[1,2-a]pyrazin-6-yl)-4-[(3R)-3-pyrrolidin-1-ylpyrrolidin-1-yl]benzamide;

4-[(3R)-3-ethylpiperazin-1-yl]-2-methoxy-N-(2-methylimidazo[1,2-a]pyrazin-6-yl)benzamide;
4-(3,3-dimethylpiperazin-1-yl)-2-methoxy-N-(2-methylimidazo[1,2-a]pyrazin-6-yl)benzamide;
N-[8-(difluoromethyl)-2-methylimidazo[1,2-a]pyrazin-6-yl]-2-fluoro-4-[(3R)-3-methylpiperazin-1-yl]benzamide;
2-fluoro-N-(2-methylimidazo[1,2-a]pyrazin-6-yl)-4-(3-propan-2-ylpiperazin-1-yl)benzamide;
6-[(3R)-3-ethylpiperazin-1-yl]-2-methoxy-N-(2-methylimidazo[1,2-a]pyrazin-6-yl)pyridine-3-carboxamide;
2-methoxy-N-(2-methylimidazo[1,2-a]pyrazin-6-yl)-6-piperazin-1-ylpyridine-3-carboxamide; and pharmaceutically acceptable salts thereof.

Particular compounds of formula (I) of the present invention are those selected from the group consisting of:
4-(4,7-diazaspiro[2.5]octan-7-yl)-2-fluoro-N-(2-methylimidazo[1,2-a]pyrazin-6-yl)benzamide;
4-[(3S,5R)-3,5-dimethylpiperazin-1-yl]-2-fluoro-N-(2-methylimidazo[1,2-a]pyrazin-6-yl)benzamide;
4-[(3R)-3-ethylpiperazin-1-yl]-2-fluoro-N-(2-methylimidazo[1,2-a]pyrazin-6-yl)benzamide;
2-fluoro-N-(2-methylimidazo[1,2-a]pyrazin-6-yl)-4-[(3R)-3-pyrrolidin-1-ylpyrrolidin-1-yl]benzamide;
4-[(3S)-3-ethylpiperazin-1-yl]-2-fluoro-N-(2-methylimidazo[1,2-a]pyrazin-6-yl)benzamide;
2-fluoro-4-[(3R)-3-methylpiperazin-1-yl]-N-[2-methyl-8-(trifluoromethyl)imidazo[1,2-a]pyrazin-6-yl]benzamide;
and pharmaceutically acceptable salts thereof.

Compounds of formula (VIII) are suitable as intermediates in the manufacture of compounds of formula (I).

Another embodiment of the invention relates to compounds of formula (VIII)

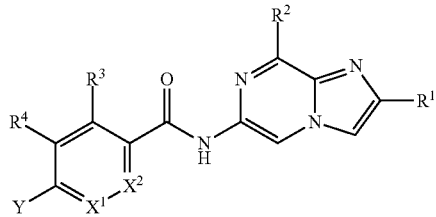

(VIII)

wherein $X^1$, $X^2$, $R^1$, $R^2$, $R^3$ and $R^4$ are as described herein;
Y is halogen or trifluoromethanesulfonate;
or salts thereof.

A particular embodiment of the present invention relates to compounds of formula (VIII), wherein Y is fluoro, chloro, bromo, iodo or trifluoromethanesulfonate, particularly bromo.

Particular compounds of formula (VIII) of the present invention are those selected from the group consisting of:
4-Bromo-2-fluoro-N-(2-methylimidazo[1,2-a]pyrazin-6-yl)benzamide;
4-Bromo-N-(2-methylimidazo[1,2-a]pyrazin-6-yl)benzamide; and
4-Bromo-2-ethoxy-N-(2-methylimidazo[1,2-a]pyrazin-6-yl)benzamide.

Manufacturing Processes

Compounds of formula (I) or pharmaceutically acceptable salts thereof as defined above can be prepared following standard methods known in the art.

As illustrated in Scheme 1, the compound of formula (III) can be obtained by a Buchwald-Hartwig amination reaction between a compound of formula (II) and a secondary amine of formula A-H in the presence of a catalyst (e.g. tris(dibenzylidene-acetone)dipalladium(0) ($Pd_2(dba)_3$)) and a ligand (e.g. 2,2'-bis(diphenylphosphino)-1,1'-binaphthyl) and a base (e.g. cesium carbonate) and a solvent (e.g. toluene), wherein A, $X^1$, $X^2$, $R^3$ and $R^4$ as described herein and $R^{18}$ is $C_{1-7}$-alkyl. After an ester hydrolysis to form the acid derivative (IV) in the presence of an aqueous base (e.g. LiOH, NaOH and the like), the conversion into a primary amide (e.g. with CDI and aqueous ammonium hydroxide) provides compounds of formula (V). Finally, a Buchwald-Hartwig amidation reaction of the compound of formula (V) with compounds of formula (VI) in the presence of a catalyst (e.g. tris(dibenzylidene-acetone)dipalladium(0) ($Pd_2(dba)_3$)), a ligand (e.g. (diphenylphosphino)-9,9-dimethylxanthene), a base (e.g. cesium carbonate) and a solvent (e.g. dioxane) at elevated temperature (e.g. 100° C.) provides the final compound of formula (I), wherein $R^1$ and $R^2$ as described herein.

In case the N-heterocycloalkyl A of formula A-H comprises additional primary or secondary amino-groups, such additional primary or secondary amino-groups are protected using suitable amino-protecting groups (such as Boc or CBZ) and an additional deprotection step (e.g. using HCl in dioxane) is required after the Buchwald-Hartwig amidation reaction of the compound of formula (V) with the compound of formula (VI) to obtain the final product of compound of formula (I).

SCHEME 1.

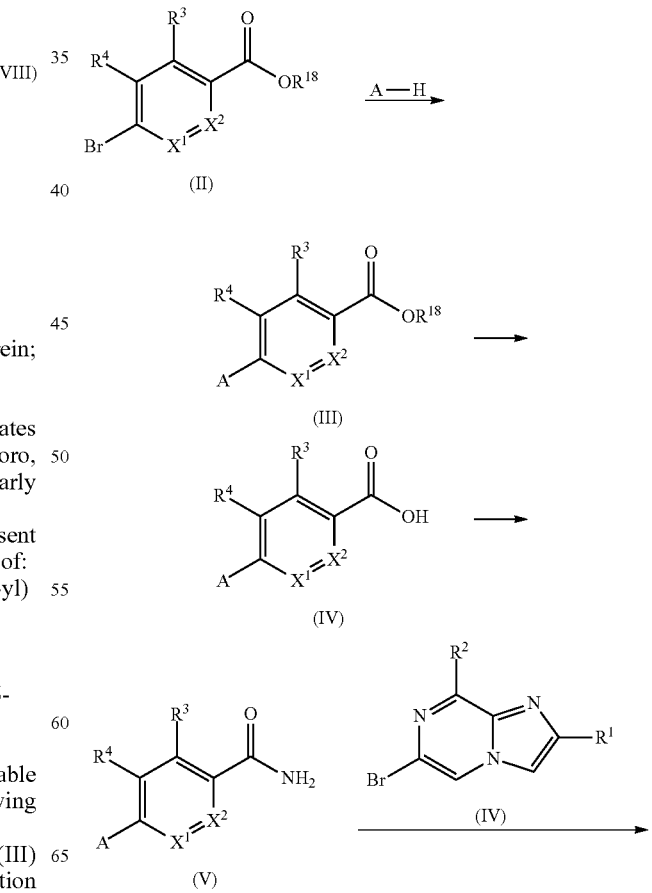

-continued

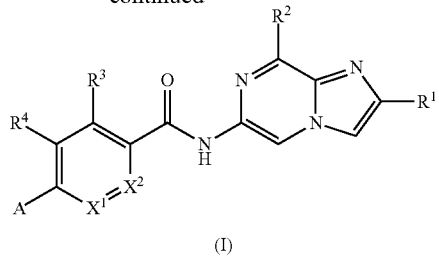

(I)

In one embodiment, the invention relates to a process for the manufacture of compounds of formula (I) or pharmaceutically acceptable salts thereof as defined above, comprising the reaction of a compound of formula (V) with a compound of formula (VI) in the presence of a catalyst (e.g. tris(dibenzylidene-acetone)dipalladium(0) (Pd$_2$(dba)$_3$)), a ligand (e.g. (diphenylphosphino)-9,9-dimethylxanthene), a base (e.g. cesium carbonate) and a solvent (e.g. dioxane) at elevated temperature (e.g. 100° C.), wherein A, X$^1$, X$^2$, R$^1$, R$^2$, R$^3$ and R$^4$ as described herein.

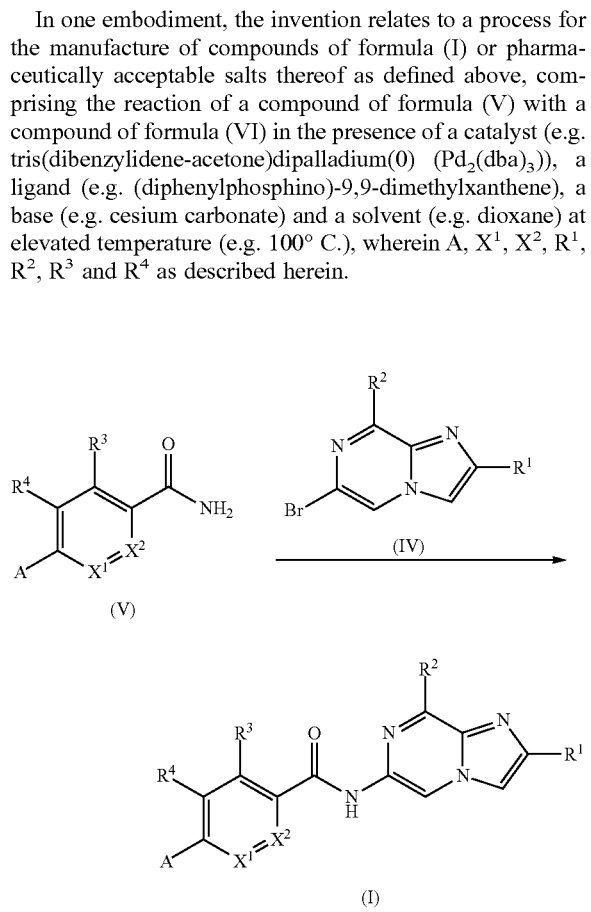

Alternatively, compounds of formula (I) can be prepared as illustrated in Scheme 2 via a coupling reaction of a compound of formula (VII) with derivatives of formula (VI) in the presence of a catalyst (e.g. copper (I) iodide), a ligand (e.g. (1,10-phenantroline), a base (e.g. K$_3$PO$_4$) and a solvent (e.g. dioxane) at elevated temperature (e.g. 120° C.) to provide compounds of formula (VIII), wherein X$^1$, X$^2$, Y, R$^1$, R$^2$, R$^3$ and R$^4$ are as described herein.

Finally, the compound of formula (VIII) is reacted with a compound M-A either in:
  a) an aromatic nucleophilic substitution reaction (particularly if Y is fluoro or if Y is chloro and X$^1$ is Nitrogen) by heating at a temperature from 80° C. to 200° C. in a solvent (e.g. dimethyl sulfoxide (DMSO), N-methylpyrrolidone (NMP), or dimethylformamide (DMF)); or
  b) a Buchwald-Hartwig amination reaction in the presence of a catalyst (e.g. tris(dibenzylidene-acetone)di-palladium(0) (Pd$_2$(dba)$_3$)) a ligand (e.g. 2,2'-bis(diphenylphosphino)-1,1'-binaphthyl), a base (e.g. cesium carbonate) by heating at a temperature from 20° C. to 100° C. in a solvent (e.g. toluene);

to give a compound of formula (I), wherein A is as defined herein, M is hydrogen, sodium or potassium, particularly hydrogen, and wherein M is linked to A via a nitrogen atom of A.

SCHEME 2.

In one embodiment, the invention relates to a process for the manufacture of compounds of formula (I) or pharmaceutically acceptable salts thereof as defined above, comprising the reaction of a compound of formula (VIII) with a compound M-A either in:
  a) an aromatic nucleophilic substitution reaction (particularly if Y is fluoro or if Y is chloro and X$^1$ is Nitrogen) by heating at a temperature from 80° C. to 200° C. in a solvent (particularly dimethyl sulfoxide (DMSO), N-methylpyrrolidone (NMP), or dimethylformamide (DMF)); or
  b) a Buchwald-Hartwig amination reaction in the presence of a catalyst (particularly tris(dibenzylidene-acetone)dipalladium(0) (Pd$_2$(dba)$_3$)) a ligand (particularly 2,2'-bis(diphenylphosphino)-1,1'-binaphthyl), a base (particularly cesium carbonate) by heating at a temperature from 20° C. to 100° C. in a solvent (particularly toluene);

wherein A, X$^1$, X$^2$, Y, R$^1$, R$^2$, R$^3$ and R$^4$ are as defined herein, M is hydrogen, sodium or potassium, particularly hydrogen, and wherein M is linked to A via a nitrogen atom of A.

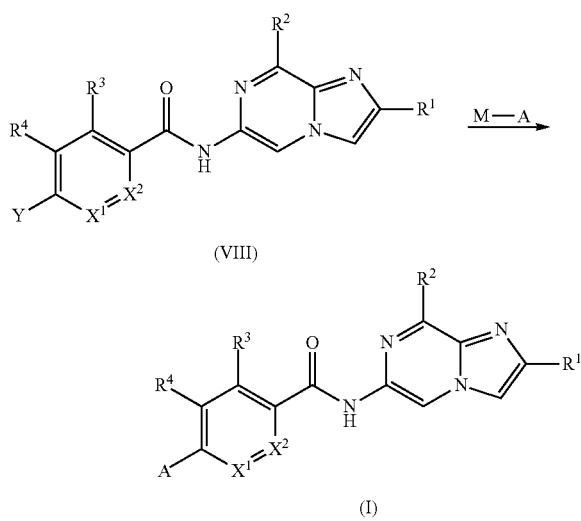

Particularly, compounds of formula (I) or pharmaceutically acceptable salts thereof can be prepared in accordance to the methods described in the examples herein.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Uses

As described above, the compounds of formula (I) and their pharmaceutically acceptable salts possess valuable pharmacological properties and have been found to enhance inclusion of exon 7 of SMN1 and/or SMN2 into mRNA transcribed from the SMN1 and/or SMN2 gene, thereby increasing expression of SMN protein in a human subject in need thereof.

The compounds of the present invention can be used, either alone or in combination with other drugs, for the treatment or prevention of diseases caused by an inactivating mutation or deletion in the SMN1 gene and/or associated with loss or defect of SMN1 gene function. These diseases include, but are not limited to spinal muscular atrophy (SMA).

A particular embodiment of the present invention relates to pharmaceutical compositions comprising compounds of formula (I) as defined above or their pharmaceutically acceptable salts as defined above and one or more pharmaceutically acceptable excipients.

A particular embodiment of the present invention relates to pharmaceutical compositions comprising compounds of formula (I) or their pharmaceutically acceptable salts as defined above and one or more pharmaceutically acceptable excipients for the treatment or prevention of diseases caused by an inactivating mutation or deletion in the SMN1 gene and/or associated with loss or defect of SMN1 gene function, particularly for the treatment or prevention of SMA.

A particular embodiment of the present invention relates to compounds of formula (I) or their pharmaceutically acceptable salts as defined above for use as therapeutically active substances, especially for use as therapeutically active substances for the treatment or prevention of diseases caused by an inactivating mutation or deletion in the SMN1 gene and/or associated with loss or defect of SMN1 gene function, particularly for the treatment or prevention of spinal muscular atrophy (SMA).

A particular embodiment of the present invention relates to compounds of formula (I) or their pharmaceutically acceptable salts as defined above for the use in the treatment or prevention of diseases caused by an inactivating mutation or deletion in the SMN1 gene and/or associated with loss or defect of SMN1 gene function, particularly for use in the treatment or prevention of spinal muscular atrophy (SMA).

A particular embodiment of the present invention relates to a method for the treatment or prevention of diseases caused by an inactivating mutation or deletion in the SMN1 gene and/or associated with loss or defect of SMN1 gene function, particularly for the treatment or prevention of spinal muscular atrophy (SMA), which method comprises administering compounds of formula (I) or their pharmaceutically acceptable salts as defined above to a subject.

A particular embodiment of the present invention relates to the use of compounds of formula (I) or their pharmaceutically acceptable salts as defined above for the treatment or prevention of diseases caused by an inactivating mutation or deletion in the SMN1 gene and/or associated with loss or defect of SMN1 gene function, particularly for the treatment or prevention of spinal muscular atrophy (SMA).

A particular embodiment of the present invention relates to the use of compounds of formula (I) or their pharmaceutically acceptable salts as defined above for the preparation of medicaments for the treatment or prevention of diseases caused by an inactivating mutation or deletion in the SMN1 gene and/or associated with loss or defect of SMN1 gene function, particularly for the treatment or prevention of spinal muscular atrophy (SMA). Such medicaments comprise compounds of formula (I) or their pharmaceutically acceptable salts as defined above.

EXAMPLES

The invention will be more fully understood by reference to the following examples. They should however not be construed as limiting the scope of the invention.

Abbreviations Used

ACN: acetonitrile; Boc: tert-butyloxycarbonyl; $B_2(pin)_2$: bis(pinacolato)diboron; CBZ: benzyloxycarbonyl; CDI: 1,1'-carbonyldiimidazole; $CH_2Cl_2$: dichloromethane; dba: dibenzylideneacetone; DIPEA: diisopropyl ethylamine; DMA: dimethyl acetamide; DMF: dimethylformamide; DMSO: dimethyl sulfoxide; NMP: N-methylpyrrolidone; $Pd_2(dba)_3$: tris(dibenzylidene-acetone)dipalladium(0); $Pd(dppf)Cl_2$: (1,1'-bis(diphenylphosphino)ferrocene)palladium(II) dichloride; PPTS: pyridinium p-toluenesulfonate; TEA: triethylamine; RT: room temperature; Xantphos: diphenylphosphino)-9, 9-dimethylxanthene.

Intermediate A.1

Preparation of tert-butyl (2R)-4-(3-fluoro-4-methoxycarbonylphenyl)-2-methylpiperazine-1-carboxylate

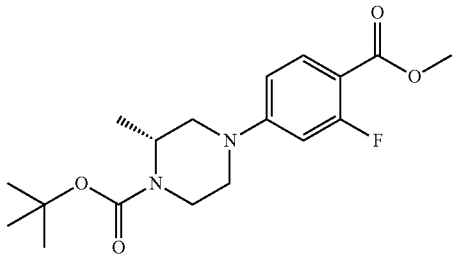 [SMILES: COC(=O)c1ccc(N2CCN(C(=O)OC(C)(C)C)[C@H](C)C2)cc1F]

To a mixture of methyl 4-bromo-2-fluorobenzoate (1.10 g, 4.7 mmol), (R)-tert-butyl 2-methylpiperazine-1-carboxylate (1.04 g, 5.2 mmol), cesium carbonate (2.31 g, 7.1 mmol) in toluene (11 ml) was added tris(dibenzylideneacetone)dipalladium(0) (0.13 g, 0.1 mmol) and (rac)-2,2'-bis(diphenylphosphino)-1,1'-binaphthalene (0.27 g, 0.4 mmol) under argon and the mixture heated to 100° C. in a sealed tube for 20 h. The reaction was then diluted with EtOAc, washed with water, brine, dried ($Na_2SO_4$) and concentrated. Purification by flash column chromatography on silica gel (EtOAc: Hept 0:1-4:6) afforded the titled product as a yellow solid (0.99 g, 60%). MS (m/e): 352.0 (M+H$^+$)

In analogy to Intermediate A.1, Intermediates A.2 to A.23 of the following table were prepared from the corresponding amine and aryl bromide.

| Intermediate No. | Structure | Systematic Name | Starting materials |
|---|---|---|---|
| A.2 | 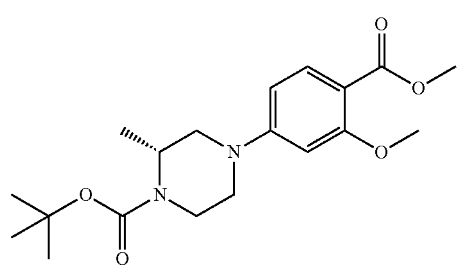 [SMILES: COC(=O)c1ccc(N2CCN(C(=O)OC(C)(C)C)[C@H](C)C2)cc1OC] | tert-butyl (2R)-4-(3-methoxy-4-methoxycarbonylphenyl)-2-methylpiperazine-1-carboxylate | (R)-tert-butyl 2-methylpiperazine-1-carboxylate and methyl 4-bromo-2-methoxybenzoate |

-continued

| Intermediate No. | Structure | Systematic Name | Starting materials |
|---|---|---|---|
| A.3 | 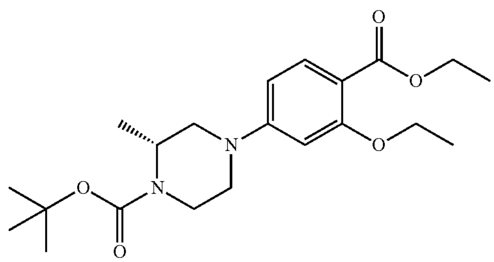 [SMILES: CCOC(=O)c1ccc(N2CCN(C(=O)OC(C)(C)C)[C@H](C)C2)cc1OCC] | tert-butyl (2R)-4-(3-ethoxy-4-ethoxycarbonyl-phenyl)-2-methylpiperazine-1-carboxylate | (R)-tert-butyl 2-methylpiperazine-1-carboxylate and ethyl 4-bromo-2-ethoxybenzoate |
| A.4 | 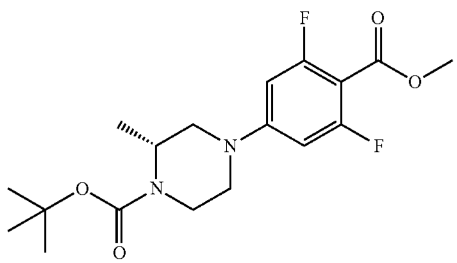 [SMILES: COC(=O)c1c(F)cc(N2CCN(C(=O)OC(C)(C)C)[C@H](C)C2)cc1F] | tert-butyl (2R)-4-(3,5-difluoro-4-methoxycarbonyl-phenyl)-2-methylpiperazine-1-carboxylate | (R)-tert-butyl 2-methylpiperazine-1-carboxylate and methyl 4-bromo-2,6-difluorobenzoate |
| A.5 | 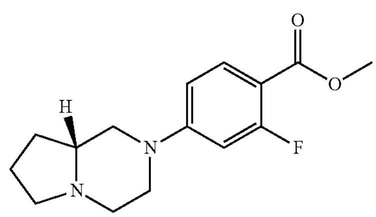 [SMILES: COC(=O)c1ccc(N2CCN3CCC[C@@H]3C2)cc1F] | tert-butyl (2R)-4-(3-ethoxy-4-ethoxycarbonyl-phenyl)-2-methylpiperazine-1-carboxylate | (R)-octahydropyrrolo[1,2-a]pyrazine and methyl 4-bromo-2-fluorobenzoate |
| A.6 | 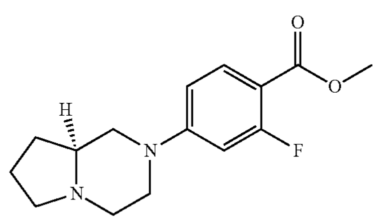 [SMILES: COC(=O)c1ccc(N2CCN3CCC[C@H]3C2)cc1F] | methyl 4-[(8aS)-3,4,6,7,8,8a-hexahydro-1H-pyrrolo[1,2-a]pyrazin-2-yl]-2-fluorobenzoate | (S)-octahydropyrrolo[1,2-a]pyrazine and methyl 4-bromo-2-fluorobenzoate |
| A.7 | 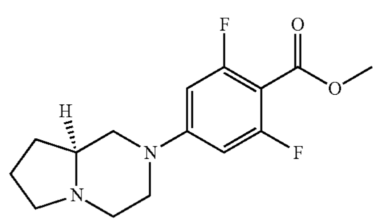 [SMILES: COC(=O)c1c(F)cc(N2CCN3CCC[C@H]3C2)cc1F] | methyl 4-[(8aS)-3,4,6,7,8,8a-hexahydro-1H-pyrrolo[1,2-a]pyrazin-2-yl]-2,6-difluoro-benzoate | (S)-octahydro-pyrrolo[1,2-a]pyrazine and methyl 4-bromo-2,6-difluorobenzoate |
| A.8 | 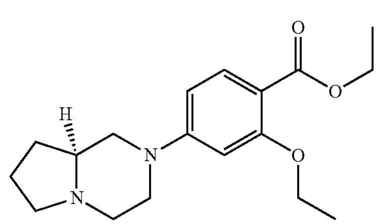 [SMILES: CCOC(=O)c1ccc(N2CCN3CCC[C@H]3C2)cc1OCC] | ethyl 4-[(8aS)-3,4,6,7,8,8a-hexahydro-1H-pyrrolo[1,2-a]pyrazin-2-yl]-2-ethoxybenzoate | (S)-octahydro-pyrrolo[1,2-a]pyrazine and ethyl 4-bromo-2-ethoxybenzoate |

-continued

| Intermediate No. | Structure | Systematic Name | Starting materials |
|---|---|---|---|
| A.9 | 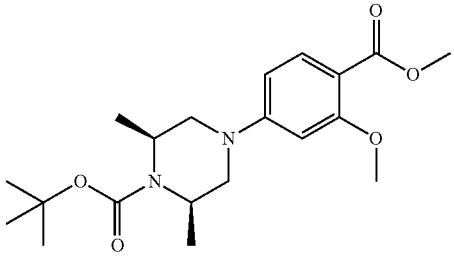 [SMILES: COC(=O)c1ccc(N2C[C@@H](C)N(C(=O)OC(C)(C)C)[C@@H](C)C2)cc1OC] | benzyl (2R,6S)-4-(3-fluoro-4-methoxycarbonyl-phenyl)-2,6-dimethyl-piperazine-1-carboxylate | (cis)-tert-butyl 2,6-dimethyl-piperazine-1-carboxylate and methyl 4-bromo-2-methoxybenzoate |
| A.10 | 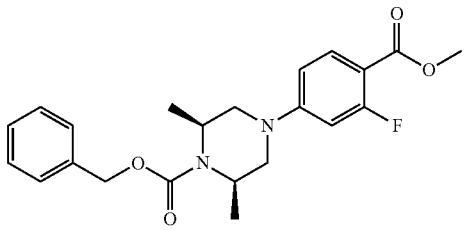 [SMILES: COC(=O)c1ccc(N2C[C@@H](C)N(C(=O)OCc3ccccc3)[C@@H](C)C2)cc1F] | benzyl (2R,6S)-4-(3-fluoro-4-methoxycarbonyl-phenyl)-2,6-dimethyl-piperazine-1-carboxylate | (cis)-benzyl 2,6-dimethyl-piperazine-1-carboxylate and methyl 4-bromo-2-fluorobenzoate |
| A.11 | 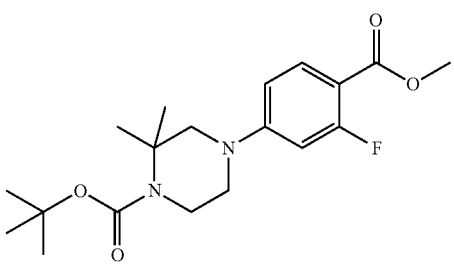 [SMILES: COC(=O)c1ccc(N2CCN(C(=O)OC(C)(C)C)C(C)(C)C2)cc1F] | tert-butyl 4-(3-fluoro-4-methoxycarbonyl-phenyl)-2,2-dimethyl-piperazine-1-carboxylate | tert-butyl 2,2-dimethyl-piperazine-1-carboxylate and methyl 4-bromo-2-fluorobenzoate |
| A.12 | 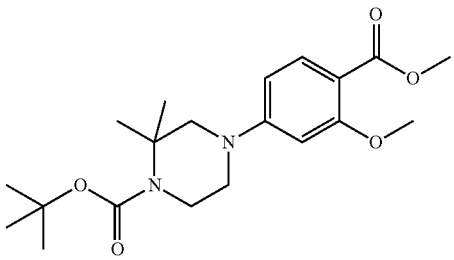 [SMILES: COC(=O)c1ccc(N2CCN(C(=O)OC(C)(C)C)C(C)(C)C2)cc1OC] | tert-butyl 4-(3-methoxy-4-methoxycarbonyl-phenyl)-2,2-dimethyl-piperazine-1-carboxylate | tert-butyl 2,2-dimethyl-piperazine-1-carboxylate and methyl 4-bromo-2-methoxybenzoate |
| A.13 | 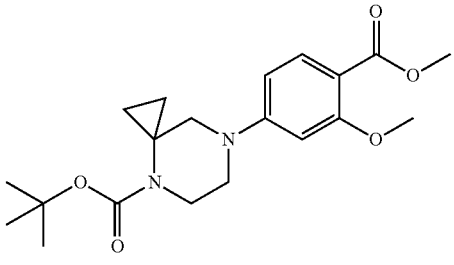 [SMILES: COC(=O)c1ccc(N2CCN(C(=O)OC(C)(C)C)C3(CC3)C2)cc1OC] | tert-butyl 7-(3-methoxy-4-methoxycarbonyl-phenyl)-4,7-diazaspiro[2.5]octane-4-carboxylate | tert-butyl 4,7-diazaspiro[2.5]octane-4-carboxylate and methyl 4-bromo-2-methoxybenzoate |
| A.14 | 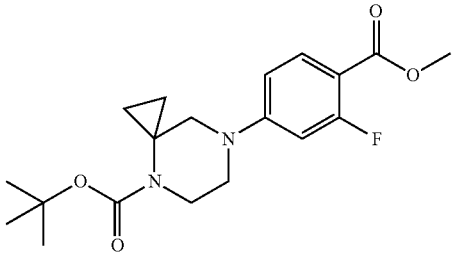 [SMILES: COC(=O)c1ccc(N2CCN(C(=O)OC(C)(C)C)C3(CC3)C2)cc1F] | tert-butyl 7-(3-fluoro-4-methoxycarbonyl-phenyl)-4,7-diazaspiro[2.5]octane-4-carboxylate | tert-butyl 4,7-diazaspiro[2.5]octane-4-carboxylate and methyl 4-bromo-2-fluorobenzoate |

-continued

| Intermediate No. | Structure | Systematic Name | Starting materials |
|---|---|---|---|
| A.15 | 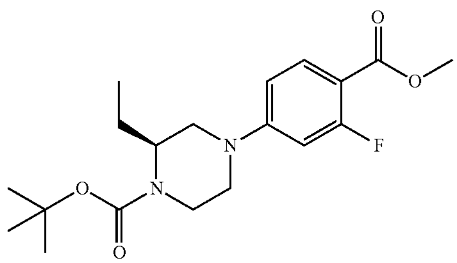 [SMILES: CC[C@H]1CN(c2ccc(C(=O)OC)c(F)c2)CCN1C(=O)OC(C)(C)C] | tert-butyl (2S)-2-ethyl-4-(3-fluoro-4-methoxy-carbonylphenyl)piperazine-1-carboxylate | (S)-tert-butyl 2-ethylpiperazine-1-carboxylate and methyl 4-bromo-2-fluorobenzoate |
| A.16 | 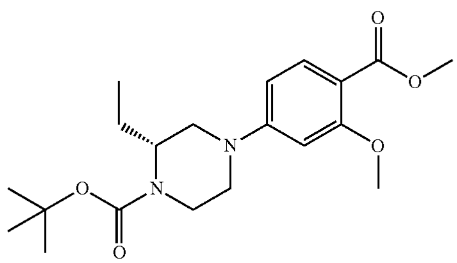 [SMILES: CC[C@@H]1CN(c2ccc(C(=O)OC)c(OC)c2)CCN1C(=O)OC(C)(C)C] | tert-butyl (2R)-2-ethyl-4-(3-fluoro-4-methoxy-carbonylphenyl)piperazine-1-carboxylate | (R)-tert-butyl 2-ethylpiperazine-1-carboxylate and methyl 4-bromo-2-methoxy-benzoate |
| A.17 | 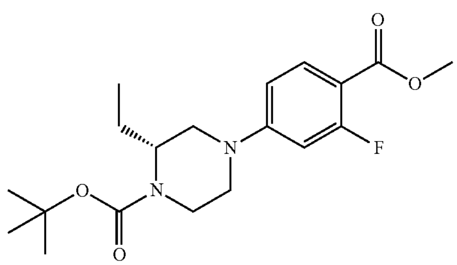 [SMILES: CC[C@@H]1CN(c2ccc(C(=O)OC)c(F)c2)CCN1C(=O)OC(C)(C)C] | tert-butyl (2R)-2-ethyl-4-(3-fluoro-4-methoxy-carbonylphenyl)piperazine-1-carboxylate | (R)-tert-butyl 2-ethylpiperazine-1-carboxylate and methyl 4-bromo-2-fluorobenzoate |
| A.18 | 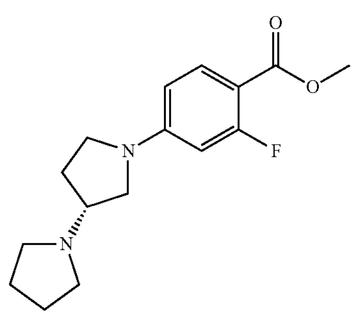 [SMILES: COC(=O)c1ccc(N2CC[C@@H](N3CCCC3)C2)cc1F] | methyl 2-fluoro-4-[(3R)-3-pyrrolidin-1-ylpyrrolidin-1-yl]benzoate | (R)-1,3'-bipyrrolidine dihydrochloride and methyl 4-bromo-2-fluorobenzoate |
| A.19 | 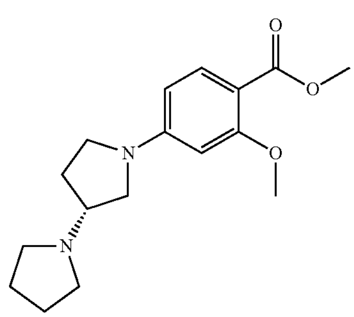 [SMILES: COC(=O)c1ccc(N2CC[C@@H](N3CCCC3)C2)cc1OC] | methyl 2-methoxy-4-[(3R)-3-pyrrolidin-1-ylpyrrolidin-1-yl]benzoate | R)-1,3'-bipyrrolidine dihydrochloride and methyl 4-bromo-2-methoxy-benzoate |

| Intermediate No. | Structure | Systematic Name | Starting materials |
|---|---|---|---|
| A.20 | 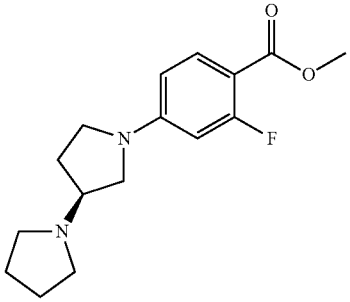 [SMILES: COC(=O)c1ccc(N2CC[C@H](N3CCCC3)C2)cc1F] | methyl 2-methoxy-4-[(3R)-3-pyrrolidin-1-ylpyrrolidin-1-yl]benzoate | (S)-1,3'-bipyrrolidine dihydrochloride and methyl 4-bromo-2-fluorobenzoate |
| A.22 | 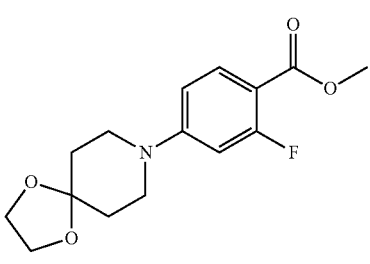 [SMILES: COC(=O)c1ccc(N2CCC3(CC2)OCCO3)cc1F] | methyl 4-(1,4-dioxa-8-azaspiro[4.5]decan-8-yl)-2-fluorobenzoate | 1,4-dioxa-8-azaspiro[4.5]decane and methyl 4-bromo-2-fluorobenzoate |
| A.23 | 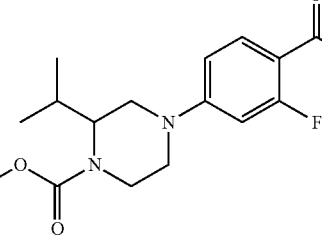 | tert-butyl 4-(3-fluoro-4-methoxycarbonylphenyl)-2-propan-2-ylpiperazine-1-carboxylate | tert-butyl 2-isopropyl-piperazine-1-carboxylate and methyl 4-bromo-2-fluorobenzoate |

Intermediate A.24

Preparation of tert-butyl 4-(2,5-difluoro-4-methoxycarbonylphenyl)-2-methylpiperazine-1-carboxylate

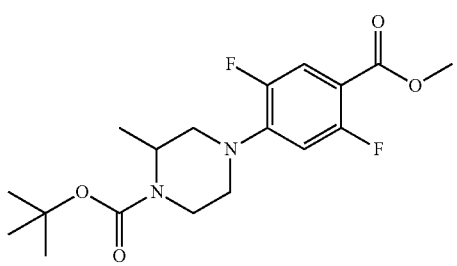 [SMILES: COC(=O)c1cc(F)c(N2CCN(C(=O)OC(C)(C)C)C(C)C2)cc1F]

Step A:
A stirred solution of methyl 2,4,5-trifluorobenzoate (1.393 g, 7.33 mmol, Eq: 1.00) and 2-methylpiperazine (2.23 g, 21.8 mmol, Eq: 2.98) in DMA (5 ml) was heated at 100° C. in a microwave reactor for 15 min. The solvent was evaporated under vacuo and the residue dissolved in $CH_2Cl_2$ and washed with $H_2O$. The organic phase was dried over $Na_2SO_4$ and concentrated in vacuo.

Step B:
The crude mixture was dissolved in $CH_2Cl_2$ (10 mL) and triethylamine was added (1.23 mL, 8.79 mmol, Eq: 1.2). The solution was cooled to 0° C. and a solution of di-tert-butyl dicarbonate (2.41 g, 10.9 mmol, Eq: 1.49) in $CH_2Cl_2$ (3.75 ml) was added dropwise. The reaction mixture was stirred at room temperature for 18 h. Water was added to the reaction and the layers were separated. The organic phase was dried over $Na_2SO_4$, and purification by column chromatography ($SiO_2$, Heptane/EtOAc) provided the title compound as a white solid (1.77 g, 65%). MS (m/e): 371.1 (M+H$^+$).

Intermediate A.25

Preparation of tert-butyl 4-(4-ethoxycarbonyl-2,3-difluorophenyl)-2-methylpiperazine-1-carboxylate

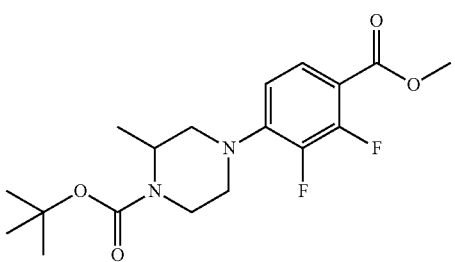 [SMILES: COC(=O)c1ccc(N2CCN(C(=O)OC(C)(C)C)C(C)C2)c(F)c1F]

Step A:

A solution of ethyl 2,3,4-trifluorobenzoate (1.51 g, 7.4 mmol, Eq: 1.00) and 2-methylpiperazine (2.27 g, 22.2 mmol, Eq: 3) in DMA (5 ml) was heated at 100° C. in a microwave reactor for 15 min. The solvent was evaporated in vacuo. EtOAc and an aqueous solution of NaHCO$_3$ were added to the residue. The layers were separated and the aqueous layer was back-extracted twice with CH$_2$Cl$_2$. The combined organic phases were dried over Na$_2$SO$_4$, filtered and concentrated in vacuo to give 2.15 g of yellow oil.

Step B:

This crude oil was dissolved in CH$_2$Cl$_2$ (10 ml) and triethylamine (1.24 ml, 8.88 mmol, Eq: 1.2) was added. The solution was cooled to 0° C. and a solution of di-tert-butyl dicarbonate (2.45 g, 11.1 mmol, Eq: 1.5) in CH$_2$Cl$_2$ (3.75 ml) was added dropwise. The reaction mixture was stirred at room temperature for 18 h. Water was added to the reaction and the layers were separated. The aqueous layer was back-extracted twice with CH$_2$Cl$_2$. The combined organic layers were dried over Na$_2$SO$_4$, filtered and concentrated in vacuo. The product was purified by flash column chromatography (SiO$_2$, Heptane/EtOAc), which allowed the separation of two regioisomers, the second compound to elute being the desired title derivative obtained as a light yellow oil (1.54 g, 54%). MS (m/e): 385.3 (M+H$^+$).

Intermediate B.1

Preparation of tert-butyl (2R)-4-(4-carbamoyl-3-fluorophenyl)-2-methylpiperazine-1-carboxylate

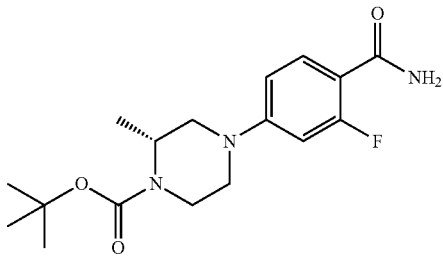 [SMILES: C[C@@H]1CN(c2ccc(C(N)=O)c(F)c2)CCN1C(=O)OC(C)(C)C]

To a solution of tert-butyl (2R)-4-(3-fluoro-4-methoxycarbonylphenyl)-2-methylpiperazine-1-carboxylate (0.95 g, 2.7 mmol, Intermediate A.1) in MeOH (6 ml) was added sodium hydroxide (1.4 ml, 6M in water, 6.1 mmol) and the reacted heated to 55° C. for 7 h. The reaction was then acidified by addition of IR120$^+$ resin, filtered and concentrated to afford crude (R)-4-(4-(tert-butoxycarbonyl)-3-methylpiperazin-1-yl)-2-fluorobenzoic acid (0.82 g, 90%) as a white powder. The crude acid was then redissolved in DMF (6 ml) and 1,1'-carbonyldiimidazole (0.51 g, 3.2 mmol) added and the mixture stirred for 1 h before addition of ammonium hydroxide (1.3 ml, 25% aqueous, 8.4 mmol). After 0.5 h the reaction was poured into water, extracted with EtOAc, the combined organic layers were washed with brine, dried (Na$_2$SO$_4$) and concentrated to afford the title compound as a white solid (0.74 g, 90%). MS (m/e): 282.1 (M-tBu+H$^+$).

In analogy to Intermediate B.1, Intermediates B.2 to B.17 of the following table were prepared from the corresponding ester.

| Intermediate No. | Structure | Systematic Name | Starting materials |
|---|---|---|---|
| B.2 | 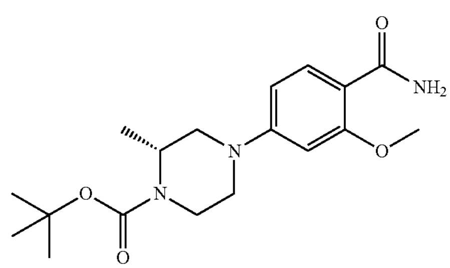 [SMILES: COc1cc(N2CCN(C(=O)OC(C)(C)C)[C@H](C)C2)ccc1C(N)=O] | tert-butyl (2R)-4-(4-carbamoyl-3-methoxyphenyl)-2-methyl-piperazine-1-carboxylate | A.2 |
| B.3 | 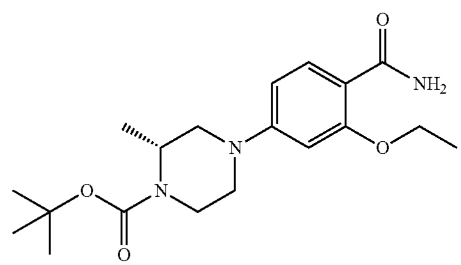 [SMILES: CCOc1cc(N2CCN(C(=O)OC(C)(C)C)[C@H](C)C2)ccc1C(N)=O] | tert-butyl (2R)-4-(4-carbamoyl-3-ethoxyphenyl)-2-methylpiperazine-1-carboxylate | A.3 |

-continued

| Intermediate No. | Structure | Systematic Name | Starting materials |
|---|---|---|---|
| B.4 | 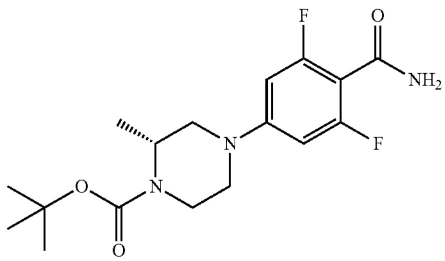 [SMILES: C[C@@H]1CN(c2cc(F)c(C(N)=O)c(F)c2)CCN1C(=O)OC(C)(C)C] | tert-butyl (2R)-4-(4-carbamoyl-3,5-difluorophenyl)-2-methylpiperazine-1-carboxylate | A.4 |
| B.5 | 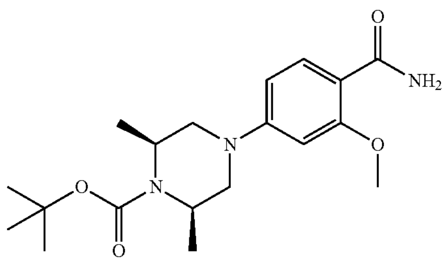 [SMILES: COc1cc(N2C[C@@H](C)N(C(=O)OC(C)(C)C)[C@@H](C)C2)ccc1C(N)=O] | tert-butyl (2S,6R)-4-(4-carbamoyl-3-methoxyphenyl)-2,6-dimethyl-piperazine-1-carboxylate | A.9 |
| B.6 | 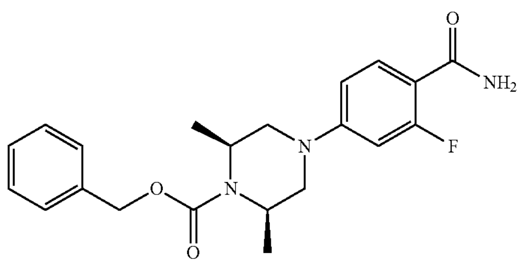 [SMILES: C[C@@H]1CN(c2ccc(C(N)=O)c(F)c2)C[C@H](C)N1C(=O)OCc1ccccc1] | benzyl (2R,6S)-4-(4-carbamoyl-3-fluorophenyl)-2,6-dimethyl-piperazine-1-carboxylate | A.10 |
| B.7 | 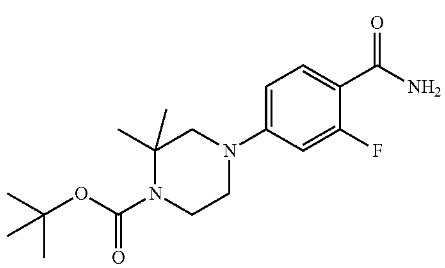 [SMILES: CC(C)(C)OC(=O)N1CCN(c2ccc(C(N)=O)c(F)c2)CC1(C)C] | tert-butyl 4-(4-carbamoyl-3-fluorophenyl)-2,2-dimethyl-piperazine-1-carboxylate | A.11 |
| B.8 | 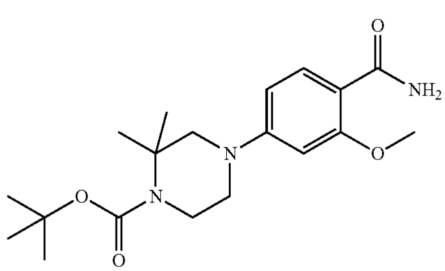 [SMILES: COc1cc(N2CCN(C(=O)OC(C)(C)C)C(C)(C)C2)ccc1C(N)=O] | tert-butyl 4-(4-carbamoyl-3-methoxyphenyl)-2,2-dimethyl-piperazine-1-carboxylate | A.12 |

-continued

| Intermediate No. | Structure | Systematic Name | Starting materials |
|---|---|---|---|
| B.9 | 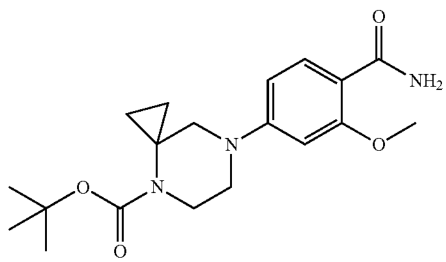 [SMILES: COc1cc(N2CCN(C(=O)OC(C)(C)C)C3(CC3)C2)ccc1C(N)=O] | tert-butyl 7-(4-carbamoyl-3-methoxyphenyl)-4,7-diazaspiro[2.5]octane-4-carboxylate | A.13 |
| B.10 | 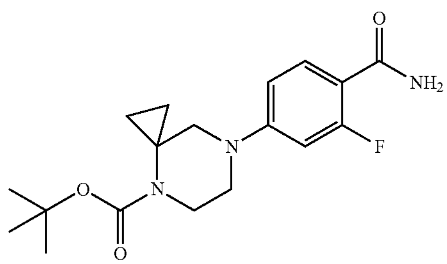 [SMILES: CC(C)(C)OC(=O)N1CCN(c2ccc(C(N)=O)c(F)c2)CC12CC2] | tert-butyl 7-(4-carbamoyl-3-fluorophenyl)-4,7-diazaspiro[2.5]octane-4-carboxylate | A.14 |
| B.11 | 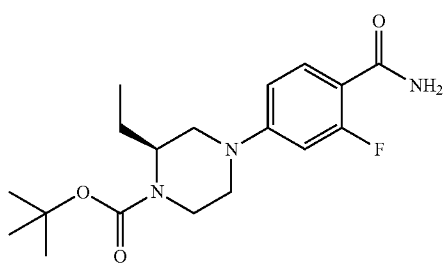 [SMILES: CC[C@H]1CN(c2ccc(C(N)=O)c(F)c2)CCN1C(=O)OC(C)(C)C] | tert-butyl (2S)-4-(4-carbamoyl-3-fluorophenyl)-2-ethylpiperazine-1-carboxylate | A.15 |
| B.12 | 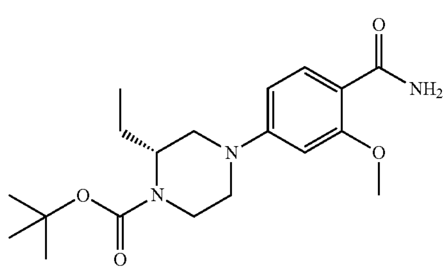 [SMILES: CC[C@@H]1CN(c2ccc(C(N)=O)c(OC)c2)CCN1C(=O)OC(C)(C)C] | tert-butyl (2R)-4-(4-carbamoyl-3-methoxyphenyl)-2-ethylpiperazine-1-carboxylate | A.16 |
| B.13 | 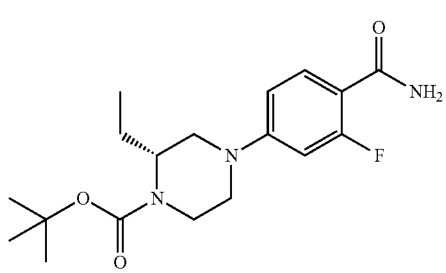 [SMILES: CC[C@@H]1CN(c2ccc(C(N)=O)c(F)c2)CCN1C(=O)OC(C)(C)C] | tert-butyl (2R)-4-(4-carbamoyl-3-fluorophenyl)-2-ethylpiperazine-1-carboxylate | A.17 |

| Intermediate No. | Structure | Systematic Name | Starting materials |
|---|---|---|---|
| B.14 | 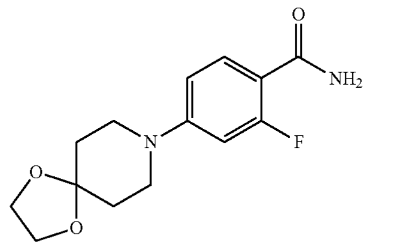 [SMILES: NC(=O)c1ccc(N2CCC3(CC2)OCCO3)cc1F] | 2-fluoro-4-(1,4-dioxa-8-azaspiro[4.5]decan-8-yl)benzamide | A.22 |
| B.15 | 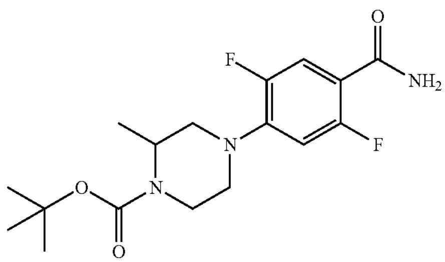 [SMILES: CC1CN(c2cc(F)c(C(N)=O)cc2F)CCN1C(=O)OC(C)(C)C] | tert-butyl 4-(4-carbamoyl-2,5-difluorophenyl)-2-methyl-piperazine-1-carboxylate | A.24 |
| B.16 | 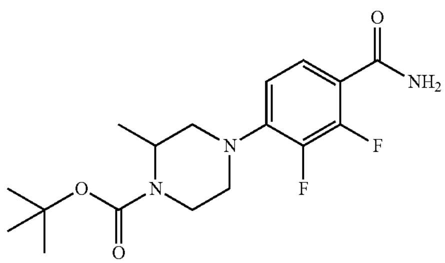 [SMILES: CC1CN(c2ccc(C(N)=O)c(F)c2F)CCN1C(=O)OC(C)(C)C] | tert-butyl 4-(4-carbamoyl-2,3-difluorophenyl)-2-methyl-piperazine-1-carboxylate | A.25 |
| B.17 | 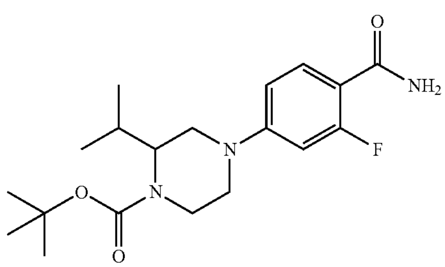 [SMILES: CC(C)C1CN(c2ccc(C(N)=O)c(F)c2)CCN1C(=O)OC(C)(C)C] | tert-butyl 4-(4-carbamoyl-3-fluorophenyl)-2-propan-2-yl-piperazine-1-carboxylate | A.23 |

Intermediate B.18

Preparation of 4-[(8aR)-3,4,6,7,8,8a-hexahydro-1H-pyrrolo[1,2-a]pyrazin-2-yl]-2-fluorobenzamide

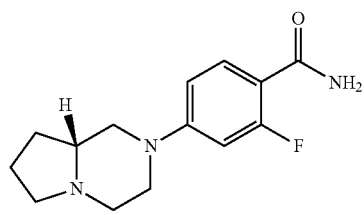 [SMILES: NC(=O)c1ccc(N2CCN3CCC[C@@H]3C2)cc1F]

To a solution of (R)-methyl 2-fluoro-4-(hexahydropyrrolo[1,2-a]pyrazin-2(1H)-yl)benzoate (0.12 g, 0.4 mmol, Intermediate A.5) in MeOH (2 ml) was added sodium hydroxide (0.1 ml, 6M in water, 0.6 mmol) and the reacted heated to 55° C. for 4 h. The reaction was then concentrated to afford crude (sodium (R)-2-fluoro-4-(hexahydropyrrolo[1,2-a]pyrazin-2(1H)-yl)benzoate which was then redissolved in DMF (2 ml) and N,N,N',N'-tetramethyl-O-(benzotriazol-1-yl)uronium tetrafluoroborate (0.17 g, 0.5 mmol) added and the mixture stirred for 1 h before addition of ammonium hydroxide (0.9 ml, 25% aqueous, 22.5 mmol). After 0.5 h the reaction was poured into water, extracted with EtOAc, the combined organic layers were washed with brine, dried (Na$_2$SO$_4$) and concentrated Purification by flash column chromatography on silica gel (DCM: MeOH 95:5-9:1) afforded the titled product as a white powder (0.2 g, quant.). MS (m/e): 264.2 (M+H$^+$)

In analogy to Intermediate B.18, Intermediates B.19 to B.24 of the following table were prepared from the corresponding ester.

| Intermediate No. | Structure | Systematic Name | Starting materials |
|---|---|---|---|
| B.19 | 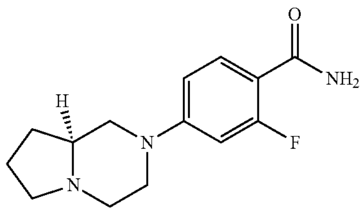 [SMILES: NC(=O)c1ccc(N2CCN3CCC[C@H]3C2)cc1F] | 4-[(8aS)-3,4,6,7,8,8a-hexahydro-1H-pyrrolo[1,2-a]pyrazin-2-yl]-2-fluorobenzamide | A.6 |
| B.20 | 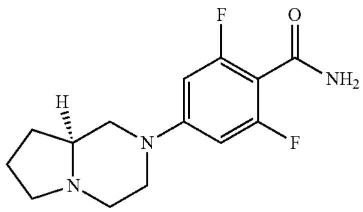 [SMILES: NC(=O)c1c(F)cc(N2CCN3CCC[C@H]3C2)cc1F] | 4-[(8aS)-3,4,6,7,8,8a-hexahydro-1H-pyrrolo[1,2-a]pyrazin-2-yl]-2,6-difluorobenzamide | A.7 |
| B.21 | 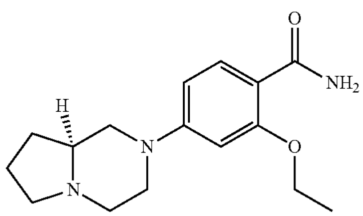 [SMILES: CCOc1cc(N2CCN3CCC[C@H]3C2)ccc1C(N)=O] | 4-[(8aS)-3,4,6,7,8,8a-hexahydro-1H-pyrrolo[1,2-a]pyrazin-2-yl]-2-ethoxybenzamide | A.8 |
| B.22 | 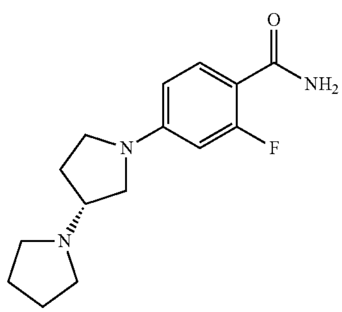 [SMILES: NC(=O)c1ccc(N2CC[C@@H](N3CCCC3)C2)cc1F] | 2-fluoro-4-[(3R)-3-pyrrolidin-1-ylpyrrolidin-1-yl]benzamide | A.18 |
| B.23 | 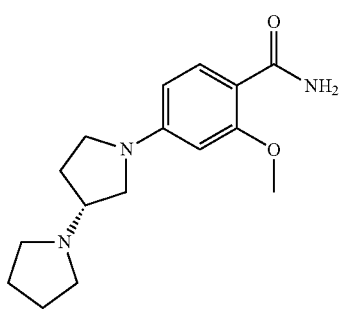 [SMILES: COc1cc(N2CC[C@@H](N3CCCC3)C2)ccc1C(N)=O] | 2-methoxy-4-[(3R)-3-pyrrolidin-1-ylpyrrolidin-1-yl]benzamide | A.19 |
| B.24 | 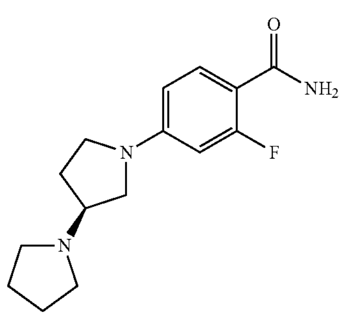 [SMILES: NC(=O)c1ccc(N2CC[C@H](N3CCCC3)C2)cc1F] | 2-fluoro-4-[(3S)-3-pyrrolidin-1-ylpyrrolidin-1-yl]benzamide | A.20 |

Intermediate B.25

Preparation of tert-butyl 4-(4-carbamoyl-3-chloro-5-fluorophenyl)piperazine-1-carboxylate

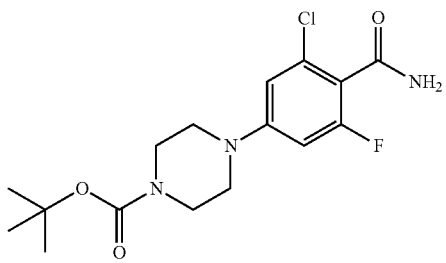 [SMILES: CC(C)(C)OC(=O)N1CCN(c2cc(F)c(C(N)=O)c(Cl)c2)CC1]

Step A:

A solution of 4-bromo-2-chloro-6-fluorobenzoic acid (1.00 g, 3.95 mmol, Eq: 1.00), tert-butyl piperazine-1-carboxylate (882 mg, 4.73 mmol, Eq: 1.2), BINAP (491 mg, 0.789 mmol, Eq: 0.2) and cesium carbonate (3.86 g, 11.8 mmol, Eq: 3), Pd(OAc)$_2$ (177 mg, 0.789 mmol, Eq: 0.2) in dioxane (15 ml) was heated at 100° and stirred overnight. The reaction mixture was concentrated in vacuo. The residue was taken up in EtOAc and washed with an aqueous solution of citric acid. The crude was purified by column chromatography (SiO$_2$, CH$_2$Cl$_2$/MeOH 95/5 to 8/2) to afford 0.308 g (22%) of 4-(4-tert-butoxycarbonylpiperazin-1-yl)-2-chloro-6-fluoro-benzoic acid as a light brown solid.

Step B:

4-(4-(tert-butoxycarbonyl)piperazin-1-yl)-2-chloro-6-fluorobenzoic acid (190 mg, 530 mmol, Eq: 1.00) and CDI (0.112 g, 0.688 mmol, Eq: 1.3) were combined in DMF (2.5 ml) to give a light yellow solution. The reaction mixture was stirred for 1.5 hours. Additional CDI (85.9 mg, 0.530 mmol, Eq: 1.00) was added and the reaction mixture was stirred for a further 1.5 hours. Ammonium hydroxide (1.03 ml, 26.5 mmol, Eq: 50) was added and the reaction mixture was stirred for 1 hour. The reaction mixture was extracted with CH$_2$Cl$_2$ and dried over Na$_2$SO$_4$, and concentrated under vacuo. A column chromatography (SiO$_2$, CH$_2$Cl$_2$/MeOH 98/2) afforded the title compound (0.12 g, 62%) as a light yellow solid. MS (m/e): 302.1 (M-tBu+H$^+$).

Intermediate B.26

Preparation of tert-butyl (2R)-4-(5-carbamoyl-6-methoxypyridin-2-yl)-2-ethylpiperazine-1-carboxylate

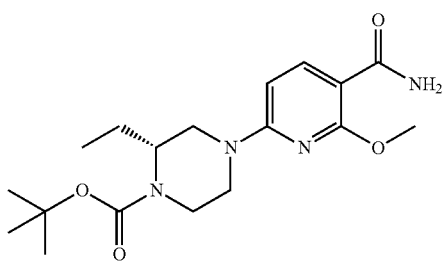 [SMILES: CC[C@@H]1CN(c2ccc(C(N)=O)c(OC)n2)CCN1C(=O)OC(C)(C)C]

Step A:

To a solution of (R)-tert-butyl 2-ethylpiperazine-1-carboxylate (0.208 g, 0.971 mmol, Eq: 1.00) and triethylamine (0.135 ml, 0.971 mmol, Eq: 1.00) in DMF (2 ml) was added methyl 2,6-dichloronicotinate (0.200 g, 0.971 mmol, Eq: 1.00) and the reaction mixture stirred at 30° C. for 4.5 hrs. The reaction mixture was diluted with EtOAc and washed with water and brine, the organic phase was dried over Na$_2$SO$_4$ and the solvent evaporated. The crude was purified by column chromatography (SiO$_2$, EtOAc/Heptane, ¼) to give 160 mg (43%) of tert-butyl (2R)-4-(6-chloro-5-methoxycarbonyl-2-pyridyl)-2-ethyl-piperazine-1-carboxylate as a white solid. MS (m/e): 384.2 (M+H$^+$).

Step B:

In a sealed tube, tert-butyl (2R)-4-(6-chloro-5-methoxycarbonyl-2-pyridyl)-2-ethyl-piperazine-1-carboxylate (161 mg, 0.419 mmol, Eq: 1.00) was dissolved in MeOH (2 ml), sodium methoxide (0.388 ml, 2.1 mmol, Eq: 5) was added and the mixture heated to 90° C. and stirred for 4.5 hrs. The reaction mixture was acidified with an aqueous solution of citric acid, extracted with CH$_2$Cl$_2$, washed with water and dried over Na$_2$SO$_4$ to give 6-[(3R)-4-tert-butoxycarbonyl-3-ethyl-piperazin-1-yl]-2-methoxy-pyridine-3-carboxylic acid. MS (m/e): 366.2 (M+H$^+$). The crude product was used directly in the next step without further purification.

Step C:

A solution of 6-[(3R)-4-tert-butoxycarbonyl-3-ethyl-piperazin-1-yl]-2-methoxy-pyridine-3-carboxylic acid (135 mg, 0.369 mmol, Eq: 1.00) and CDI (71.9 mg, 0.443 mmol, Eq: 1.2) in DMF (3 ml) was stirred at RT for 1 h. Ammonium hydroxide (0.719 ml, 18.5 mmol, Eq: 50) was added and stirred for 2 more hours. The reaction mixture was diluted with water and extracted with EtOAc, dried over Na$_2$SO$_4$ and the solvent evaporated. Crude was purified by column chromatography to give the title product tert-butyl (2R)-4-(5-carbamoyl-6-methoxypyridin-2-yl)-2-ethylpiperazine-1-carboxylate as a white solid (20 mg, 15%). MS (m/e): 365.2 (M+H$^+$).

Intermediate B.27

Preparation of tert-butyl 4-(5-carbamoyl-6-methoxypyridin-2-yl)piperazine-1-carboxylate

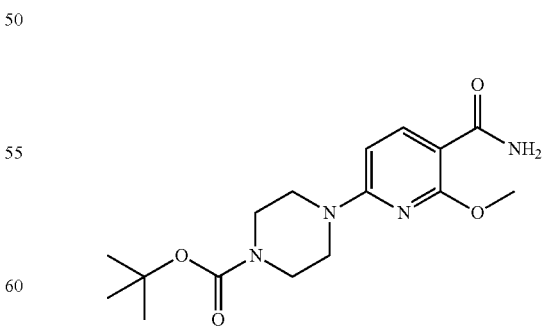

In analogy to Intermediate B.26, tert-butyl 4-(5-carbamoyl-6-methoxypyridin-2-yl)piperazine-1-carboxylate was prepared from methyl 2,6-dichloronicotinate and tert-butyl piperazine-1-carboxylate. MS (m/e): 337.2 (M+H$^+$).

Intermediate C.1

Preparation of 6-bromo-2,8-dimethylimidazo[1,2-a]pyrazine

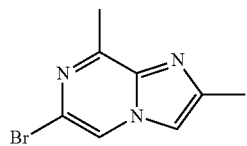

To a suspension of 5-bromo-3-methylpyrazin-2-amine (4.63 g, 24.6 mmol) in iPrOH (30 ml) was added 1-bromo-2,2-dimethoxypropane (3.66 ml, 27.1 mmol), pyridinium para-toluene sulfonic acid (0.62 g, 2.5 mmol) and the mixture heated to 65° C. in a sealed tube for 36 h. The reaction was diluted with DCM, washed with saturated sodium hydrogen carbonate solution, dried (Na$_2$SO$_4$) and concentrated. Purification by flash column chromatography on silica gel (EtOAc: Hept 1:4-1:1) afforded the titled product as a light yellow crystalline solid (3.96 g, 71%). MS (m/e): 226.1 (M+H$^+$, Br)

Intermediate C.2

Preparation of 6-bromo-8-ethyl-2-methylimidazo[1,2-a]pyrazine

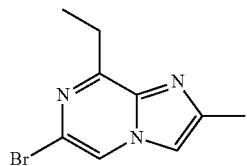

To a suspension of 5-bromo-3-ethylpyrazin-2-amine (0.68, 3.37 mmol) in iPrOH (10 ml) was added 1-bromo-2,2-dimethoxypropane (0.54 ml, 4.04 mmol), pyridinium para-toluene sulfonic acid (0.084 g, 0.337 mmol) and the mixture heated to 90° C. for 4 h. The reaction was diluted with DCM, washed with saturated sodium hydrogen carbonate solution, dried (Na$_2$SO$_4$) and concentrated. Purification by flash column chromatography on silica gel (EtOAc: Hept 1:4-1:1) afforded the titled product as a light brown solid (0.51 g, 63%). MS (m/e): 240.1 (M+H$^+$, Br).

Intermediate C.3

Preparation of 6-bromo-8-cyclopropyl-2-methylimidazo[1,2-a]pyrazine

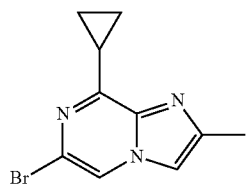

Step A:

To a solution of 3-cyclopropylpyrazin-2-amine (275 mg, 2.03 mmol, Eq: 1.00) in acetonitrile (10 ml) cooled in an ice-bath was added N-bromosuccinimide (362 mg, 2.03 mmol, Eq: 1.00) portionwise. After 20 minutes, the solvent was evaporated and purification by column chromatography (SiO$_2$, heptane/EtOAc 2/1) afforded (279 mg, 64%) of 5-bromo-3-cyclopropyl-pyrazin-2-amine as a light yellow solid. MS (m/e): 214.1 (M+H+, Br).

Step B:

To a suspension of 5-bromo-3-cyclopropylpyrazin-2-amine (0.274, 1.28 mmol) in iPrOH (5 ml) was added 1-bromo-2,2-dimethoxypropane (0.207 ml, 1.54 mmol), pyridinium para-toluene sulfonic acid (0.032 g, 0.128 mmol) and the mixture heated to 90° C. for 3 h. The reaction was diluted with DCM, washed with saturated sodium hydrogen carbonate solution, dried (Na$_2$SO$_4$) and concentrated. Purification by flash column chromatography on silica gel (EtOAc: Hept 1:4-1:1) afforded the titled product 6-bromo-8-cyclopropyl-2-methylimidazo[1,2-a]pyrazine as a light brown solid (0.158 g, 48%). MS (m/e): 252.1 (M+H$^+$, Br).

Intermediate C.4

Preparation of 6-chloro-8-trifluoromethyl-2-methylimidazo[1,2-a]pyrazine

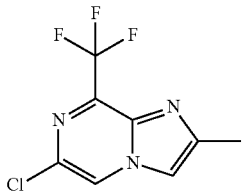

Step A:

To a solution of sodium trifluoromethanesulfinate (1.2 g, 7.7 mmol) in water (12 ml) was added a solution of 5-chloropyrazin-2-amine (1.0 g, 7.7 mmol) in DCM (30 ml). tert-Butylhydroperoxide (1.0 ml, 5.5 M in nonane, 5.5 mmol) was added dropwise over 2 h. A second portion of sodium trifluoromethanesulfinate (1.2 g, 7.7 mmol) was then added followed by a second portion of tert-butylhydroperoxide (1.0 ml, 5.5 M in nonane, 5.5 mmol) was added dropwise over 6 h. The reaction was repeatedly extracted with DCM and the combined organic extracts washed with brine, dried (Na$_2$SO$_4$) and concentrated. Purification by flash column chromatography on silica gel (DCM) afforded 5-chloro-3-(trifluoromethyl)pyrazin-2-amine as yellow crystals (0.9 g, 57%). MS (m/e): 198.0. (M+H$^+$, Cl)

Step B:

To a suspension of 5-chloro-3-(trifluoromethyl)pyrazin-2-amine (0.77 g, 3.8 mmol) in iPrOH (6 ml) was added 1-bromo-2,2-dimethoxypropane (0.57 ml, 4.2 mmol), pyridinium para-toluene sulfonic acid (0.1 g, 0.4 mmol) and the mixture heated to 100° C. in a sealed tube for 96 h. The reaction was diluted with DCM, washed with saturated sodium hydrogen carbonate solution, dried (Na$_2$SO$_4$) and concentrated. Purification by flash column chromatography on silica gel (EtOAc: Hept 3:7-1:0) afforded the titled product as a brown powder (0.15 g, 17%). MS (m/e): 236.1. (M+H$^+$, Cl)

Intermediate C.5

Preparation of 6-chloro-8-difluoromethyl-2-methyl-imidazo[1,2-a]pyrazine

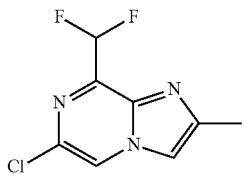

Step A:

To a solution of 5-chloropyrazin-2-amine (1.0 g, 7.7 mmol) in DCM (60 ml) was added a suspension of bis(difluoromethylsulfinyloxy)zinc (2.3 g, 7.7 mmol) and Fe(NO3)$_3$.9H$_2$O (0.3 g, 0.8 mmol) in water (24 ml) and the mixture was stirred. tert-Butylhydroperoxide (2.2 ml, 5.5 M in nonane 12.1 mmol) was added in 0.2 ml portions every 45 min for a total reaction time of 8 h. The reaction was diluted with DCM, washed with water, dried (Na$_2$SO$_4$) and concentrated. Purification by flash column chromatography on silica gel (DCM:MeOH 1:0-4:1) afforded 5-chloro-3-(difluoromethyl)pyrazin-2-amine as a yellow crystals (0.6 g, 40%). MS (m/e): 180.0. (M+H$^+$, Cl).

Step B:

To a suspension 5-chloro-3-(difluoromethyl)pyrazin-2-amine (0.5 g, 2.8 mmol) in iPrOH (10 ml) was added 1-bromo-2,2-dimethoxypropane (1.1 ml, 8.4 mmol), pyridinium para-toluene sulfonic acid (0.1 g, 0.3 mmol) and the mixture heated to 65° C. in a sealed tube for 18 h. The reaction was diluted with DCM, washed with saturated sodium hydrogen carbonate solution, dried (Na$_2$SO$_4$) and concentrated. Purification by flash column chromatography on silica gel (EtOAc: Hept 1:4-1:0) afforded the titled product as a brown powder (0.20 g, 40%). MS (m/e): 218.1. (M+H$^+$, Cl)

Intermediate D.1

4-Bromo-2-fluoro-N-(2-methylimidazo[1,2-a]pyrazin-6-yl)benzamide

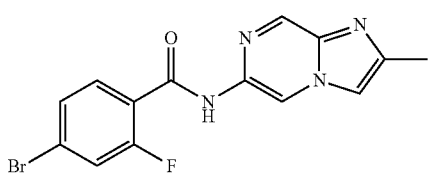 [SMILES: Cc1cn2cc(NC(=O)c3ccc(Br)cc3F)ncc2n1]

In a sealed tube, 4-bromo-2-fluorobenzamide (150 mg, 0.688 mmol), 6-bromo-2-methylimidazo[1,2-a]pyrazine (146 mg, 0.688 mmol), copper (I) iodide (13.1 mg, 0.068 mmol, 0.1 eq.), K$_3$PO$_4$ (307 mg, 1.44 mmol, 2.1 eq.) and 1,10-phenantroline (14.9 mg, 0.138 mmol, 0.2 eq.) in dioxane (5 mL) was heated at 120° C. overnight. The reaction mixture was filtered on celite, concentrated under vacuo, and purification on column chromatography (SiO$_2$, CH$_2$Cl$_2$/MeOH 99/1 to 98/2) afforded 24 mg (10%) of 4-bromo-2-fluoro-N-(2-methylimidazo[1,2-a]pyrazin-6-yl)benzamide. MS (m/e): 349.1 (M+H$^+$, Br).

Intermediate D.2

4-Bromo-N-(2-methylimidazo[1,2-a]pyrazin-6-yl)benzamide

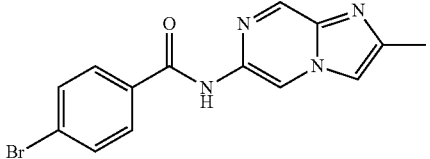 [SMILES: Cc1cn2cc(NC(=O)c3ccc(Br)cc3)ncc2n1]

In a sealed tube, 4-bromobenzamide (94.3 mg, 0.472 mmol), 6-bromo-2-methylimidazo[1,2-a]pyrazine (100 mg, 0.472 mmol), copper (I) iodide (8.9 mg, 0.047 mmol, 0.1 eq.), K$_3$PO$_4$ (210 mg, 0.99 mmol, 2.1 eq.) and 1,10-phenantroline (17 mg, 0.094 mmol, 0.2 eq.) in dioxane (5 mL) was heated at 120° C. overnight. The reaction mixture was filtered on celite, concentrated under vacuo, and purification on column chromatography (SiO$_2$, CH$_2$Cl$_2$/MeOH 99/1 to 98/2) afforded 42 mg (18%) of 4-bromo-N-(2-methylimidazo[1,2-a]pyrazin-6-yl)Benzamide as a white solid. MS (m/e): 331.1 (M+H$^+$, Br).

Intermediate D.3

4-Bromo-2-ethoxy-N-(2-methylimidazo[1,2-a]pyrazin-6-yl)benzamide

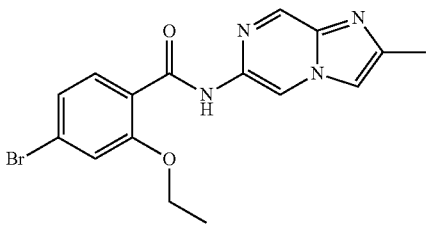 [SMILES: CCOc1cc(Br)ccc1C(=O)Nc1cn2cc(C)nc2cn1]

In a sealed tube, 4-bromo-2-ethoxybenzamide (288 mg, 0.1.18 mmol), 6-bromo-2-methylimidazo[1,2-a]pyrazine (275 mg, 1.30 mmol), copper (I) iodide (22.5 mg, 0.118 mmol, 0.1 eq.), K$_3$PO$_4$ (526 mg, 2.48 mmol, 2.1 eq.) and 1,10-phenantroline (42.5 mg, 0.236 mmol, 0.2 eq.) in dioxane (5 mL) was heated at 120° C. overnight. The reaction mixture was filtered on celite, concentrated under vacuo, and purification on column chromatography (SiO$_2$, CH$_2$Cl$_2$/MeOH 99/1 to 98/2) afforded 159 mg (36%) of the title product as a white solid. MS (m/e): 375.2 (M+H$^+$, Br).

General Procedure 1

Buchwald Amination Reaction

A solution of an aryl bromide derivative (1 equiv.), a secondary amine (2 equiv.), tris(dibenzylidene-acetone)dipalladium(0) (Pd$_2$(dba)$_3$) (0.08 equiv.), sodium tert-butoxide (1.5 equiv.) and diphenylphosphino)-9,9-dimethylxanthene (Xantphos) (0.12 equiv.) in toluene was heated at 80-130° C. overnight. The solvent was evaporated and the product was directly purified by column chromatography on silica gel.

General Procedure 2

Boc Deprotection

The Boc-protected amine was put in solution in a mixture of MeOH-dioxane. A solution of HCl in dioxane (4M, 10 equiv.) was added and stirring was continued until completion (0.2 h to 4 hours). The desired product was collected by filtration and dried in vacuo.

Example 1

Preparation of 2-fluoro-N-(2-methylimidazo[1,2-a]pyrazin-6-yl)-4-piperazin-1-ylbenzamide hydrochloride

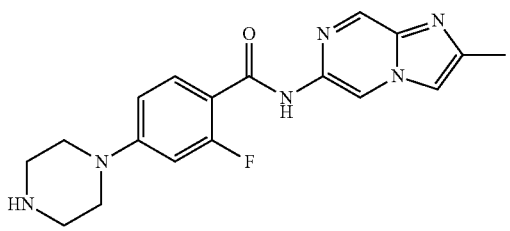 [SMILES: Cc1cn2cc(NC(=O)c3ccc(N4CCNCC4)cc3F)ncc2n1]

Following the General Procedure 1 (Buchwald amination) followed by the General Procedure 2 (Boc deprotection), 2-fluoro-N-(2-methylimidazo[1,2-a]pyrazin-6-yl)-4-piperazin-1-ylbenzamide hydrochloride was prepared from 4-bromo-2-fluoro-N-(2-methylimidazo[1,2-a]pyrazin-6-yl) Benzamide (example D.1) and tert-butyl piperazine-1-carboxylate. MS (m/e): 391.8 (M+H$^+$).

Example 2

Preparation of N-(2-methylimidazo[1,2-a]pyrazin-6-yl)-4-piperazin-1-ylbenzamide hydrochloride

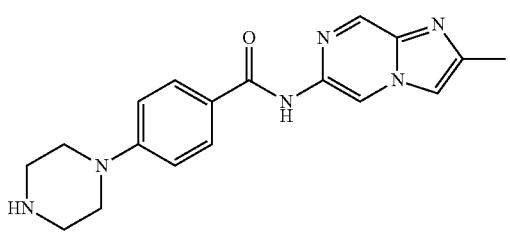 [SMILES: Cc1cn2cc(NC(=O)c3ccc(N4CCNCC4)cc3)ncc2n1]

Following the General Procedure 1 (Buchwald amination) followed by the General Procedure 2 (Boc deprotection), N-(2-methylimidazo[1,2-a]pyrazin-6-yl)-4-piperazin-1-ylbenzamide hydrochloride was prepared from 4-bromo-N-(2-methylimidazo[1,2-a]pyrazin-6-yl)benzamide (example D.2) and tert-butyl piperazine-1-carboxylate. MS (m/e): 337.1 (M+H$^+$).

Example 3

Preparation of 4-[(8aS)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide

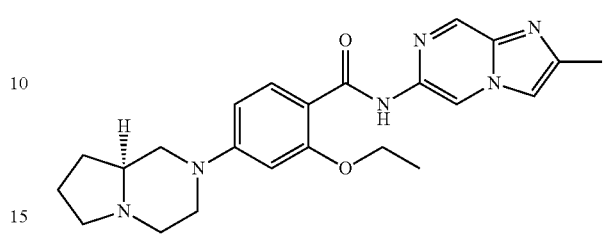

Following the General Procedure 1 (Buchwald amination), 4-[(8aS)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide was prepared from 4-bromo-2-ethoxy-N-(2-methylimidazo[1,2-a]pyrazin-6-yl)benzamide (example D.3) and (8aS)-1,2,3,4,6,7,8,8a-octahydropyrrolo[1,2-a]pyrazine. MS (m/e): 421.4 (M+H$^+$).

Example 4

Preparation of 2-ethoxy-N-(2-methylimidazo[1,2-a]pyrazin-6-yl)-4-[(3S)-3-methylpiperazin-1-yl]benzamide

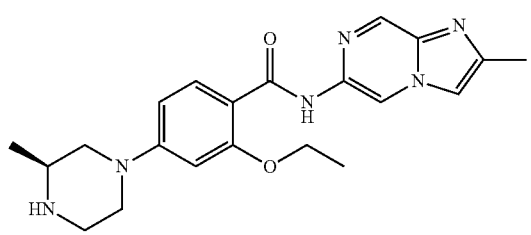

Following the General Procedure 1 (Buchwald amination) followed by General Procedure 2 (Boc deprotection), 2-ethoxy-N-(2-methylimidazo[1,2-a]pyrazin-6-yl)-4-[(3S)-3-methylpiperazin-1-yl]benzamide was prepared from 4-bromo-2-ethoxy-N-(2-methylimidazo[1,2-a]pyrazin-6-yl)benzamide (example D.3) and tert-butyl (2S)-2-methylpiperazine-1-carboxylate. MS (m/e): 395.3 (M+H$^+$).

Example 5

Preparation of 2-ethoxy-N-(2-methylimidazo[1,2-a]pyrazin-6-yl)-4-[(3R)-3-methylpiperazin-1-yl]benzamide

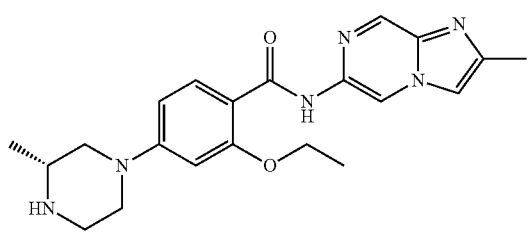

Following the General Procedure 1 (Buchwald amination) followed by General Procedure 2 (Boc deprotection), 2-ethoxy-N-(2-methylimidazo[1,2-a]pyrazin-6-yl)-4-[(3R)-3-methylpiperazin-1-yl]benzamide was prepared from 4-bromo-2-ethoxy-N-(2-methylimidazo[1,2-a]pyrazin-6-yl)benzamide (example D.3) and tert-butyl (2R)-2-methylpiperazine-1-carboxylate. MS (m/e): 395.3 (M+H⁺).

Example 6

Preparation of 4-[(8aR)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide

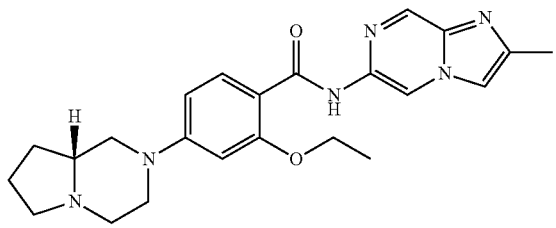 [SMILES: CCOc1cc(N2CCN3CCC[C@@H]3C2)ccc1C(=O)Nc1cn2cc(C)nc2cn1]

Following the General Procedure 1 (Buchwald amination), 4-[(8aR)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide was prepared from 4-bromo-2-ethoxy-N-(2-methylimidazo[1,2-a]pyrazin-6-yl)benzamide (example D.3) and (8aR)-1,2,3,4,6,7,8,8a-octahydropyrrolo[1,2-a]pyrazine. MS (m/e): 421.4 (M+H⁺).

Example 7

Preparation of 4-[(8aR)-3,4,6,7,8,8a-hexahydro-1H-pyrrolo[1,2-a]pyrazin-2-yl]-2-fluoro-N-(2-methylimidazo[1,2-a]pyrazin-6-yl)benzamide

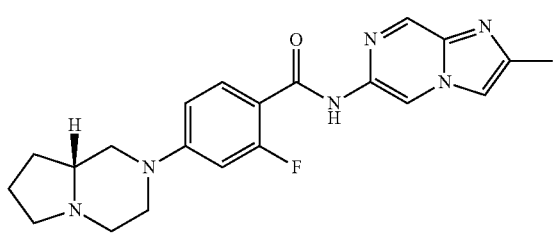 [SMILES: Cc1cn2cc(NC(=O)c3ccc(N4CCN5CCC[C@@H]5C4)cc3F)ncc2n1]

Following the General Procedure 1 (Buchwald amination), 4-[(8aR)-3,4,6,7,8,8a-hexahydro-1H-pyrrolo[1,2-a]pyrazin-2-yl]-2-fluoro-N-(2-methylimidazo[1,2-a]pyrazin-6-yl)benzamide was prepared from 4-bromo-2-fluoro-N-(2-methylimidazo[1,2-a]pyrazin-6-yl)benzamide (example D.1) and (8aR)-1,2,3,4,6,7,8,8a-octahydropyrrolo[1,2-a]pyrazine. MS (m/e): 395.3 (M+H⁺).

Example 8

Preparation of 4-[(8aS)-3,4,6,7,8,8a-hexahydro-1H-pyrrolo[1,2-a]pyrazin-2-yl]-2-fluoro-N-(2-methylimidazo[1,2-a]pyrazin-6-yl)benzamide

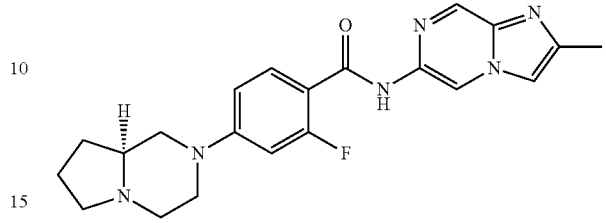

Following the General Procedure 1 (Buchwald amination), 4-[(8aS)-3,4,6,7,8,8a-hexahydro-1H-pyrrolo[1,2-a]pyrazin-2-yl]-2-fluoro-N-(2-methylimidazo[1,2-a]pyrazin-6-yl)benzamide was prepared from 4-bromo-2-fluoro-N-(2-methylimidazo[1,2-a]pyrazin-6-yl)benzamide (example D.1) and (8aS)-1,2,3,4,6,7,8,8a-octahydropyrrolo[1,2-a]pyrazine. MS (m/e): 395.3 (M+H⁺).

Example 9

Preparation of 4-(1,4-diazepan-1-yl)-2-ethoxy-N-(2-methylimidazo[1,2-a]pyrazin-6-yl)benzamide

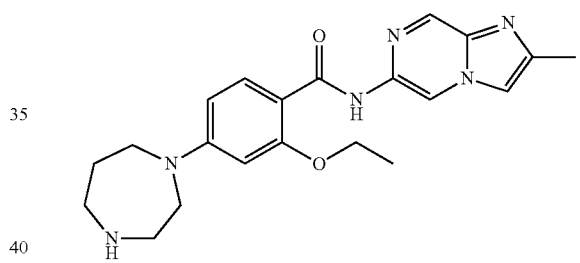

Following the General Procedure 1 (Buchwald amination), 4-(1,4-diazepan-1-yl)-2-ethoxy-N-(2-methylimidazo[1,2-a]pyrazin-6-yl)benzamide was prepared from 4-bromo-2-ethoxy-N-(2-methylimidazo[1,2-a]pyrazin-6-yl)benzamide (example D.3) and 1,4-diazepane. MS (m/e): 395.3 (M+H⁺).

Example 10

Preparation of 4-[(3S,5R)-3,5-dimethylpiperazin-1-yl]-2-ethoxy-N-(2-methylimidazo[1,2-a]pyrazin-6-yl)benzamide

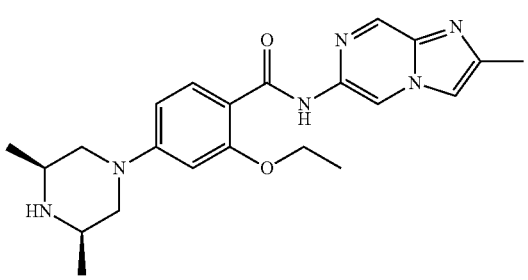

Following the General Procedure 1 (Buchwald amination), 4-(1,4-diazepan-1-yl)-2-ethoxy-N-(2-methylimidazo[1,2-a]pyrazin-6-yl)benzamide was prepared from 4-bromo-2-ethoxy-N-(2-methylimidazo[1,2-a]pyrazin-6-yl)benzamide (example D.3) and (2R,6S)-2,6-dimethylpiperazine. MS (m/e): 409.3 (M+H⁺).

Example 11

Preparation of N-(2,8-dimethylimidazo[1,2-a]pyrazin-6-yl)-2-fluoro-4-[(3R)-3-methylpiperazin-1-yl]benzamide

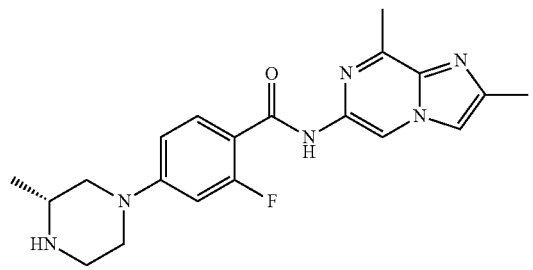

Step A:
In a tube, a suspension of (R)-tert-butyl 4-(4-carbamoyl-3-fluorophenyl)-2-methylpiperazine-1-carboxylate (0.10 g, 0.3 mmol, Intermediate B.1), 6-bromo-2,8-dimethylimidazo[1,2-a]pyrazine (0.08 g, 0.4 mmol, Intermediate C.1), (diphenylphosphino)-9,9-dimethylxanthene (0.03 g, 0.04 mmol), cesium carbonate (0.14 g, 0.4 mmol) in dioxane (2 ml) was degassed by sonication with argon bubbling. Tris(dibenzylideneacetone)dipalladium(0) (0.01 g, 0.1 mmol) was then added the tube sealed and the mixture heated to 100° C. for 3 h. The reaction was then diluted with DCM, washed with water, dried (Na₂SO₄) and concentrated. Purification by flash column chromatography on silica gel (EtOAc: Hept 1:1-7:3) afforded (R)-tert-butyl 4-(4-(2,8-dimethylimidazo[1,2-a]pyrazin-6-ylcarbamoyl)-3-fluorophenyl)-2-methylpiperazine-1-carboxylate (0.11 g, 77%) as a light brown powder. MS (m/e): 483.4 (M+H⁺).

Step B:
(R)-tert-butyl 4-(4-(2,8-dimethylimidazo[1,2-a]pyrazin-6-ylcarbamoyl)-3-fluorophenyl)-2-methylpiperazine-1-carboxylate (0.10 g, 0.2 mmol) was suspended in hydrochloric acid in dioxane (4 ml, 4 M) and stirred for 20 minutes. The reaction was then evaporated to dryness, redissolved in water, washed with DCM, then the aqueous was made basic by addition of saturated sodium hydrogen carbonate solution, re-extracted with DCM:MeOH (95:5) and concentrated to afford the titled product (0.08 g, quant.) as a yellow powder. (m/e): 383.3 (M+H⁺).

In analogy to Example 11, Examples 12 to 47 of the following table were prepared from the corresponding carboxamide and heteroaryl halide followed by subsequent deprotection as required.

| Ex. No. | Structure | Systematic Name | Starting materials | MW (MH⁺) |
|---|---|---|---|---|
| 12 | 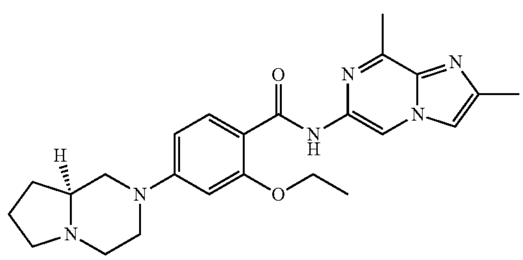 [SMILES: CCOc1cc(N2CCN3CCC[C@H]3C2)ccc1C(=O)Nc1cn2cc(C)nc2c(C)n1] | 4-[(8aS)-3,4,6,7,8,8a-hexahydro-1H-pyrrolo[1,2-a]pyrazin-2-yl]-N-(2,8-dimethyl-imidazo[1,2-a]pyrazin-6-yl)-2-ethoxybenzamide | 4-[(8aS)-3,4,6,7,8,8a-hexahydro-1H-pyrrolo[1,2-a]pyrazin-2-yl]-2-ethoxy-benzamide (B.21) and 6-bromo-2,8-dimethyl-imidazo[1,2-a]pyrazine (C.1) | 435.4 |
| 13 | 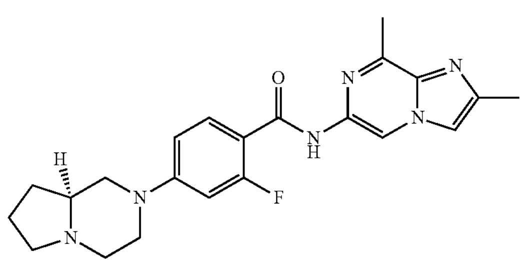 [SMILES: Cc1cn2cc(NC(=O)c3ccc(N4CCN5CCC[C@H]5C4)cc3F)nc(C)c2n1] | 4-[(8aS)-3,4,6,7,8,8a-hexahydro-1H-pyrrolo[1,2-a]pyrazin-2-yl]-N-(2,8-dimethyl-imidazo[1,2-a]pyrazin-6-yl)-2-fluorobenzamide | 4-[(8aS)-3,4,6,7,8,8a-hexahydro-1H-pyrrolo[1,2-a]pyrazin-2-yl]-2-fluoro-benzamide (B.19) and 6-bromo-2,8-dimethyl-imidazo[1,2-a]pyrazine (C.1) | 409.3 |
| 14 | 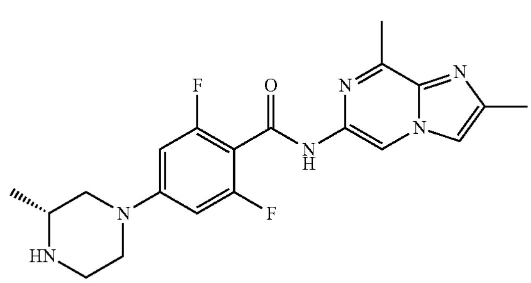 | N-(2,8-dimethyl-imidazo[1,2-a]pyrazin-6-yl)-2,6-difluoro-4-[(3R)-3-methyl-piperazin-1-yl]benzamide | tert-butyl (2R)-4-(4-carbamoyl-3,5-difluoro-phenyl)-2-methylpiperazine-1-carboxylate (B.4) and 6-bromo-2,8-dimethyl-imidazo[1,2-a]pyrazine (C.1) | 401.3 |

-continued

| Ex. No. | Structure | Systematic Name | Starting materials | MW (MH+) |
|---|---|---|---|---|
| 15 | 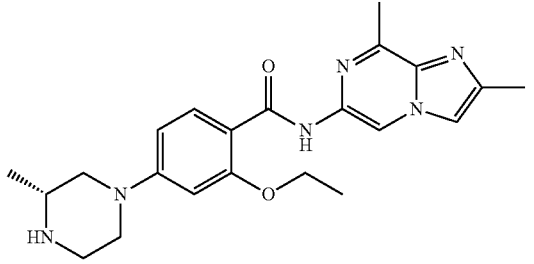 | N-(2,8-dimethyl-imidazo[1,2-a]pyrazin-6-yl)-2-ethoxy-4-[(3R)-3-methyl-piperazin-1-yl]benzamide | tert-butyl (2R)-4-(4-carbamoyl-3-ethoxyphenyl)-2-methyl-piperazine-1-carboxylate (B.3) and 6-bromo-2,8-dimethyl-imidazo[1,2-a]pyrazine (C.1) | 409.3 |
| 16 | 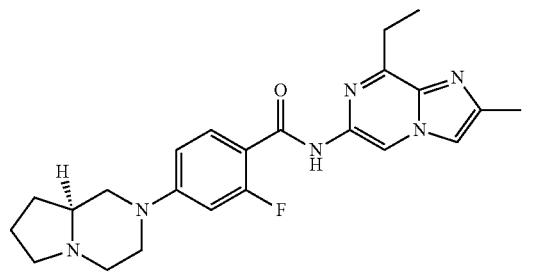 [SMILES: CCc1nc(NC(=O)c2ccc(N3CCN4CCC[C@H]4C3)cc2F)cn2cc(C)nc12] | 4-[(8aS)-3,4,6,7,8,8a-hexahydro-1H-pyrrolo[1,2-a]pyrazin-2-yl]-N-(8-ethyl-2-methylimidazo[1,2-a]pyrazin-6-yl)-2-fluorobenzamide | 4-[(8aS)-3,4,6,7,8,8a-hexahydro-1H-pyrrolo[1,2-a]pyrazin-2-yl]-2-fluoro-benzamide (B.19) and 6-bromo-8-ethyl-2-methylimidazo[1,2-a]pyrazine (C.2) | 423.2 |
| 17 | 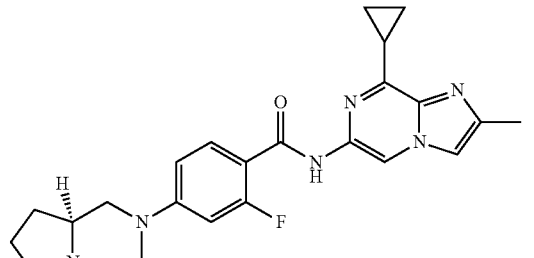 | 4-[(8aS)-3,4,6,7,8,8a-hexahydro-1H-pyrrolo[1,2-a]pyrazin-2-yl]-N-(8-cyclopropyl-2-methylimidazo[1,2-a]pyrazin-6-yl)-2-fluorobenzamide | 4-[(8aS)-3,46,7,8,8a-hexahydro-1H-pyrrolo[1,2-a]pyrazin-2-yl]-2-fluoro-benzamide (B.19) and of 6-bromo-8-cyclopropyl-2-methylimidazo[1,2-a]pyrazine (C.3) | 435.3 |
| 18 | 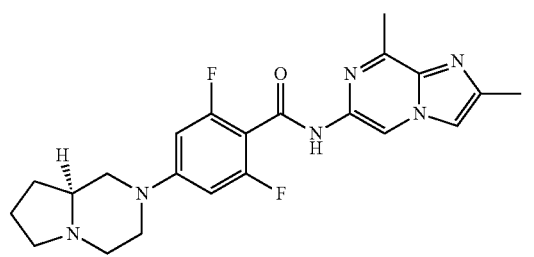 [SMILES: Cc1cn2cc(NC(=O)c3c(F)cc(N4CCN5CCC[C@H]5C4)cc3F)nc(C)c2n1] | 4-[(8aS)-3,4,6,7,8,8a-hexahydro-1H-pyrrolo[1,2-a]pyrazin-2-yl]-N-(2,8-dimethyl-imidazo[1,2-a]pyrazin-6-yl)-2,6-difluoro-benzamide | 4-[(8aS)-3,4,6,7,8,8a-hexahydro-1H-pyrrolo[1,2-a]pyrazin-2-yl]-2,6-difluoro-benzamide (B.20) and 6-bromo-2,8-dimethyl-imidazo[1,2-a]pyrazine (C.1) | 427.3 |
| 19 | 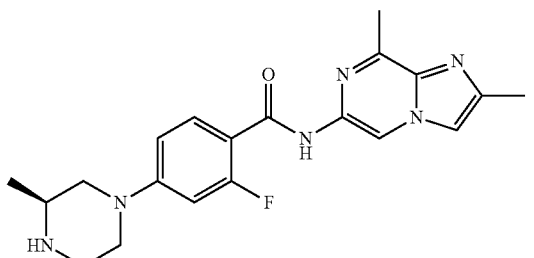 | N-(2,8-dimethyl-imidazo[1,2-a]pyrazin-6-yl)-4-[(3R,5S)-3,5-dimethyl-piperazin-1-yl]-2-fluoro-benzamide | benzyl (2R,6S)-4-(4-carbamoyl-3-fluorophenyl)-2,6-dimethyl-piperazine-1-carboxylate (B.5) and 6-bromo-2,8-dimethyl-imidazo[1,2-a]pyrazine (C.1): deprotection with 10% palladium on charcoal in MeOH under an atmosphere of hydrogen | 397.3 |

-continued

| Ex. No. | Structure | Systematic Name | Starting materials | MW (MH+) |
|---|---|---|---|---|
| 20 | 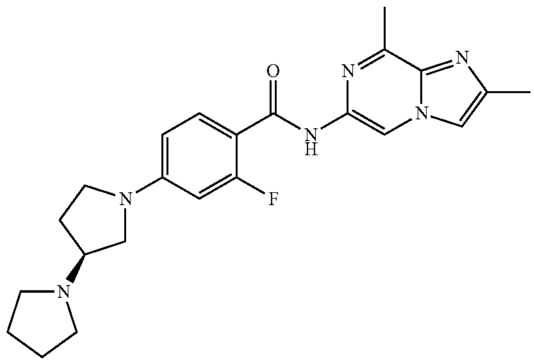 [SMILES: Cc1cn2cc(NC(=O)c3ccc(N4CC[C@H](N5CCCC5)C4)cc3F)nc(C)c2n1] | N-(2,8-dimethyl-imidazo[1,2-a]pyrazin-6-yl)-2-fluoro-4-[(3S)-3-pyrrolidin-1-ylpyrrolidin-1-yl]benzamide | 2-fluoro-4-[(3S)-3-pyrrolidin-1-ylpyrrolidin-1-yl]benzamide (B.22) and 6-bromo-2,8-dimethyl-imidazo[1,2-a]pyrazine (C.1) | 423.4 |
| 21 | 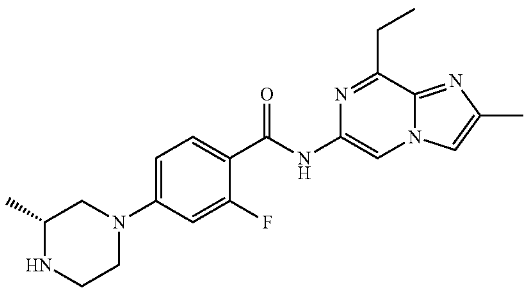 | N-(8-ethyl-2-methylimidazo[1,2-a]pyrazin-6-yl)-2-fluoro-4-[(3R)-3-methylpiperazin-1-yl]benzamide hydrochloride | tert-butyl (2R)-4-(4-carbamoyl-3-ethoxyphenyl)-2-methyl-piperazine-1-carboxylate (B.3) and 6-bromo-8-ethyl-2-methyl-imidazo[1,2-a]pyrazine (C.2) | 397.3 |
| 22 | 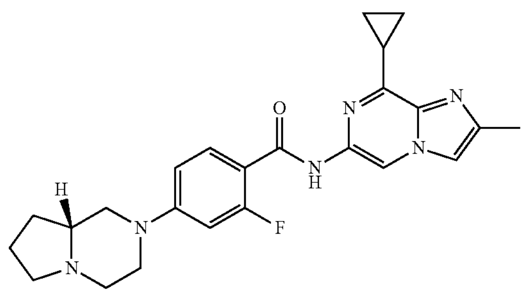 [SMILES: Cc1cn2cc(NC(=O)c3ccc(N4CCN5CCC[C@@H]5C4)cc3F)nc(C3CC3)c2n1] | 4-[(8aR)-3,4,6,7,8,8a-hexahydro-1H-pyrrolo[1,2-a]pyrazin-2-yl]-N-(8-cyclopropyl-2-methyl-imidazo[1,2-a]pyrazin-6-yl)-2-fluoro-benzamide | 4-[(8aR)-3,4,6,7,8,8a-hexahydro-1H-pyrrolo[1,2-a]pyrazin-2-yl]-2-fluoro-benzamide (B.18) and 6-bromo-8-cyclopropyl-2-methylimidazo[1,2-a]pyrazine (C.3) | 435.3 |
| 23 | 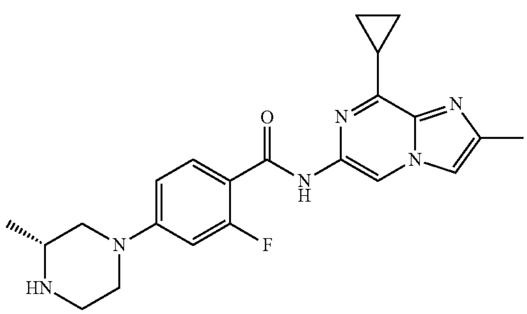 | N-(8-cyclopropyl-2-methylimidazo[1,2-a]pyrazin-6-yl)-2-fluoro-4-[(3R)-3-methylpiperazin-1-yl]benzamide hydrochloride | tert-butyl (2R)-4-(4-carbamoyl-3-ethoxy-phenyl)-2-methyl-piperazine-1-carboxylate (B.3) and 6-bromo-8-cyclopropyl-2-methylimidazo[1,2-a]pyrazine (C.3) | 409.3 |
| 24 | 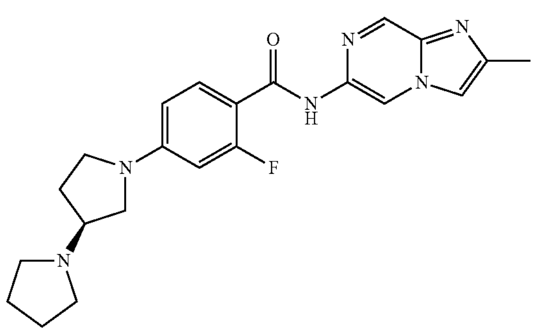 [SMILES: Cc1cn2cc(NC(=O)c3ccc(N4CC[C@H](N5CCCC5)C4)cc3F)ncc2n1] | 2-fluoro-N-(2-methylimidazo[1,2-a]pyrazin-6-yl)-4-[(3S)-3-pyrrolidin-1-ylpyrrolidin-1-yl]benzamide | 2-fluoro-4-[(3S)-3-pyrrolidin-1-ylpyrrolidin-1-yl]benzamide (B.22) and 6-bromo-2-methylimidazo[1,2-a]pyrazine | 409.3 |

| Ex. No. | Structure | Systematic Name | Starting materials | MW (MH+) |
|---|---|---|---|---|
| 25 | 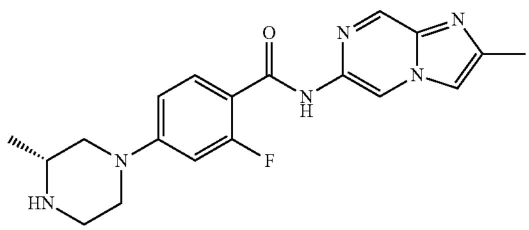 | 2-fluoro-N-(2-methylimidazo[1,2-a]pyrazin-6-yl)-4-[(3R)-3-methyl-piperazin-1-yl]benzamide hydrochloride | tert-butyl (2R)-4-(4-carbamoyl-3-ethoxyphenyl)-2-methyl-piperazine-1-carboxylate (B.3) and 6-bromo-2-methylimidazo[1,2-a]pyrazine | 369.3 |
| 26 | 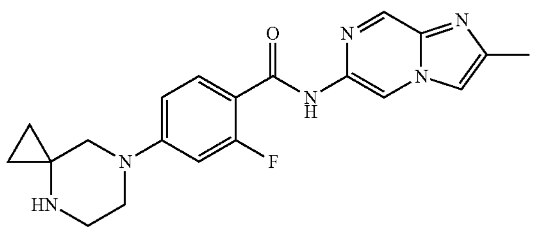 [SMILES: Cc1cn2cc(NC(=O)c3ccc(N4CCNC5(CC5)C4)cc3F)ncc2n1] | 4-(4,7-diazaspiro[2.5]octan-7-yl)-2-fluoro-N-(2-methylimidazo[1,2-a]pyrazin-6-yl)benzamide hydrochloride | tert-butyl 7-(4-carbamoyl-3-fluorophenyl)-4,7-diazaspiro[2.5]octane-4-carboxylate (B.10) and 6-bromo-2-methylimidazo[1,2-a]pyrazine | 381.2 |
| 27 | 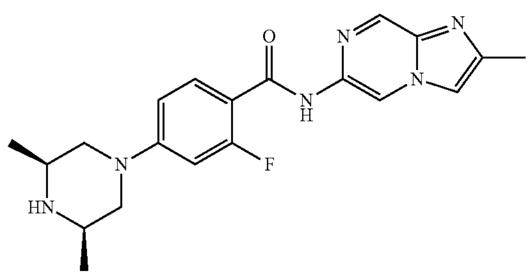 | 4-[(3S,5R)-3,5-dimethyl-piperazin-1-yl]-2-fluoro-N-(2-methylimidazo[1,2-a]pyrazin-6-yl)benzamide | benzyl (2R,6S)-4-(4-carbamoyl-3-fluorophenyl)-2,6-dimethyl-piperazine-1-carboxylate (B.6) and 6-bromo-2-methylimidazo[1,2-a]pyrazine | 383.2 |
| 28 | 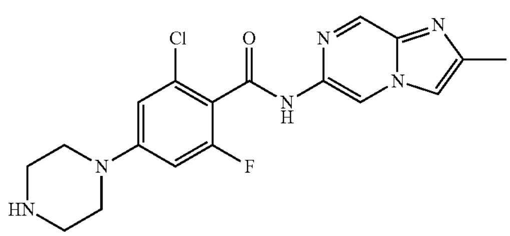 | 2-chloro-6-fluoro-N-(2-methylimidazo[1,2-a]pyrazin-6-yl)-4-piperazin-1-ylbenzamide hydrochloride | tert-butyl 4-(4-carbamoyl-3-chloro-5-fluorophenyl)piperazine-1-carboxylate (B.23) and 6-bromo-2-methylimidazo[1,2-a]pyrazine | 389.1 |
| 29 | 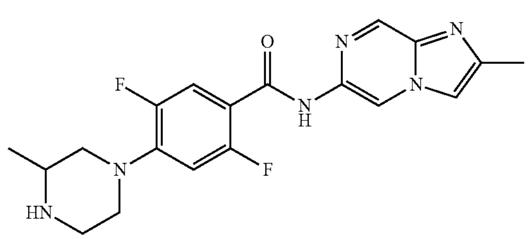 | 2,5-difluoro-N-(2-methyl-imidazo[1,2-a]pyrazin-6-yl)-4-(3-methyl-piperazin-1-yl)benzamide hydrochloride | tert-butyl 4-(4-carbamoyl-2,5-difluorophenyl)-2-methyl-piperazine-1-carboxylate (B.15) and 6-bromo-2-methylimidazo[1,2-a]pyrazine | 387.2 |
| 30 | 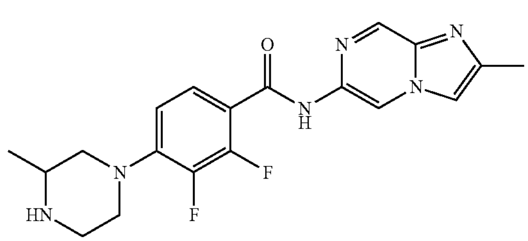 | 2,3-difluoro-N-(2-methyl-imidazo[1,2-a]pyrazin-6-yl)-4-(3-methyl-piperazin-1-yl)benzamide hydrochloride | tert-butyl 4-(4-carbamoyl-2,3-difluorophenyl)-2-methyl-piperazine-1-carboxylate (B.16) and 6-bromo-2-methylimidazo[1,2-a]pyrazine | 387.2 |

| Ex. No. | Structure | Systematic Name | Starting materials | MW (MH+) |
|---|---|---|---|---|
| 31 | 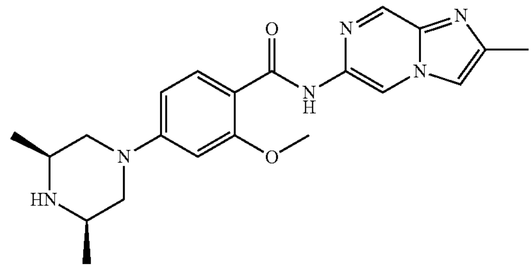 | 4-[(3R,5S)-3,5-dimethyl-piperazin-1-yl]-2-methoxy-N-(2-methyl-imidazo[1,2-a]pyrazin-6-yl)benzamide | tert-butyl (2S,6R)-4-(4-carbamoyl-3-methoxy-phenyl)-2,6-dimethyl-piperazine-1-carboxylate (B.5) and 6-bromo-2-methylimidazo[1,2-a]pyrazine | 395.2 |
| 32 | 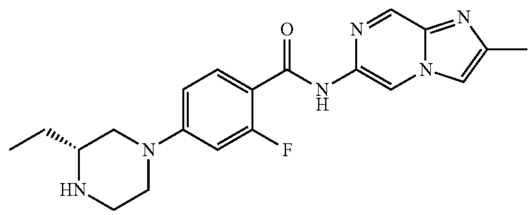 [SMILES: CC[C@@H]1CN(c2ccc(C(=O)Nc3cn4cc(C)nc4cn3)c(F)c2)CCN1] | 4-[(3R)-3-ethylpiperazin-1-yl]-2-fluoro-N-(2-methyl-imidazo[1,2-a]pyrazin-6-yl)benzamide hydrochloride | tert-butyl (2R)-4-(4-carbamoyl-3-fluorophenyl)-2-ethyl-piperazine-1-carboxylate (B.13) and 6-bromo-2-methylimidazo[1,2-a]pyrazine | 383.2 |
| 33 | 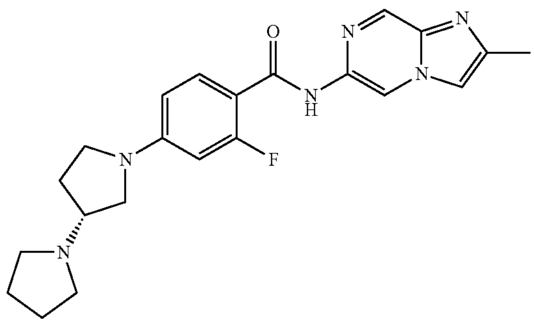 [SMILES: Cc1cn2cc(NC(=O)c3ccc(N4CC[C@@H](N5CCCC5)C4)cc3F)ncc2n1] | 2-fluoro-N-(2-methyl-imidazo[1,2-a]pyrazin-6-yl)-4-[(3R)-3-pyrrolidin-1-ylpyrrolidin-1-yl]benzamide | 2-fluoro-4-[(3R)-3-pyrrolidin-1-ylpyrrolidin-1-yl]benzamide (B.22) and 6-bromo-2-methylimidazo[1,2-a]pyrazine | 409.2 |
| 34 | 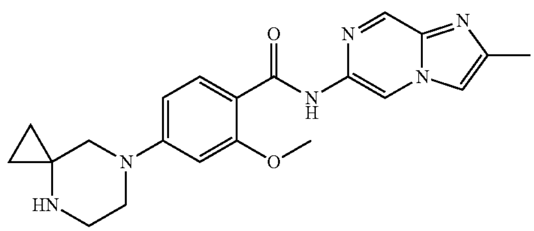 [SMILES: COc1cc(N2CCNC3(CC3)C2)ccc1C(=O)Nc1cn2cc(C)nc2cn1] | 4-(4,7-diazaspiro[2.5]octan-7-yl)-2-methoxy-N-(2-methyl-imidazo[1,2-a]pyrazin-6-yl)benzamide | tert-butyl 7-(4-carbamoyl-3-methoxy-phenyl)-4,7-diazaspiro[2.5]octane-4-carboxylate (B.9) and 6-bromo-2-methylimidazo[1,2-a]pyrazine | 393.2 |
| 35 | 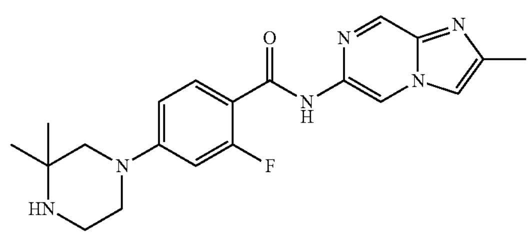 | 4-(3,3-dimethyl-piperazin-1-yl)-2-fluoro-N-(2-methylimidazo[1,2-a]pyrazin-6-yl)benzamide hydrochloride | tert-butyl 4-(4-carbamoyl-3-fluorophenyl)-2,2-dimethyl-piperazine-1-carboxylate (B.7) and 6-bromo-2-methylimidazo[1,2-a]pyrazine | 383.2 |
| 36 | 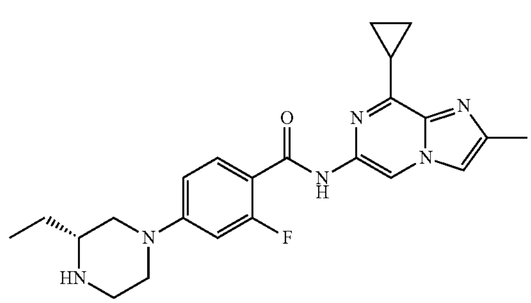 [SMILES: CC[C@@H]1CN(c2ccc(C(=O)Nc3cn4cc(C)nc4c(C4CC4)n3)c(F)c2)CCN1] | N-(8-cyclo-propyl-2-methylimidazo[1,2-a]pyrazin-6-yl)-4-[(3R)-3-ethylpiperazin-1-yl]-2-fluoro-benzamide hydrochloride | tert-butyl (2R)-4-(4-carbamoyl-3-fluorophenyl)-2-ethyl-piperazine-1-carboxylate (B.13) and 6-bromo-8-cyclopropyl-2-methylimidazo[1,2-a]pyrazine (C.3) | 423.2 |

| Ex. No. | Structure | Systematic Name | Starting materials | MW (MH+) |
|---|---|---|---|---|
| 37 | 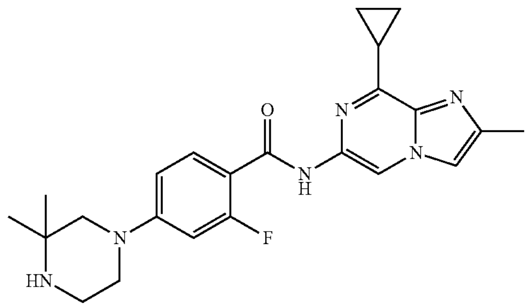 | N-(8-cyclopropyl-2-methylimidazo[1,2-a]pyrazin-6-yl)-4-(3,3-dimethyl-piperazin-1-yl)-2-fluoro-benzamide hydrochloride | tert-butyl 4-(4-carbamoyl-3-fluorophenyl)-2,2-dimethyl-piperazine-1-carboxylate (B.7) and 6-bromo-8-cyclopropyl-2-methylimidazo[1,2-a]pyrazine (C.3) | 423.3 |
| 38 | 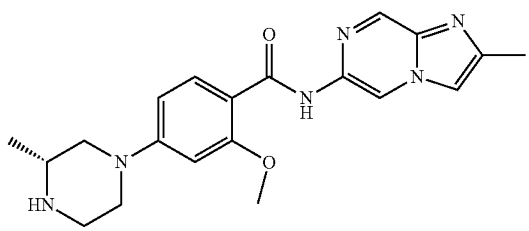 | 2-methoxy-N-(2-methyl-imidazo[1,2-a]pyrazin-6-yl)-4-[(3R)-3-methyl-piperazin-1-yl]benzamide | tert-butyl (2R)-4-(4-carbamoyl-3-methoxy-phenyl)-2-methyl-piperazine-1-carboxylate (B.2) and 6-bromo-2-methylimidazo[1,2-a]pyrazine | 381.2 |
| 39 | 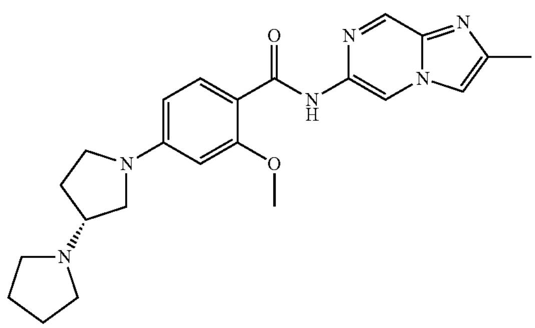 [SMILES: COc1cc(N2CC[C@@H](N3CCCC3)C2)ccc1C(=O)Nc1cn2cc(C)nc2cn1] | 2-methoxy-N-(2-methyl-imidazo[1,2-a]pyrazin-6-yl)-4-[(3R)-3-pyrrolidin-1-ylpyrrolidin-1-yl]benzamide | 2-methoxy-4-[(3R)-3-pyrrolidin-1-ylpyrrolidin-1-yl]benzamide (B.23) and 6-bromo-2-methylimidazo[1,2-a]pyrazine | 421.2 |
| 40 | 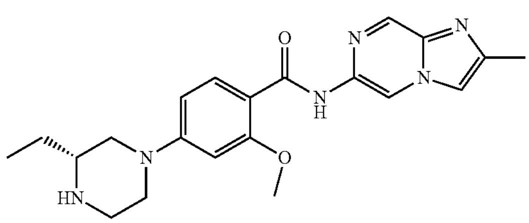 [SMILES: CC[C@@H]1CN(c2ccc(C(=O)Nc3cn4cc(C)nc4cn3)c(OC)c2)CCN1] | 4-[(3R)-3-ethylpiperazin-1-yl]-2-methoxy-N-(2-methylimidazo[1,2-a]pyrazin-6-yl)benzamide | tert-butyl (2R)-4-(4-carbamoyl-3-methoxy-phenyl)-2-ethylpiperazine-1-carboxylate (B.12) and 6-bromo-2-methylimidazo[1,2-a]pyrazine | 395.3 |
| 41 | 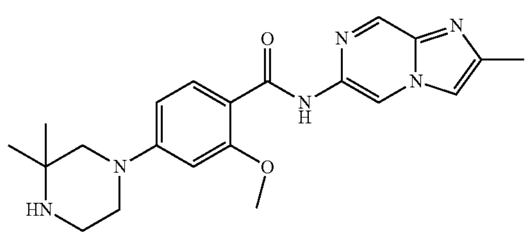 | 4-(3,3-dimethyl-piperazin-1-yl)-2-methoxy-N-(2-methyl-imidazo[1,2-a]pyrazin-6-yl)benzamide | tert-butyl 4-(4-carbamoyl-3-methoxyphenyl)-2,2-dimethyl-piperazine-1-carboxylate (B.8) and 6-bromo-2-methylimidazo[1,2-a]pyrazine | 395.3 |
| 42 | 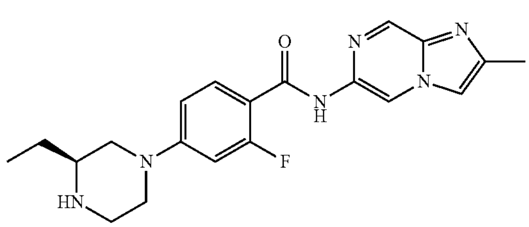 [SMILES: CC[C@H]1CN(c2ccc(C(=O)Nc3cn4cc(C)nc4cn3)c(F)c2)CCN1] | 4-[(3S)-3-ethylpiperazin-1-yl]-2-fluoro-N-(2-methyl-imidazo[1,2-a]pyrazin-6-yl)benzamide hydrochloride | tert-butyl (2S)-4-(4-carbamoyl-3-fluorophenyl)-2-ethyl-piperazine-1-carboxylate (B.11) and 6-bromo-2-methylimidazo[1,2-a]pyrazine | 383.2 |

-continued

| Ex. No. | Structure | Systematic Name | Starting materials | MW (MH+) |
|---|---|---|---|---|
| 43 | 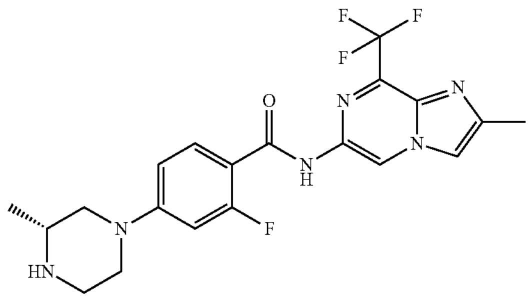 | 2-fluoro-4-[(3R)-3-methylpiperazin-1-yl]-N-[2-methyl-8-(trifluoromethyl)imidazo[1,2-a]pyrazin-6-yl]benzamide | tert-butyl (2R)-4-(4-carbamoyl-3-fluorophenyl)-2-methyl-piperazine-1-carboxylate (B.1) and 6-chloro-8-trifluoromethyl-2-methyl-imidazo[1,2-a]pyrazine (C.4) | 437.2 |
| 44 | 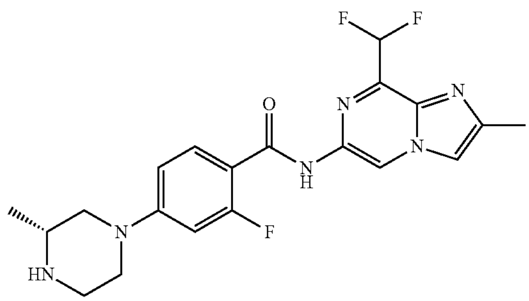 | N-[8-(difluoromethyl)-2-methyl-imidazo[1,2-a]pyrazin-6-yl]-2-fluoro-4-[(3R)-3-methyl-piperazin-1-yl]benzamide | tert-butyl (2R)-4-(4-carbamoyl-3-fluorophenyl)-2-methyl-piperazine-1-carboxylate (B.1) and 6-chloro-8-difluoromethyl-2-methyl-imidazo[1,2-a]pyrazine (C.5) | 419.2 |
| 45 | 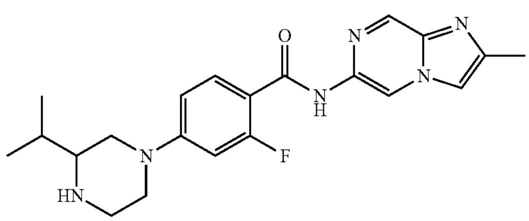 [SMILES: Cc1cn2cc(NC(=O)c3ccc(N4CCNC(C(C)C)C4)cc3F)ncc2n1] | 2-fluoro-N-(2-methylimidazo[1,2-a]pyrazin-6-yl)-4-(3-propan-2-yl-piperazin-1-yl)benzamide hydrochloride | tert-butyl 4-(4-carbamoyl-3-fluorophenyl)-2-isopropyl-piperazine-1-carboxylate (B.17) and 6-bromo-2-methylimidazo[1,2-a]pyrazine | 397.2 |
| 46 | 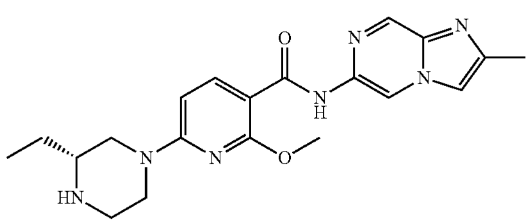 [SMILES: CC[C@@H]1CN(c2ccc(C(=O)Nc3cn4cc(C)nc4cn3)c(OC)n2)CCN1] | 6-[(3R)-3-ethylpiperazin-1-yl]-2-methoxy-N-(2-methylimidazo[1,2-a]pyrazin-6-yl)pyridine-3-carboxamide hydrochloride | tert-butyl (2R)-4-(5-carbamoyl-6-methoxy-pyridin-2-yl)-2-ethyl-piperazine-1-carboxylate (B.26) and 6-bromo-2-methylimidazo[1,2-a]pyrazine | 396.3 |
| 47 | 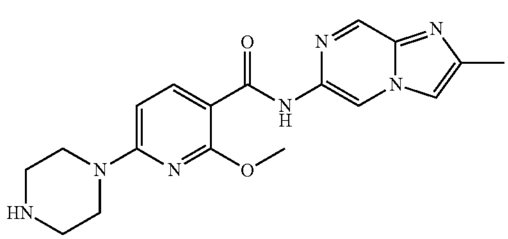 [SMILES: COc1nc(N2CCNCC2)ccc1C(=O)Nc1cn2cc(C)nc2cn1] | 2-methoxy-N-(2-methyl-imidazo[1,2-a]pyrazin-6-yl)-6-piperazin-1-ylpyridine-3-carboxamide hydrochlorid | tert-butyl 4-(5-carbamoyl-6-methoxypyridin-2-yl)piperazine-1-carboxylate (B.27) and 6-bromo-2-methylimidazo[1,2-a]pyrazine | 386.2 |

Example 48

Preparation of N-(2,8-dimethylimidazo[1,2-a]pyrazin-6-yl)-2-fluoro-4-(4-pyrrolidin-1-ylpiperidin-1-yl)benzamide

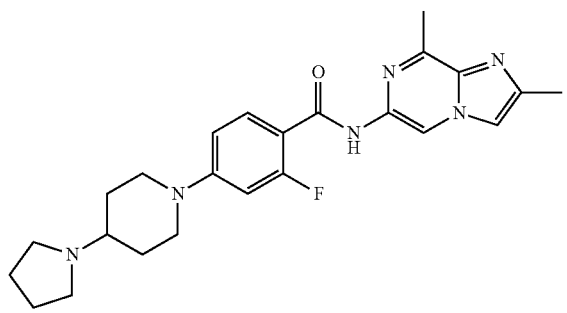 [SMILES: Cc1cn2cc(NC(=O)c3ccc(N4CCC(N5CCCC5)CC4)cc3F)nc(C)c2n1]

Step A:

2-Fluoro-4-(1,4-dioxa-8-azaspiro[4.5]decan-8-yl)benzamide (A.22) was reacted with -bromo-2,8-dimethylimidazo[1,2-a]pyrazine (C.1) in analogy to Example 1 to afford N-(2,8-dimethylimidazo[1,2-a]pyrazin-6-yl)-2-fluoro-4-(1,4-dioxa-8-azaspiro[4.5]decan-8-yl)benzamide. MS (m/e): 426.3 (M+H$^+$)

Step B:

N-(2,8-dimethylimidazo[1,2-a]pyrazin-6-yl)-2-fluoro-4-(1,4-dioxa-8-azaspiro[4.5]decan-8-yl)benzamide (0.14 g, 0.3 mmol) was dissolved in dioxane (2.5 ml) and aqueous 6M HCl (2.3 ml, 13.8 mmol) added. The mixture was stirred for 2 h, after which time it was neutralized by addition of saturated aqueous sodium hydrogen carbonate and extracted with EtOAc. The organic was washed with brine, dried (Na$_2$SO$_4$) and concentrated to afford N-(2,8-dimethylimidazo[1,2-a]pyrazin-6-yl)-2-fluoro-4-(4-oxopiperidin-1-yl)benzamide (0.13 g, quant) as a yellow powder.

Step C:

To a solution of N-(2,8-dimethylimidazo[1,2-a]pyrazin-6-yl)-2-fluoro-4-(4-oxopiperidin-1-yl)benzamide (0.12 g, 0.3 mmol) in DCM (2 ml) was added pyrollidine (0.03 ml, 0.4 mmol) followed by sodium triacetoxyborohydride (0.1 g, 0.5 mmol) and the reaction stirred for 0.5 h. The reaction was then diluted with EtOAc, washed with saturated aqueous sodium hydrogen carbonate, brine, dried (Na$_2$SO$_4$) and concentrated. Purification by flash column chromatography on silica gel (DCM: MeOH 9:1-7:3+NH4OH) to afford N-(2,8-dimethylimidazo[1,2-a]pyrazin-6-yl)-2-fluoro-4-(4-pyrrolidin-1-ylpiperidin-1-yl)benzamide (0.11 g, 82%) as a white powder. MS (m/e): 437.4 (M+H$^+$)

Example 49

N-(2,8-dimethylimidazo[1,2-a]pyrazin-6-yl)-2-ethoxy-4-[4-(3-methoxyazetidin-1-yl)piperidin-1-yl]benzamide

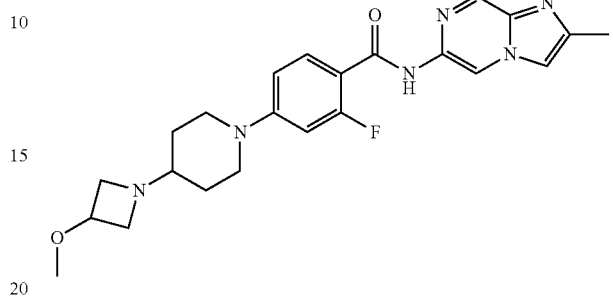

The title compound was prepared in analogy to Example 48 (Step C), by reaction of N-(2,8-dimethylimidazo[1,2-a]pyrazin-6-yl)-2-fluoro-4-(4-oxopiperidin-1-yl)benzamide (Example 48, Step B) with 3-methoxyazetidine hydrochloride. MS (m/e): 479.4 (M+H$^+$)

Biological Assays

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of formula (I) enhance inclusion of exon 7 of SMN2 into mRNA transcribed from the SMN2 gene and increase levels of SMN protein produced from the SMN2 gene, and thus can be used to treat SMA in a human subject in need thereof. These examples further illustrate the testing of certain compounds described herein in vitro and/or in vivo and demonstrate the usefulness of the compounds for enhancing the inclusion of exon 7 of SMN1 into mRNA transcribed from the SMN1 gene. Accordingly, compounds of formula (I) also enhance the inclusion of exon 7 of SMN1 into mRNA transcribed from the SMN1 gene and increase levels of SMN protein produced from the SMN1 gene.

Assay 1

RT-qPCR Assay for SMN2 Minigene Pre-mRNA Splicing in Cultured Cells

The reverse transcription-quantitative PCR-based (RT-qPCR) assay is used to quantify the level of the full length SMN2 minigene (referred to herein by the term "FL SMN2mini") mRNA containing SMN2 exon 7 in a HEK293H cell line stably transfected with said minigene and treated with a test compound. Materials used and respective sources are listed below in Table 1.

TABLE 1

Materials and their respective sources used in the SMN2 minigene mRNA splicing RT-qPCR assay in cultured cells.

| Material | Source |
|---|---|
| HEK293H cells | Thermo Fisher Scientific, Inc. (formerly Life Technologies, Inc.) Catalog No. 11631-017 |
| Cells-To-Ct lysis buffer | Thermo Fisher Scientific, Inc. (formerly Life Technologies, Inc.) part No. 4399002 |
| DMEM | Thermo Fisher Scientific, Inc. (formerly Life Technologies, Inc.) Catalog No. 11960-044 |
| 96-well flat-bottom plates | Becton Dickinson Catalog No. 353072 |
| RT-PCR Enzyme Mix | Thermo Fisher Scientific, Inc. (formerly Life Technologies, Inc.) part No. 4388520 |
| RT-PCR buffer | Thermo Fisher Scientific, Inc. (formerly Life Technologies, Inc.) part No. 4388519 |
| AgPath-ID One-Step RT-PCR kit | Thermo Fisher Scientific, Inc. (formerly Life Technologies, Inc.) part No. 4387391 |
| Thermocycler | Thermo Fisher Scientific, Inc. (formerly Life Technologies, Inc.) 7900HT |

The SMN2-A minigene construct was prepared as described in International Patent Application WO2009/151546A1 page 145 paragraph [00400] to page 147 paragraph [00412] (incl. FIG. 1 and FIG. 3 therein).

HEK293H cells stably transfected with the SMN2-A minigene construct (10,000 cells/well) are seeded in 200 μL of cell culture medium (DMEM plus 10% FBS, with 200 μg/mL hygromycin) in 96-well flat-bottom plates and the plate is immediately swirled to ensure proper dispersal of cells and the formation of an even monolayer of cells. Cells are allowed to attach for 6 hours. Test compounds are serially diluted 3.16-fold in 100% DMSO to generate a 7-point concentration curve. A solution of test compound (1 μL, 200× in DMSO) is added to each cell-containing well and the plate is incubated for 24 hours in a cell culture incubator (37° C., 5% CO$_2$, 100% relative humidity). 2 replicates are prepared for each test compound concentration. The cells are then lysed in the Cells-To-Ct lysis buffer and the lysate is stored at −80° C.

Full length SMN2-A minigene and GAPDH mRNA are quantified using the primers and probes referenced in Table 2. Primer SMN Forward A (SEQ ID NO.1) hybridizes to a nucleotide sequence in exon 7 (nucleotide 22 to nucleotide 40), primer SMN Reverse A (SEQ ID NO.2) hybridizes to a nucleotide sequence in the coding sequence of Firefly luciferase, SMN Probe A (SEQ ID NO.3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

TABLE 2

| Primers/Probes | Sequences | Source |
|---|---|---|
| SMN Forward Primer A | SEQ ID NO. 1:<br>GAAGGAAGGTGCTCACATT | PTC[1] |
| SMN Reverse Primer A | SEQ ID NO. 2:<br>TCTTTATGTTTTTGGCGTCTTC | PTC[1] |
| SMN Forward Probe A | SEQ ID NO. 3:<br>6FAM-AAGGAGAAATGCTGGCATAGAGCAGC-TAMRA | PTC[1] |
| hGAPDH Forward Probe | SEQ ID NO. 4:<br>VIC-CGCCTGGTCACCAGGGCTGCT-TAMRA | LTI[2] |
| hGAPDH Forward Primer | SEQ ID NO. 5:<br>CAACGGATTTGGTCGTATTGG | LTI[2] |
| hGAPDH Reverse Primer | SEQ ID NO. 6:<br>TGATGGCAACAATATCCACTTTACC | LTI[2] |

[1]Primers and probes designed by PTC Therapeutics, Inc.;
[2]Commercially available from Thermo Fisher Scientific, Inc. (formerly Life Technologies, Inc.).

The SMN forward and reverse primers are used at final concentrations of 0.4 μM. The SMN probe is used at a final concentration of 0.15 μM. The GAPDH primers are used at final concentrations of 0.2 μM and the probe at 0.15 μM.

The SMN2-minigene GAPDH mix (15 μL total volume) is prepared by combining 7.5 of 2×RT-PCR buffer, 0.4 μL of 25×RT-PCR enzyme mix, 0.75 μL of 20× GAPDH primer-probe mix, 4.0075 μL of water, 2 μL of 10-fold diluted cell lysate, 0.06 μL of 100 μM SMN forward primer, 0.06 μL of 100 μM SMN reverse primer, and 0.225 μL of 100 μM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

The increase in the abundance of the FL SMN2mini mRNA relative to that in cells treated with vehicle control is determined from real-time PCR data using a modified ΔΔCt method (as described in Livak and Schmittgen, *Methods*, 2001, 25:402-8). The amplification efficiency E is calculated from the slope of the amplification curve for FL SMN2mini and GAPDH individually. The abundance of FL SMN2mini and GAPDH mRNA are then calculated as $(1+E)^{-Ct}$, where Ct is the threshold value for each amplicon. The abundance of FL SMN2mini mRNA is normalized to GAPDH mRNA abundance. The normalized FL SMN2mini mRNA abundance from test compound-treated samples is then divided by normalized FL SMN2mini mRNA abundance from vehicle-treated cells to determine the level of FL SMN2mini mRNA relative to vehicle control.

Table 3 provides EC$_{1.5x}$ concentrations for production of full length SMN2 minigene mRNA that was obtained from the 7-point concentration data generated according to the above procedure for particular compounds of the present invention.

Particular compounds of the present invention exhibit an EC$_{1.5x}$ concentration for production of full length SMN2 minigene mRNA ≤5 μM.

More particular compounds of the present invention exhibit an EC$_{1.5x}$ concentration for production of full length SMN2 minigene mRNA ≤1 μM.

Most particular compounds of the present invention exhibit an EC1.5× concentration for production of full length SMN2 minigene mRNA ≤0.1 μM.

TABLE 3

EC$_{1.5x}$ concentrations for production of full length SMN2 minigene mRNA.

| Example | EC$_{1.5x}$ minigene [nM] |
|---|---|
| 1 | 37.4 |
| 2 | 1045.4 |
| 3 | 102.5 |
| 4 | 26.3 |
| 5 | 41 |
| 6 | 100.6 |
| 7 | 48.4 |
| 8 | 40.7 |
| 9 | 98 |
| 10 | 38.3 |
| 11 | 16.4 |
| 12 | 145 |
| 13 | 26.2 |
| 14 | 9.7 |
| 15 | 38 |
| 16 | 31.4 |
| 17 | 33.8 |
| 18 | 23.4 |
| 19 | 3 |
| 20 | 23 |
| 21 | 20.4 |
| 22 | 95.2 |
| 23 | 26.8 |
| 24 | 51 |
| 25 | 14.6 |
| 26 | 59.6 |
| 27 | 16.7 |
| 28 | 2028.5 |
| 29 | 85.2 |
| 30 | 165 |
| 31 | 35.8 |
| 32 | 26.8 |
| 33 | 22.2 |
| 34 | 214 |
| 35 | 31.7 |
| 36 | 53.4 |
| 37 | 31.7 |
| 38 | 57.8 |
| 39 | 118.3 |
| 40 | 38 |
| 41 | 46.4 |
| 42 | 14.4 |
| 43 | 40 |
| 44 | 9.5 |
| 45 | 106.1 |
| 46 | 189.2 |
| 47 | 128.9 |
| 48 | 26.6 |
| 49 | 223.1 |

Assay 2

SMN Protein Assay in Cultured Cells

The SMN HTRF (homogeneous time resolved fluorescence) assay is used to quantify the level of SMN protein in SMA patient fibroblast cells treated with test compounds. Materials used and respective sources are listed below in Table 4.

TABLE 4

Materials and their respective sources used in the SMN protein assay in cultured cells.

| Material | Source |
|---|---|
| SMA Type 1 human cells | GM03813 (Coriell Institute) |
| Protease inhibitor cocktail | Roche Applied Science Catalog No. 11836145001 |
| Anti-SMN d2 | Blue cap Cisbio Catalog No. 63IDC002-SMN |
| Anti-SMN cryptate | Red cap Cisbio Catalog No. 63IDC002-SMN |
| SMN reconstitution buffer | Cisbio Catalog No. 63IDC002-SMN-Buffer |
| DMEM | Thermo Fisher Scientific, Inc. (formerly Life Technologies, Inc.) Catalog No. 11960-044 |
| RIPA Lysis Buffer | 20 mM Tris-HCl pH 7.5, 150 mM NaCl, 1 mM EDTA, 1% Thermo Scientific NP-40 Surfact-Amps Detergent Solution (Thermo Fisher Scientific, Inc., formerly Fisher Scientific, Pittsburgh/PA), 1% Sodium deoxycholate |
| Diluent Buffer | 20 mM Tris-HCl pH 7.5, 150 mM NaCl |
| Envision Plate Reader | Perkin Elmer Model # 2103 |

Cells are thawed and cultured in DMEM-10% FBS for 72 hours. Cells are trypsinized, counted and re-suspended to a concentration of 25,000 cells/mL in DMEM-10% FBS. The cell suspensions are plated at 5,000 cells per well in a 96 well microtiter plate and incubated for 3 to 5 hours. Test compounds are serially diluted 3.16-fold in 100% DMSO to generate a 7-point concentration curve. 1 µL of test compound solution is transferred to cell-containing wells and cells are incubated for 48 hours in a cell culture incubator (37° C., 5% CO$_2$, 100% relative humidity). Triplicate samples are set up for each test compound concentration. After 48 hours, the supernatant is removed from the wells and 25 µL of the RIPA lysis buffer, containing protease inhibitors, is added to the wells and incubated with shaking at room temperature for 1 hour. 25 µL of the diluent is added and then 35 µL of the resulting lysate is transferred to a 384-well plate, where each well contains 5 µL of the antibody solution (1:100 dilution of anti-SMN d2 and anti-SMN cryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of SMN protein abundance as a percent value) for each sample well is calculated by subtracting the normalized average fluorescence for the Blank control wells from the normalized fluorescence for each sample well, then dividing this difference by the normalized average fluorescence for the Blank control wells and multiplying the resulting value by 100. The ΔF value for each sample well represents the SMN protein abundance from test compound-treated samples. The ΔF value for each sample well is divided by the ΔF value for the vehicle control wells to calculate the fold increase in SMN protein abundance relative to the vehicle control. Table 5 provides $EC_{1.5x}$ concentrations for SMN protein expression that was obtained from the 7-point concentration data generated according to the above procedure for particular compounds of the present invention.

Particular compounds of the present invention exhibit an $EC_{1.5x}$ concentration for SMN protein expression ≤10 μM.

More particular compounds of the present invention exhibit an $EC_{1.5x}$ concentration for SMN protein expression ≤1000 nM.

Most particular compounds of the present invention exhibit an $EC_{1.5x}$ concentration for SMN protein expression ≤500 nM.

Table 6 provides the maximum fold increase of SMN protein that was obtained from the 7-point concentration data generated according to the above procedure for particular compounds of the present invention Particular compounds of the present invention exhibit a maximum fold increase >1.5.

More particular compounds of the present invention exhibit a maximum fold increase >1.7. Most particular compounds of the present invention exhibit a maximum fold increase >1.8.

TABLE 5

$EC_{1.5x}$ concentrations for SMN protein expression.

| Example | $EC_{1.5x}$ SMN protein (nM) |
|---|---|
| 1 | 87 |
| 2 | 2248.9 |
| 3 | 409.4 |
| 4 | 122 |
| 5 | 185.3 |
| 6 | 428.5 |
| 7 | 872.2 |
| 8 | 351.5 |
| 9 | 344.9 |
| 10 | 130.4 |
| 11 | 52.2 |
| 12 | 1734.9 |
| 13 | 108.7 |
| 14 | 124 |
| 15 | 303.2 |
| 16 | 237.2 |
| 17 | 1700.2 |
| 18 | 116.8 |
| 19 | 27.4 |
| 20 | 100.6 |
| 21 | 162.4 |
| 22 | 660 |
| 23 | 62.2 |
| 24 | 113.4 |
| 25 | 122.8 |
| 26 | 1608.8 |
| 27 | 1523.7 |
| 28 | 8764.8 |
| 29 | 495.3 |
| 30 | 603 |
| 31 | 221 |
| 32 | 125.9 |
| 33 | 121.9 |
| 34 | 1253.3 |
| 35 | 504.6 |
| 36 | 1091.1 |
| 37 | 286.9 |
| 38 | 206.1 |
| 39 | 378.6 |
| 40 | 387.6 |
| 41 | 242.5 |
| 42 | 230.6 |
| 43 | 87 |
| 44 | 35 |

TABLE 5-continued $EC_{1.5x}$ concentrations for SMN protein expression.

| Example | $EC_{1.5x}$ SMN protein (nM) |
|---|---|
| 45 | 264.4 |
| 46 | 579.5 |
| 47 | 551 |
| 48 | 230 |
| 49 | 1977.8 |

TABLE 6

Maximum fold increase of SMN protein.

| Example | Max. fold increase |
|---|---|
| 1 | 1.90 |
| 2 | 1.74 |
| 3 | 1.83 |
| 4 | 1.92 |
| 5 | 1.90 |
| 6 | 1.71 |
| 7 | 1.64 |
| 8 | 1.77 |
| 9 | 1.73 |
| 10 | 1.91 |
| 11 | 1.80 |
| 12 | 1.56 |
| 13 | 1.66 |
| 14 | 1.61 |
| 15 | 1.72 |
| 16 | 1.72 |
| 17 | 1.51 |
| 18 | 1.75 |
| 19 | 1.71 |
| 20 | 1.70 |
| 21 | 1.80 |
| 22 | 1.50 |
| 23 | 1.72 |
| 24 | 1.75 |
| 25 | 1.88 |
| 26 | 1.57 |
| 27 | 1.85 |
| 28 | 1.65 |
| 29 | 1.91 |
| 30 | 1.82 |
| 31 | 1.87 |
| 32 | 1.81 |
| 33 | 1.78 |
| 34 | 1.69 |
| 35 | 2.16 |
| 36 | 1.53 |
| 37 | 1.72 |
| 38 | 1.74 |
| 39 | 1.75 |
| 40 | 1.93 |
| 41 | 2.05 |
| 42 | 1.72 |
| 43 | 1.76 |
| 44 | 1.79 |
| 45 | 1.76 |
| 46 | 1.67 |
| 47 | 1.64 |
| 48 | 1.65 |
| 49 | 1.51 |

The invention claimed is:

1. A compound of formula (I):

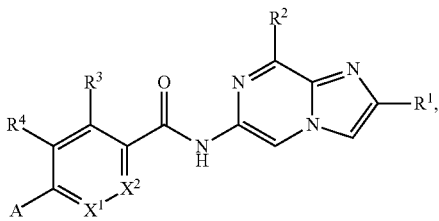

or a pharmaceutically acceptable salt thereof, wherein
$X^1$ is $CR^5$ or N;
$X^2$ is $CR^5$ or N; with the proviso that not both $X^1$ and $X^2$ are N;
$R^1$ is hydrogen or $C_{1-7}$-alkyl;
$R^2$ is hydrogen, cyano, $C_{1-7}$-alkyl, $C_{1-7}$-haloalkyl or $C_{3-8}$-cycloalkyl;
$R^3$ is hydrogen, halo, $C_{1-7}$-alkyl, or $C_{1-7}$-alkoxy;
$R^4$ is hydrogen, halo, $C_{1-7}$-alkyl, or $C_{1-7}$-alkoxy;
$R^5$ is independently selected from hydrogen, halo, $C_{1-7}$-alkyl, or $C_{1-7}$-alkoxy;
A is N-heterocycloalkyl or $NR^7R^8$, wherein N-heterocycloalkyl comprises 1 or 2 nitrogen ring atoms and is optionally substituted with 1, 2, 3 or 4 substituents selected from $R^6$;
$R^6$ is independently selected from hydrogen, $C_{1-7}$-alkyl, amino, amino-$C_{1-7}$-alkyl, $C_3$-8-cycloalkyl, heterocycloalkyl and $C_{1-7}$-alkoxy-heterocycloalkyl or two $R^6$ together form $C_{1-7}$-alkylene;
$R^7$ is heterocycloalkyl comprising 1 nitrogen ring atom, wherein heterocycloalkyl is optionally substituted with 1, 2, 3 or 4 substituents selected from $R^6$; and
$R^8$ is hydrogen, $C_{1-7}$-alkyl or $C_{3-8}$-cycloalkyl;
with the proviso that if A is N-heterocycloalkyl which comprises only 1 nitrogen ring atom, then A is substituted with 1, 2, 3 or 4 substituents selected from the group consisting of amino or amino-$C_{1-7}$-alkyl.

2. The compound according to claim 1, or a pharmaceutically acceptable salt thereof, wherein
$X^1$ is CH or N;
$X^2$ is $CR^5$;
$R^1$ is $C_{1-7}$-alkyl;
$R^2$ is hydrogen, $C_{1-7}$-alkyl, $C_{1-7}$-haloalkyl or $C_{3-8}$-cycloalkyl;
A is N-heterocycloalkyl, wherein N-heterocycloalkyl comprises 1 or 2 nitrogen ring atoms and is optionally substituted with 1, 2, 3 or 4 substituents selected from $R^6$; and
$R^6$ is independently selected from hydrogen, $C_{1-7}$-alkyl, amino, amino-$C_{1-7}$-alkyl, $C_{3-8}$-cycloalkyl, heterocycloalkyl and $C_{1-7}$-alkoxy-heterocycloalkyl or two $R^6$ together form $C_{1-7}$-alkylene
with the proviso that if A is N-heterocycloalkyl which comprises only 1 nitrogen ring atom, then A is substituted with 1, 2, 3 or 4 substituents selected from the group consisting of amino or amino-$C_{1-7}$-alkyl.

3. The compound according to claim 1, or a pharmaceutically acceptable salt thereof, wherein

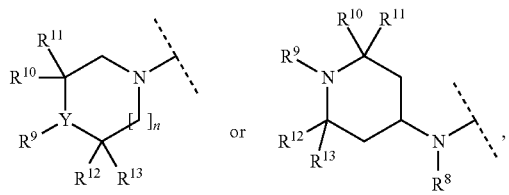

A is wherein
Y is N or CH;
$R^9$ is hydrogen, $C_{1-7}$-alkyl, or $-(CH_2)_m-NR^{14}R^{15}$;
$R^{10}$ is hydrogen or $C_{1-7}$-alkyl;
$R^{11}$ is hydrogen or $C_{1-7}$-alkyl;
$R^{12}$ is hydrogen or $C_{1-7}$-alkyl;
$R^{13}$ is hydrogen or $C_{1-7}$-alkyl;
$R^{14}$ and $R^{15}$ are independently selected from hydrogen, $C_{1-7}$-alkyl and $C_{3-8}$-cycloalkyl;
n is 0, 1 or 2;
m is 0, 1, 2 or 3;
or $R^9$ and $R^{10}$ together form $C_{1-7}$-alkylene;
or $R^9$ and $R^{12}$ together form $C_{1-7}$-alkylene;
or $R^{10}$ and $R^{11}$ together form $C_{2-7}$-alkylene;
or $R^{10}$ and $R^{12}$ together form $C_{1-7}$-alkylene;
or $R^{10}$ and $R^{14}$ together form $C_{1-7}$-alkylene;
or $R^{12}$ and $R^{13}$ together form $C_{2-7}$-alkylene;
or $R^{12}$ and $R^{14}$ together form $C_{1-7}$-alkylene;
or $R^{14}$ and $R^{15}$ together form $C_{2-7}$-alkylene which is optionally substituted with alkoxy;
with the proviso that if Y is CH then $R^9$ is $-(CH_2)_m-NR^{14}R^{15}$; and
with the proviso that if Y is N and $R^9$ is $-(CH_2)_m-NR^{14}R^{15}$, then m is 2 or 3.

4. The compound according to claim 3, or a pharmaceutically acceptable salt thereof, wherein Y is CH and $R^9$ is $-(CH_2)_m-NR^{14}R^{15}$.

5. The compound according to claim 3, or a pharmaceutically acceptable salt thereof, wherein $R^9$ is hydrogen, pyrrolidinyl, or methoxy-azetidinyl.

6. The compound according to claim 3, or a pharmaceutically acceptable salt thereof, wherein $R^{10}$ is hydrogen, methyl, ethyl or isopropyl.

7. The compound according to claim 3, or a pharmaceutically acceptable salt thereof, wherein $R^9$ and $R^{10}$ together form propylene.

8. The compound according to claim 3, or a pharmaceutically acceptable salt thereof, wherein $R^{10}$ and $R^{11}$ together form ethylene.

9. The compound according to claim 3, or a pharmaceutically acceptable salt thereof, wherein $R^{14}$ and $R^{15}$ together form propylene or butylene.

10. The compound according to claim 3, or a pharmaceutically acceptable salt thereof, wherein A is selected from the group of:

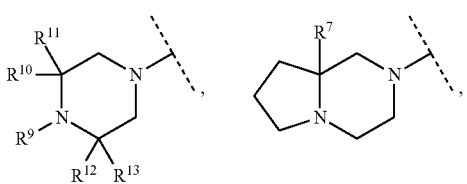

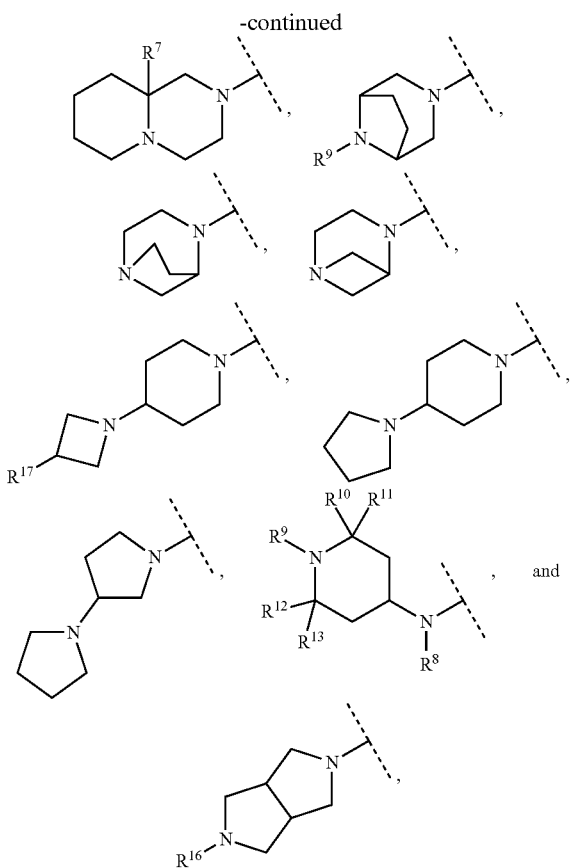

wherein R¹⁶ is hydrogen or $C_{1-7}$-alkyl and R¹⁷ is $C_{1-7}$-alkoxy.

11. The compound according to claim 3, or a pharmaceutically acceptable salt thereof, wherein A is selected from the group of:

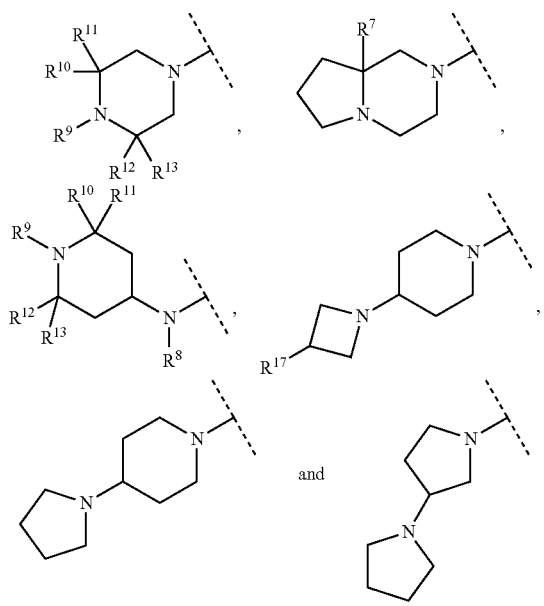

wherein R¹⁷ is $C_{1-7}$-alkoxy.

12. The compound according to claim 3, or a pharmaceutically acceptable salt thereof, wherein A is

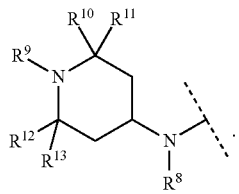

13. The compound according to claim 1, or a pharmaceutically acceptable salt thereof, wherein A is piperazinyl, diazepanyl, pyrrolidinyl or hexahydropyrrolo[1,2-a]pyrazinyl, each optionally substituted with 1, 2, 3 or 4 substituents selected from R⁶.

14. The compound according to claim 1, or a pharmaceutically acceptable salt thereof, wherein A is NR⁷R⁸.

15. The compound according to claim 1, or a pharmaceutically acceptable salt thereof, wherein the compound is selected from the group consisting of:
  2-fluoro-N-(2-methylimidazo[1,2-a]pyrazin-6-yl)-4-piperazin-1-ylbenzamide;
  N-(2-methylimidazo[1,2-a]pyrazin-6-yl)-4-piperazin-1-ylbenzamide;
  4-[(8aS)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
  2-ethoxy-N-(2-methylimidazo[1,2-a]pyrazin-6-yl)-4-[(3S)-3-methylpiperazin-1-yl]benzamide;
  2-ethoxy-N-(2-methylimidazo[1,2-a]pyrazin-6-yl)-4-[(3R)-3-methylpiperazin-1-yl]benzamide;
  4-[(8aR)-3,4,6,7,8,8a-hexahydro-1H-pyrrolo[1,2-a]pyrazin-2-yl]-2-ethoxy-N-(2-methylimidazo[1,2-a]pyrazin-6-yl)benzamide;
  4-[(8aR)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
  4-[(8aS)-3,4,6,7,8,8a-hexahydro-1H-pyrrolo[1,2-a]pyrazin-2-yl]-2-fluoro-N-(2-methylimidazo[1,2-a]pyrazin-6-yl)benzamide;
  4-(1,4-diazepan-1-yl)-2-ethoxy-N-(2-methylimidazo[1,2-a]pyrazin-6-yl)benzamide;
  4-[(3S,5R)-3,5-dimethylpiperazin-1-yl]-2-ethoxy-N-(2-methylimidazo[1,2-a]pyrazin-6-yl)benzamide;
  N-(2,8-dimethylimidazo[1,2-a]pyrazin-6-yl)-2-fluoro-4-[(3R)-3-methylpiperazin-1-yl]benzamide;
  4-[(8aS)-3,4,6,7,8,8a-hexahydro-1H-pyrrolo[1,2-a]pyrazin-2-yl]-N-(2,8-dimethylimidazo[1,2-a]pyrazin-6-yl)-2-ethoxybenzamide;
  4-[(8aS)-3,4,6,7,8,8a-hexahydro-1H-pyrrolo[1,2-a]pyrazin-2-yl]-N-(2,8-dimethylimidazo[1,2-a]pyrazin-6-yl)-2-fluorobenzamide;
  N-(2,8-dimethylimidazo[1,2-a]pyrazin-6-yl)-2,6-difluoro-4-[(3R)-3-methylpiperazin-1-yl]benzamide;
  N-(2,8-dimethylimidazo[1,2-a]pyrazin-6-yl)-2-ethoxy-4-[(3R)-3-methylpiperazin-1-yl]benzamide;
  4-[(8aS)-3,4,6,7,8,8a-hexahydro-1H-pyrrolo[1,2-a]pyrazin-2-yl]-N-(8-ethyl-2-methylimidazo[1,2-a]pyrazin-6-yl)-2-fluorobenzamide;
  4-[(8aS)-3,4,6,7,8,8a-hexahydro-1H-pyrrolo[1,2-a]pyrazin-2-yl]-N-(8-cyclopropyl-2-methylimidazo[1,2-a]pyrazin-6-yl)-2-fluorobenzamide;

4-[(8aS)-3,4,6,7,8,8a-hexahydro-1H-pyrrolo[1,2-a]
pyrazin-2-yl]-N-(2, 8-dimethylimidazo[1,2-a]pyrazin-6-yl)-2,6-difluorobenzamide;

N-(2,8-dimethylimidazo[1,2-a]pyrazin-6-yl)-4-[(3R, 5S)-3,5-dimethylpiperazin-1-yl]-2-fluorobenzamide;

N-(2,8-dimethylimidazo[1,2-a]pyrazin-6-yl)-2-fluoro-4-[(3S)-3-pyrrolidin-1-ylpyrrolidin-1-yl]benzamide;

N-(8-ethyl-2-methylimidazo[1,2-a]pyrazin-6-yl)-2-fluoro-4-[(3R)-3-methylpiperazin-1-yl]benzamide;

4-[(8aR)-3,4,6,7,8,8a-hexahydro-1H-pyrrolo[1,2-a]
pyrazin-2-yl]-N-(8-cyclopropyl-2-methylimidazo[1,2-a]pyrazin-6-yl)-2-fluorobenzamide;

N-(8-cyclopropyl-2-methylimidazo[1,2-a]pyrazin-6-yl)-2-fluoro-4-[(3R)-3-methylpiperazin-1-yl]benzamide;

2-fluoro-N-(2-methylimidazo[1,2-a]pyrazin-6-yl)-4-[(3S)-3-pyrrolidin-1-ylpyrrolidin-1-yl]benzamide;

2-fluoro-N-(2-methylimidazo[1,2-a]pyrazin-6-yl)-4-[(3R)-3-methylpiperazin-1-yl]benzamide;

4-(4,7-diazaspiro[2.5]octan-7-yl)-2-fluoro-N-(2-methylimidazo[1,2-a]pyrazin-6-yl)benzamide;

4-[(3 S,5R)-3,5-dimethylpiperazin-1-yl]-2-fluoro-N-(2-methylimidazo[1,2-a]pyrazin-6-yl)benzamide;

2-chloro-6-fluoro-N-(2-methylimidazo[1,2-a]pyrazin-6-yl)-4-piperazin-1-ylbenzamide;

2,5-difluoro-N-(2-methylimidazo[1,2-a]pyrazin-6-yl)-4-(3-methylpiperazin-1-yl)benzamide;

2,3-difluoro-N-(2-methylimidazo[1,2-a]pyrazin-6-yl)-4-(3-methylpiperazin-1-yl)benzamide;

4-[(3R,5S)-3,5-dimethylpiperazin-1-yl]-2-methoxy-N-(2-methylimidazo[1,2-a]pyrazin-6-yl)benzamide;

4-[(3R)-3-ethylpiperazin-1-yl]-2-fluoro-N-(2-methylimidazo[1,2-a]pyrazin-6-yl)benzamide;

2-fluoro-N-(2-methylimidazo[1,2-a]pyrazin-6-yl)-4-[(3R)-3-pyrrolidin-1-ylpyrrolidin-1-yl]benzamide;

4-(4,7-diazaspiro[2.5]octan-7-yl)-2-methoxy-N-(2-methylimidazo[1,2-a]pyrazin-6-yl)benzamide;

4-(3,3-dimethylpiperazin-1-yl)-2-fluoro-N-(2-methylimidazo[1,2-a]pyrazin-6-yl)benzamide;

N-(8-cyclopropyl-2-methylimidazo[1,2-a]pyrazin-6-yl)-4-[(3R)-3-ethylpiperazin-1-yl]-2-fluorobenzamide;

N-(8-cyclopropyl-2-methylimidazo[1,2-a]pyrazin-6-yl)-4-(3,3-dimethylpiperazin-1-yl)-2-fluorobenzamide;

2-methoxy-N-(2-methylimidazo[1,2-a]pyrazin-6-yl)-4-[(3R)-3-methylpiperazin-1-yl]benzamide;

2-methoxy-N-(2-methylimidazo[1,2-a]pyrazin-6-yl)-4-[(3R)-3-pyrrolidin-1-ylpyrrolidin-1-yl]benzamide;

4-[(3R)-3-ethylpiperazin-1-yl]-2-methoxy-N-(2-methylimidazo[1,2-a]pyrazin-6-yl)benzamide;

4-(3,3-dimethylpiperazin-1-yl)-2-methoxy-N-(2-methylimidazo[1,2-a]pyrazin-6-yl)benzamide;

4-[(3S)-3-ethylpiperazin-1-yl]-2-fluoro-N-(2-methylimidazo[1,2-a]pyrazin-6-yl)benzamide;

2-fluoro-4-[(3R)-3-methylpiperazin-1-yl]-N-[2-methyl-8-(trifluoromethyl)imidazo[1,2-a]pyrazin-6-yl]benzamide;

N-[8-(difluoromethyl)-2-methylimidazo[1,2-a]pyrazin-6-yl]-2-fluoro-4-[(3R)-3-methylpiperazin-1-yl]benzamide;

2-fluoro-N-(2-methylimidazo[1,2-a]pyrazin-6-yl)-4-(3-propan-2-ylpiperazin-1-yl)benzamide;

6-[(3R)-3-ethylpiperazin-1-yl]-2-methoxy-N-(2-methylimidazo[1,2-a]pyrazin-6-yl)pyridine-3-carboxamide;

2-methoxy-N-(2-methylimidazo[1,2-a]pyrazin-6-yl)-6-piperazin-1-ylpyridine-3-carboxamide;

N-(2,8-dimethylimidazo[1,2-a]pyrazin-6-yl)-2-fluoro-4-(4-pyrrolidin-1-ylpiperidin-1-yl)benzamide; and N-(2,8-dimethylimidazo[1,2-a]pyrazin-6-yl)-2-ethoxy-4-[4-(3-methoxyazetidin-1-yl)piperidin-1-yl]benzamide.

16. The compound according to claim 1, or a pharmaceutically acceptable salt thereof, wherein the compound is selected from the group consisting of:

4-(4,7-diazaspiro[2.5]octan-7-yl)-2-fluoro-N-(2-methylimidazo[1,2-a]pyrazin-6-yl)benzamide;

4-[(3 S,5R)-3,5-dimethylpiperazin-1-yl]-2-fluoro-N-(2-methylimidazo[1,2-a]pyrazin-6-yl)benzamide;

4-[(3R)-3-ethylpiperazin-1-yl]-2-fluoro-N-(2-methylimidazo[1,2-a]pyrazin-6-yl)benzamide;

2-fluoro-N-(2-methylimidazo[1,2-a]pyrazin-6-yl)-4-[(3R)-3-pyrrolidin-1-ylpyrrolidin-1-yl]benzamide;

4-[(3S)-3-ethylpiperazin-1-yl]-2-fluoro-N-(2-methylimidazo[1,2-a]pyrazin-6-yl)benzamide;

2-fluoro-4-[(3R)-3-methylpiperazin-1-yl]-N-[2-methyl-8-(trifluoromethyl)imidazo[a]pyrazin-6-yl]benzamide;

2-fluoro-N-(2-methylimidazo[1,2-a]pyrazin-6-yl)-4-piperazin-1-ylbenzamide;

4-[(8aS)-3,4,6,7,8,8a-hexahydro-1H-pyrrolo[1,2-a]
pyrazin-2-yl]-2-ethoxy-N-(2-methylimidazo[1,2-a]pyrazin-6-yl)benzamide;

2-ethoxy-N-(2-methylimidazo[1,2-a]pyrazin-6-yl)-4-[(3S)-3-methylpiperazin-1-yl]benzamide;

2-ethoxy-N-(2-methylimidazo[1,2-a]pyrazin-6-yl)-4-[(3R)-3-methylpiperazin-1-yl]benzamide;

4-[(8aR)-3,4,6,7,8,8a-hexahydro-1H-pyrrolo[1,2-a]
pyrazin-2-yl]-2-ethoxy-N-(2-methylimidazo[1,2-a]pyrazin-6-yl)benzamide;

4-[(8aR)-3,4,6,7,8,8a-hexahydro-1H-pyrrolo[1,2-a]
pyrazin-2-yl]-2-fluoro-N-(2-methylimidazo[1,2-a]pyrazin-6-yl)benzamide;

4-[(8aS)-3,4,6,7,8,8a-hexahydro-1H-pyrrolo[1,2-a]
pyrazin-2-yl]-2-fluoro-N-(2-methylimidazo[1,2-a]pyrazin-6-yl)benzamide;

4-(1,4-diazepan-1-yl)-2-ethoxy-N-(2-methylimidazo[1,2-a]pyrazin-6-yl)benzamide;

4-[(3 S,5R)-3,5-dimethylpiperazin-1-yl]-2-ethoxy-N-(2-methylimidazo[1,2-a]pyrazin-6-yl)benzamide;

2-fluoro-N-(2-methylimidazo[1,2-a]pyrazin-6-yl)-4-[(3S)-3-pyrrolidin-1-ylpyrrolidin-1-yl]benzamide;

2-fluoro-N-(2-methylimidazo[1,2-a]pyrazin-6-yl)-4-[(3R)-3-methylpiperazin-1-yl]benzamide;

2-chloro-6-fluoro-N-(2-methylimidazo[1,2-a]pyrazin-6-yl)-4-piperazin-1-ylbenzamide;

2,5-difluoro-N-(2-methylimidazo[1,2-a]pyrazin-6-yl)-4-(3-methylpiperazin-1-yl)benzamide;

2,3-difluoro-N-(2-methylimidazo[1,2-a]pyrazin-6-yl)-4-(3-methylpiperazin-1-yl)benzamide;

4-[(3R,5S)-3,5-dimethylpiperazin-1-yl]-2-methoxy-N-(2-methylimidazo[1,2-a]pyrazin-6-yl)benzamide;

4-(4,7-diazaspiro[2.5]octan-7-yl)-2-methoxy-N-(2-methylimidazo[1,2-a]pyrazin-6-yl)benzamide;

4-(3,3-dimethylpiperazin-1-yl)-2-fluoro-N-(2-methylimidazo[1,2-a]pyrazin-6-yl)benzamide;

2-methoxy-N-(2-methylimidazo[1,2-a]pyrazin-6-yl)-4-[(3R)-3-methylpiperazin-1-yl]benzamide;

2-m ethoxy-N-(2-methylimidazo[1,2-a]pyrazin-6-yl)-4-[(3R)-3-pyrrolidin-1-ylpyrrolidin-1-yl]benzamide;

4-[(3R)-3-ethylpiperazin-1-yl]-2-methoxy-N-(2-methylimidazo[1,2-a]pyrazin-6-yl)benzamide;

4-(3,3-dimethylpiperazin-1-yl)-2-m ethoxy-N-(2-methylimidazo[1,2-a]pyrazin-6-yl)benzamide;

N-[8-(difluoromethyl)-2-methylimidazo[1,2-a]pyrazin-6-yl]-2-fluoro-4-[(3R)-3-methylpiperazin-1-yl]benzamide;

2-fluoro-N-(2-methylimidazo[1,2-a]pyrazin-6-yl)-4-(3-propan-2-ylpiperazin-1-yl)benzamide;

6-[(3R)-3-ethylpiperazin-1-yl]-2-methoxy-N-(2-methylimidazo[1,2-a]pyrazin-6-yl)pyridine-3-carboxamide; and 2-methoxy-N-(2-methylimidazo[1,2-a]pyrazin-6-yl)-6-piperazin-1-ylpyridine-3-carboxamide.

17. The compound according to claim 1, or a pharmaceutically acceptable salt thereof, wherein the compound is selected from the group consisting of:

4-(4,7-diazaspiro[2.5]octan-7-yl)-2-fluoro-N-(2-methylimidazo[1,2-a]pyrazin-6-yl)benzamide;

4-[(3S,5R)-3,5-dimethylpiperazin-1-yl]-2-fluoro-N-(2-methylimidazo[1,2-a]pyrazin-6-yl)benzamide;

4-[(3R)-3-ethylpiperazin-1-yl]-2-fluoro-N-(2-methylimidazo[1,2-a]pyrazin-6-yl)benzamide;

2-fluoro-N-(2-methylimidazo[1,2-a]pyrazin-6-yl)-4-[(3R)-3-pyrrolidin-1-ylpyrrolidin-1-yl]benzamide;

4-[(3S)-3-ethylpiperazin-1-yl]-2-fluoro-N-(2-methylimidazo[1,2-a]pyrazin-6-yl)benzamide; and 2-fluoro-4-[(3R)-3-methylpiperazin-1-yl]-N-[2-methyl-8-(trifluoromethyl)imidazo[1,2-a]pyrazin-6-yl]benzamide.

18. A pharmaceutical composition comprising a compound according to claim 1, or a pharmaceutically acceptable salt thereof, and one or more pharmaceutically acceptable excipients.

19. A method for the treatment of spinal muscular atrophy in a human, which method comprises administering a therapeutically effective amount of a compound according to claim 1, or a pharmaceutically acceptable salt thereof, to a human in need of such treatment.

20. A method for the treatment of spinal muscular atrophy in a human, which method comprises administering a therapeutically effective amount of a compound according to claim 3, or a pharmaceutically acceptable salt thereof, to a human in need of such treatment.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: SMN Forward Primer A

<400> SEQUENCE: 1
gaaggaaggt gctcacatt                                               19

<210> SEQ ID NO 2
<211> LENGTH: 22
<212> TYPE: DNA
<213> ORGANISM: Artificial Sequence
<220> FEATURE:
<223> OTHER INFORMATION: SMN Reverse Primer A

<400> SEQUENCE: 2
tctttatgtt tttggcgtct tc                                           22

<210> SEQ ID NO 3
<211> LENGTH: 26
<212> TYPE: DNA
<213> ORGANISM: Artificial Sequence
<220> FEATURE:
<223> OTHER INFORMATION: SMN Forward Probe A

<400> SEQUENCE: 3
aaggagaaat gctggcatag agcagc                                       26

<210> SEQ ID NO 4
<211> LENGTH: 21
<212> TYPE: DNA
<213> ORGANISM: Artificial Sequence
<220> FEATURE:
<223> OTHER INFORMATION: hGAPDH Forward Probe

<400> SEQUENCE: 4
cgcctggtca ccagggctgc t                                            21

<210> SEQ ID NO 5
<211> LENGTH: 21
<212> TYPE: DNA
<213> ORGANISM: Artificial Sequence
<220> FEATURE:
<223> OTHER INFORMATION: hGAPDH Forward Primer

<400> SEQUENCE: 5
caacggattt ggtcgtattg g                                            21

<210> SEQ ID NO 6
<211> LENGTH: 25
<212> TYPE: DNA
<213> ORGANISM: Artificial Sequence
<220> FEATURE:
<223> OTHER INFORMATION: hGAPDH Reverse Primer

<400> SEQUENCE: 6
tgatggcaac aatatccact ttacc                                        25